(12) United States Patent
Flavell et al.

(10) Patent No.: US 10,785,968 B2
(45) Date of Patent: Sep. 29, 2020

(54) GENETICALLY MODIFIED NON-HUMAN ANIMALS AND METHODS OF USE THEREOF

(71) Applicants: Regeneron Pharmaceuticals, Inc., Tarrytown, NY (US); Yale University, New Haven, CT (US); Institute for Research in Biomedicine (IRB), Bellinzona (CH)

(72) Inventors: Richard Flavell, Guilford, CT (US); Till Strowig, Braunschweig (DE); Markus G. Manz, Zollikon (CH); Chiara Borsotti, Bronxville, NY (US); Madhav Dhodapkar, New Haven, CT (US); Andrew J. Murphy, Croton-on-Hudson, NY (US); Sean Stevens, San Diego, CA (US); George D. Yancopoulos, Yorktown Heights, NY (US)

(73) Assignees: Regeneron Pharmaceuticals, Inc., Tarrytown, NY (US); Yale University, New Haven, CT (US); Institute for Research in Biomedicine (IRB), Bellinzona (CH)

( * ) Notice: Subject to any disclaimer, the term of this patent is extended or adjusted under 35 U.S.C. 154(b) by 0 days.

(21) Appl. No.: 15/804,989

(22) Filed: Nov. 6, 2017

(65) Prior Publication Data
US 2018/0049413 A1 Feb. 22, 2018

Related U.S. Application Data

(62) Division of application No. 14/072,626, filed on Nov. 5, 2013, now Pat. No. 9,901,082.

(60) Provisional application No. 61/722,437, filed on Nov. 5, 2012.

(51) Int. Cl.
| | |
|---|---|
| *A01K 67/027* | (2006.01) |
| *C07K 14/535* | (2006.01) |
| *C07K 14/54* | (2006.01) |
| *C07K 14/52* | (2006.01) |
| *A61K 49/00* | (2006.01) |

(52) U.S. Cl.
CPC ...... *A01K 67/0278* (2013.01); *A01K 67/0276* (2013.01); *A01K 2207/15* (2013.01); *A01K 2217/052* (2013.01); *A01K 2217/072* (2013.01); *A01K 2217/075* (2013.01); *A01K 2217/15* (2013.01); *A01K 2227/105* (2013.01); *A01K 2267/01* (2013.01); *A61K 49/0008* (2013.01); *C07K 14/524* (2013.01); *C07K 14/535* (2013.01); *C07K 14/5403* (2013.01); *C07K 14/5412* (2013.01)

(58) Field of Classification Search
CPC ................................................ A01K 67/0248
See application file for complete search history.

(56) References Cited

U.S. PATENT DOCUMENTS

| | | | |
|---|---|---|---|
| 4,736,866 A | 4/1988 | Leder et al. |
| 4,870,009 A | 9/1989 | Evans et al. |
| 5,222,982 A | 6/1993 | Ommaya |
| 5,385,582 A | 1/1995 | Ommaya |
| 5,573,930 A | 11/1996 | Ladner et al. |
| 5,583,278 A | 12/1996 | Alt et al. |
| 5,633,426 A | 5/1997 | Namikawa et al. |
| 5,652,373 A | 7/1997 | Reisner et al. |
| 5,663,481 A | 9/1997 | Gallinger et al. |
| 5,681,729 A | 10/1997 | Kudo et al. |
| 5,709,843 A | 1/1998 | Reisner et al. |
| 5,750,826 A | 5/1998 | Borkowski et al. |
| 5,849,288 A | 12/1998 | Reisner et al. |

(Continued)

FOREIGN PATENT DOCUMENTS

| | | |
|---|---|---|
| CN | 101250553 | 8/2008 |
| EP | 0322240 | 6/1989 |

(Continued)

OTHER PUBLICATIONS

Strowig et al. (2011, PNAS, vol. 108, pp. 13218-13223) (Year: 2011).*

(Continued)

*Primary Examiner* — Thaian N. Ton
*Assistant Examiner* — David A. Montanari
(74) *Attorney, Agent, or Firm* — Tor Smeland; Ilona Gont; Brian E. Davy

(57) ABSTRACT

Genetically modified non-human animals are provided that may be used to model human hematopoietic cell development, function, or disease. The genetically modified non-human animals comprise a nucleic acid encoding human IL-6 operably linked to an IL-6 promoter. In some instances, the genetically modified non-human animal expressing human IL-6 also expresses at least one of human M-CSF, human IL-3, human GM-CSF, human SIRPa or human TPO. In some instances, the genetically modified non-human animal is immunodeficient. In some such instances, the genetically modified non-human animal is engrafted with healthy or diseased human hematopoietic cells. Also provided are methods for using the subject genetically modified non-human animals in modeling human hematopoietic cell development, function, and/or disease, as well as reagents and kits thereof that find use in making the subject genetically modified non-human animals and/or practicing the subject methods.

10 Claims, 15 Drawing Sheets
(6 of 15 Drawing Sheet(s) Filed in Color)
Specification includes a Sequence Listing.

(56) References Cited

U.S. PATENT DOCUMENTS

| | | |
|---|---|---|
| 5,866,757 A | 2/1999 | Reisner et al. |
| 6,018,096 A | 1/2000 | Keating et al. |
| 6,353,150 B1 | 3/2002 | Dick et al. |
| 6,455,756 B1 | 9/2002 | Chen et al. |
| 6,586,251 B2 | 7/2003 | Economides et al. |
| 7,273,753 B2 | 9/2007 | Crawford et al. |
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 7,759,541 B2 * | 7/2010 | Wolf ............... A01K 67/0276 800/18 |
| 8,541,646 B2 | 9/2013 | Stevens et al. |
| 8,692,052 B2 | 4/2014 | Stevens et al. |
| 8,847,004 B2 | 9/2014 | Murphy et al. |
| 8,878,001 B2 * | 11/2014 | Wang ............... A01K 67/0278 800/18 |
| 9,127,292 B2 | 9/2015 | Murphy et al. |
| 9,155,290 B2 | 10/2015 | Rojas |
| 9,193,977 B2 | 11/2015 | Murphy et al. |
| 9,301,509 B2 | 4/2016 | Stevens et al. |
| 9,402,377 B2 | 8/2016 | Flavell |
| 9,462,794 B2 | 10/2016 | Murphy et al. |
| 9,554,563 B2 | 1/2017 | Stevens et al. |
| 9,655,352 B2 | 5/2017 | Murphy et al. |
| 9,901,082 B2 | 2/2018 | Flavell et al. |
| 9,986,724 B2 | 6/2018 | Flavell et al. |
| 10,433,527 B2 | 10/2019 | Flavell et al. |
| 2002/0037523 A1 | 3/2002 | Ruben et al. |
| 2003/0028911 A1 | 2/2003 | Huang et al. |
| 2005/0208474 A1 | 9/2005 | Lau et al. |
| 2007/0254842 A1 | 11/2007 | Bankiewicz |
| 2008/0081064 A1 | 4/2008 | Jelle et al. |
| 2008/0311095 A1 | 12/2008 | Holmes et al. |
| 2009/0196903 A1 | 8/2009 | Kliman |
| 2011/0200982 A1 | 8/2011 | Stevens et al. |
| 2012/0157667 A1 | 6/2012 | Chen |
| 2013/0022996 A1 | 1/2013 | Stevens et al. |
| 2013/0024957 A1 | 1/2013 | Stevens et al. |
| 2013/0042330 A1 | 2/2013 | Murphy et al. |
| 2013/0117873 A1 | 5/2013 | Wang et al. |
| 2014/0090095 A1 | 3/2014 | Stevens et al. |
| 2014/0134662 A1 | 5/2014 | Flavell et al. |
| 2015/0047061 A1 | 2/2015 | Murphy et al. |
| 2015/0089678 A1 | 3/2015 | Murphy et al. |
| 2015/0089679 A1 | 3/2015 | Murphy et al. |
| 2015/0208622 A1 | 7/2015 | Flavell et al. |
| 2015/0327524 A1 | 11/2015 | Murphy et al. |
| 2016/0050896 A1 | 10/2016 | Murphy et al. |
| 2016/0295844 A1 | 10/2016 | Herndler-Brandstetter et al. |
| 2016/0366862 A1 | 12/2016 | Flavell et al. |
| 2016/0374321 A1 | 12/2016 | Murphy et al. |
| 2017/0172121 A1 | 6/2017 | Murphy et al. |
| 2017/0273285 A1 | 9/2017 | Murphy et al. |
| 2018/0020647 A1 | 1/2018 | Flavell et al. |

FOREIGN PATENT DOCUMENTS

| | | |
|---|---|---|
| EP | 0438053 | 7/1991 |
| EP | 0517199 | 12/1992 |
| EP | 1452093 | 9/2004 |
| GB | 2434578 A | 8/2007 |
| RU | 2425880 | 2/2011 |
| WO | WO 1988003173 | 5/1988 |
| WO | WO 1989012823 | 12/1989 |
| WO | WO 1991016910 | 11/1991 |
| WO | WO 1991018615 | 12/1991 |
| WO | WO 1993005796 | 4/1993 |
| WO | WO 1998044788 | 10/1998 |
| WO | WO 200115521 | 3/2001 |
| WO | WO 2002066630 | 8/2002 |
| WO | WO 2003018744 | 3/2003 |
| WO | WO 2003039232 | 5/2003 |
| WO | WO 2004005496 | 1/2004 |
| WO | WO 2004022738 | 3/2004 |
| WO | 2004044003 | 5/2004 |
| WO | WO 2004060052 | 7/2004 |
| WO | WO 2008010100 | 1/2008 |
| WO | WO 2008069659 | 6/2008 |
| WO | WO 2009034328 | 3/2009 |
| WO | WO 2009042917 | 4/2009 |
| WO | 2011002721 | 1/2011 |
| WO | WO 2011002727 | 1/2011 |
| WO | WO 2011044050 | 4/2011 |
| WO | WO 2012040207 | 3/2012 |
| WO | WO 2012051572 | 4/2012 |
| WO | WO 2012112544 | 8/2012 |
| WO | WO 2013063556 | 5/2013 |
| WO | WO 2014039782 | 3/2014 |
| WO | WO 2014071397 | 5/2014 |
| WO | WO 2015042557 | 3/2015 |
| WO | WO 2015179317 | 11/2015 |
| WO | WO 2016168212 | 10/2016 |

OTHER PUBLICATIONS

Miyakawa et al. (2004, Biochem. Biophys. Res. Comm., vol. 313, pp. 258-262). (Year: 2004).*

Suematsu et al. (1989, PNAS, vol. 86, pp. 7547-7551) (Year: 1989).*

McDermott et al. (2010, Blood, vol. 116(2), pp. 193-200). (Year: 2010).*

Hofker Marten H., et al., "Transgenic mouse methods and protocols"; Methods in molecular biology, vol. 209 (2002-2003), pp. 51-58.

Ito, et al (2013) "Establishment of a human allergy model using human IL-3/GM-CSF-transgenic NOG mice"; The Journal of Immunology 191(6); pp. 2890-2899.

Lu et al. (2009) "Epitope-tagged receptor knock-in mice reveal that differential desensitization of alpha2-adrenergic responses is because of ligand-selective internalization"; J. Bioi. Chem., vol. 284(19); pp. 13233-13243.

Rybchin C. N., "Principles of Genetic Engineering"; Saint-Petersburg, Publisher SPbGTU, 2002; pp. 411-413.

Abadie V., et al; (2014) "IL-15: a central regulator of celiac disease immunopathology"; Immunol Rev. 260(1):221-34.

Abboud et al., "Analysis of the Mouse CSF-1 Gene Promoter in a Transgenic Mouse Model" *The Journal of Histochemistry & Cytochemistry*, 51(7):941-949 (2003).

Alves et al.; "Characterization of the thymic IL-7 niche in vivo"; *Proceedings of the National Academy of Sciences*, 1 06(5); pp. 1512-1517, (2009).

Angulo-Barturen Inigo, et al; "A Murine Model of falciparum-Malaria by In Vivo Selection of Competent Strains in Non-Myelodepleted Mice Engrafted with Human Erythrocytes"; *PLoS ONE*, vol. 3. No. 5; May 2008, pp. 1-14; XP055166984.

Appenheimer et al (2007) "Conservation of IL-6 trans-signaling mechanisms controlling L-selectin adhesion by fever-range thermal stress"; *Eur J Immunol.* 37(10):2856-67.

Arranz Eduardo and Garrote Jose A; (2011) "IL-15 modulates the effect of retinoic acid, promoting inflammation rather than oral tolerance to dietary antigen"; Expert Rev. Gastroenterol. Hepatol. 5(3), pp. 315-317.

Auffray et al., (2009), "Blood monocytes: development, heterogeneity, and relationship with dendritic cells"; *Annual review of immunology* 27, 669-692.

Badell et al. (2000) "Human malaria in immunocompromised mice: an in vivo model to study defense mechanisms against Plasmodium falciparum"; *JEM* 192(11): pp. 1653-1659.

Baenziger et al., (2006), "Disseminated and Sustained HIV Infection in CD34+ Cord Blood Cell-Transplanted Rag2-/-γc-/-Mice"; *Proc Natl Acad Sci USA* 103: pp. 15951-15956.

Bartley, T.D. et al. (1994) Identification and cloning of a megakaryocyte growth and development factor that is a ligand for the cytokine receptor Mpl, *Cell* 77:1117-1124. (Abstract).

Becker et al., (2010), "Generation of Human Antigen-Specific Monoclonal IgM Antibodies Using Vaccinated Human Immune System Mice"; *PLoS ONE* 5(10); pp. 1-10.

(56) References Cited

OTHER PUBLICATIONS

Bergsagel et al.; (2005); "Cyclin D dysregulation: an early and unifying pathogenic event in multiple myeloma"; *Blood* 106: pp. 296-303.
Bernard, et al; "Establishing humanized mice using stem cells: maximizing the potential"; *Clinical & Experimental Immunology* vol. 152, Issue 3, pp. 406-414, (Jun. 2008).
Biedzka-Sarek; et al. "How to outwit the enemy: dendritic cells face *Salmonella*", *APMIS* 114 (9); (Sep. 2006): pp. 589-600.
Billerbeck, et al (2011) "Development of human CD4+FoxP3+ regulatory T cells in human stem cell factor-, granulocyte-macrophage colony-stimulating factor-, and interleukin-3-expressing NOD-SCID IL2Rγ(null) humanized mice"; Blood 117(11); pp. 3076-3086.
Bingle et al., (2002), "The role of tumour-associated macrophages in tumour progression: implications for new anticancer therapies"; *T Journal of pathology* 196: pp. 254-265.
Bird et al., (1988), "Single-Chain Antigen-Binding Proteins"; *Science* 242: pp. 423-426.
Bock; et al. "Improved Engraftment of Humanized Hematopoeitic Cells in Severe Combined Immunodeficient (SCID) Mice Carrying Human Cytokine Transgenes", *Journal of Exp. Med.* 182; (Dec. 1995),:pp. 2037-2043.
Bosma et al. (1989), "The mouse mutation severe combined immune deficiency (scid) is on chromosome 16"; *Immunogenetics* 29: pp. 54-56.
Brehm; et al."Parameters for establishing humanized mouse models to study human immunity: Analysis of human hematopoeitic stem cell engraftment in three immunodeficient strains of mice bearing the IL2ry null mutation", *Clinical Immunology* 135; (2010): pp. 84-98.
Brehm et al., (2012), "Engraftment of human HSCs in nonirradiated newborn NOD-scid IL2ry$^{null}$ mice is enhanced by transgenic expression of membrane-bound human SCF", *Blood* 119: pp. 2778-2788.
Burger et al., (2001) "Gp130 and ras mediated signaling in human plasma cell line INA-6: a cytokine-regulated tumor model for plasmacytoma"; *Hematol J*, 2(1): pp. 42-53.
Campbell et al., "Neurologic disease induced in transgenic mice by cerebral overexpression of interleukin 6," *Proc. Natl. Acad. Sci. USA*, 90: pp. 10061-10065; (1993).
Calvi; et al. "Osteoblastic cells regulate the haematopoietic stem cell niche", *Nature* 425 (Oct. 2003),:841-846.
Carstea, et al. (2009) "Germline competence of mouse ES and iPS cell lines: Chimera technologies and genetic background"; World Journals of Stem Cells, vol. 1, No. 1; pp. 22-29.
Chen et al., "Expression of human cytokines dramatically improves reconstitution of specific human-blood lineage cells in humanized mice" *PNAS* 106(51): (Dec. 22, 2009) 21783-21788.
Chen et al., (2012) "Human extramedullary bone marrow in mice: a novel in vivo model of genetically controlled hematopoietic microenvironment"; Blood 119(21); pp. 4971-4980.
Cheng et al., "Therapeutic Antibodies Targeting CSF1 Impede Macrophage Recruitment in a Xenograft Model of Tenosynovial Giant Cell Tumor" *Sarcoma*, Article ID 174528, pp. 1-7 (2010).
Chicha et al. "Human Adaptive Immune System Rag2-/-γc-/-Mice"; *Annals of NY Academy of Science* 104; (2005); pp. 236-243.
Chng et al., (2005), "A validated FISH trisomy index demonstrates the hyperdiploid and nonhyperdiploid dichotomy in MGUS" *Blood* 106(6): pp. 2156-2161.
Chow et al., (2011), "Studying the mononuclear phagocyte system in the molecular age" *Nature reviews Immunology* 11: pp. 788-798.
Clark, et al.; "A future for transgenic livestock", *Natures Reviews*, vol. 4; (Oct. 2003); pp. 825-833.
Cocco; et al. "CD34+ Cord Blood Cell-Transplanted Rag2-/-yc-/- Mice as a Model for Epstein-Barr Virus Infection"; *The American Journal of Pathology* 173(5): (Nov. 2008), 1369-1378.
Coussens et al.,(2013) "Neutralizing tumor-promoting chronic inflammation: a magic bullet?"; *Science* 339: pp. 286-291.

Cros et al., (2010), "Human CD14$^{dim}$ Monocytes Patrol and Sense Nucleic Acids and Viruses via TLR7 and TLRS Receptors"; *Immunity* 33: pp. 375-386.
Dai et al., "Incomplete restoration of colony-stimulating factor 1 (CSF-1) function in CSF-1-deficient Csflop/Csflop mice by transgenic expression of cell surface CSF-1" *Blood* 103(3):1114-1123 (Feb. 1, 2004).
Danos et al. (1988) "Safe and efficient generation of recombinant retroviruses with amphotropic and ecotropic host ranges"; *PNAS* 85(17): pp. 6460-6464.
Dao; et al. (1999) "Immunodeficient mice as models of human hematopoietic stem cell engraftment", *Current Opinion in Immunol* 11: 532-537.
Das, et al (2016) "Microenvironment-dependent growth of preneoplastic and malignant plasma cells in humanized mice"; Nat Med. 22(11); pp. 1351-1357.
Denning, et al (2001) "Deletion of the alpha(1,3)galactosyl transferase (GGTA1) gene and the prion protein (PrP) gene in sheep"; Nat Biotech;19; pp. 559-562.
Dennis Melvin B. (2002) "Welfare issues of genetically modified animals"; ILAR Journal, vol. 43, No. 2, pp. 100-109.
Denton PW, et al. (2012) "IL-2 receptor γ-chain molecule is critical for intestinal T-cell reconstitution in humanized mice"; Mucosal Immunol; 5(5); pp. 555-566.
Depaolo, et al: (2011) "Co-adjuvant effects of retinoic acid and IL-15 induce inflammatory immunity to dietary antigens"; *Nature.* 471; pp. 220-224.
De Raeve and Vanderkerken, (2005), "The role of the bone marrow microenvironment in multiple myeloma"; *Histol Histopathol.* 20: pp. 1227-1250.
De Sauvage, F.J. et al. (1994) "Stimulation of megakaryocytopoiesis and thrombopoiesis by the c-Mpl ligand"; *Nature* 369: pp. 533-538.
Dewan et al., (2004) "Prompt tumor formation and maintenance of constitutive NF-κB activity of multiple myeloma cells in NOD/SCID/γc$^{null}$ mice"; *Cancer Sci.* 95:564-568.
Dhodapkar, (2009), "Myeloid neighborhood in myeloma: Cancer's underbelly" *Am J Hematol.* 84: pp. 395-396.
Diminici et al. (2006) "Minimal criteria for defining multipotent mesenchymal stromal cells, The International Society for Cellular Therapy position statement"; *Cytotherapy* 8: pp. 315-317.
Drake, et al. (2012) "Engineering humanized mice for improved hematopoietic reconstitution"; Cell Mol Immunol. 9(3); pp. 215-224.
Egeblad et al., (2010), "Tumors as organs: complex tissues that interface with the entire Organism"; *Developmental Cell* 18: pp. 884-901.
Eisenbarth et al.; "Development and Characterization of a Human IL-7 Transgenic Humanized Mouse Model,"; iwhm2, 2nd International Workshop on Humanized Mice, Program & Abstract Book; Sint Olofskapel, Amsterdam, The Netherlands, Apr. 3-6, 2009, Abstract #19.
El-Ad et al. (2013) "viSNE enables visualization of high dimensional single-cell data and reveals phenotypic heterogeneity of leukemia"; Nat. Biotechnol. 31(6); pp. 545-552.
Epstein et al., (2005), "The SCID-hu myeloma model"; *Methods Mol Med*, 113: pp. 183-190.
Erta M. et al., (2012) "Interleukin-6, a major cytokine in the central nervous system"; Int J Biol Sci. 8(9):1254-66. doi: 10.7150/ijbs. 4679. Epub Oct. 25, 2012.
Extended European Search Report for EP Application No. 16157878.6 dated May 23, 2016.
Fattori, et al., (1994) "Development of Progressive Kidney Damage and Myeloma Kidney in Interleukin-6 Transgenic Mice," *Blood*, 83(9): 2570-2579.
Fattori et al., (1995)"IL-6 Expression in Neurons of Transgenic Mice Causes Reactive Astrocytosis and Increase in Ramified Microglial Cells but no Neuronal Damage," European *Journal of D Neuroscience*, 7: 2441-2449.
Felix, R. et al. (1990) "Macrophage colony stimulating factor restores In Vivo bone resorption in the OP/OP osteopetrotic mouse"; *Endocrinology* 127: pp. 2592-2594.
Fisher et al.; (1993) "Lymphoproliferative Disorders in an IL-7 Transgenic Mouse Line"; *Leukemia*, 7(2): pp. 566-568.

(56) References Cited

OTHER PUBLICATIONS

Flavell, Richard A. "Tissue-resident T cells in a novel humanized mouse model" Presentation: CSH Meeting, Apr. 16, 2015; 23 pages.
Fonseca et al., (2002), "Genomic abnormalities in monoclonal gammopathy of undetermined significance" Blood 100: pp. 1417-1424.
Foss et al; "Frequent Expression of IL-7 Gene Transcripts in Tumor Cells of Classical Hodgkin's Disease"; American Journal of Pathology, 146(1): pp. 33-39, (1995).
Fox, N., et al. (2002) "Thrombopoietin expands hematopoietic stem cells after transplantation"; J Clin Invest 110: pp. 389-394.
Freeden Jeffry et al.; "Lymphopenia in lnterleukin (IL)-7 Gene-deleted Mice Identifies IL-7 as a Nonredundant Cytokine"; J. Exp. Med., 181; pp. 1519-1526, (1995).
Fry et al., "A potential role for interleukin-7 in T-cell homeostasis," Blood, 97: 2983-2990, (2001).
Fry et al., "IL-7 comes of age," Blood, 107(1): pp. 2587-2588, (2006).
Fry et al., "The Many Faces of IL-7: From Lymphopoiesis to Peripheral T Cell Maintenance,"; Journal of Immunology, 174: pp. 6571-6576, (2005).
Fry, et al., "lnterleukin-7: from bench to clinic," Blood, 99(11): pp. 3892-3904, (2002).
Fukuchi, Y., et al., "Cytokine dependent growth of human TF-1 leukemic cell line in human GMCSF and IL-3 producing transgenic SCID mice"; Leukemia Research, vol. 22; (1998); pp. 837-843.
Galán J.E. & Curtiss, R. (1991) Distribution of the invA, -B, -C, and -D genes of S. thyphimurium among other Salmonella. Serovars: invA mutants of Salmonella typhi are deficient for entry into mammalian cells; Infect. Immun. 59(9): pp. 2901-2908.
Garcia, Sylvie , et al; "Humanized mice: Current states an perspectives"; Immunology Letters, Elsevier BV, NL, vol. 146, No. 1-2; Aug. 30, 2012; pp. 1-7; XP002681730.
Geiselhart et al., "IL-7 Administration Alters the CD4: CDS Ratio, Increases T Cell Numbers, and Increases T Cell Function in the Absence of Activation," The Journal of Immunology, 166: 3019-3027; (2001).
Goldman, et al. (2004) "Transgenic animals in medicine: integration and expression of foreign genes, theoretical and applied aspects"; Med Sci Monit, vol. 10, No. 11; pp. RA274-RA285.
Goldman; et al. "BMP4 regulates the hematopoietic stem cell niche", Blood 114(20); (Nov. 2009):pp. 4393-4401.
Goodwin et al.; "Human interleukin 7: Molecular cloning and growth factor activity on human and murine B-lineage cells"; Proc. Natl. Acad. Sci. USA, 86: pp. 302-306, (1989).
Gorantla; et al. "Human Immunodeficiency Virus Type 1 Pathobiology Studied in Humanized BALB/c-Rag2-/-Yc-/-Mice", Journal of Virology 81(6): (Mar. 2007), 2700-2712.
Goya et al., "Sustained interleukin-6 signalling leads to the development of lymphoid organ-like structures in the lung": Journal of Pathology, 200: pp. 82-87, (2003).
Greenblatt, et al. (2012) "Graft versus host disease in the bone marrow, liver and thymus humanized mouse model"; PLoS One 7(9); e44664.
Greiner; et al. "Improved Engraftment of Human Spleen Cells in NOD/LtSz-scid/scid Mice as Compared with C. B-17-scid/scid Mice", American Journal of Pathology 146(4): (Apr. 1995), 888-902.
Groen, R. W. J., et al; "Reconstructing the human hematopoietic niche in immunodeficient mice: opportunities for studying primary multiple myeloma"; Blood, vol. 120, No. 3, May 31, 2012; pp. e9-e16, XP055113167.
Guimond et al.; "Cytokine Signals in T-Cell Homeostasis"; J. lmmunother, 28; (2005); pp. 289-294.
Haley, (2003), "Species differences in the structure and function of the immune System"; Toxicology 188: pp. 49-71.
Hao et al., (2012), Macrophages in tumor microenvironments and the progression of tumors; Clinical & developmental immunology 2012: 948098.

Hayakawa J., et al, (2009), "Busulfan produces efficient human cell engraftment in NOD/LtSz-Scid IL2Rgamma(null) mice"; Stem Cells, 27(1): pp. 175-182.
Hayday Adrian and Viney Joanne L.; (2000) "The ins and outs of body surface immunology"; Science 290(5489): pp. 97-100.
Heinrich et al., "lnterleukin-6 and the acute phase response," Biochem. J., 265: 621-636, (1990).
Hideshima et al., (2007), "Understanding multiple myeloma pathogenesis in the bone marrow to identify new therapeutic targets"; Nat Rev Cancer. 7: pp. 585-598.
Hiramatsu, Hidefumi, et al; (2003) "Complete reconstitution of human lymphocytes from cord blood CD34+ cells using the NOD/SCID/$\gamma c^{null}$ mice model"; Blood, vol. 102, No. 3; Aug. 1, 2003: pp. 873-880.
Hirano et al., Purification to homogeneity and characterization of human B-cell differentiation factor (BCDF or BSFp-2), Proc. Natl. Acad. Sci. USA, 82: pp. 5490-5494, (1985).
Hirano et al., "Complementary DNA for a novel human interleukin (BSF-2) that induces B lymphocytes to produce immunoglobulin," Nature, 324: pp. 73-76, (1986).
Hirano et al., "Biological and clinical aspects of interleukin 6"; Immunology, 11: pp. 443-449, (1990).
Hirota et al., "Continuous activation of gp130, a signal-transducing receptor component for interleukin 6-related cytokines, causes myocardial hypertrophy in mice"; Proc. Natl. Acad. Sci. D USA, 92: pp. 4862-4866, (1995).
Hofer; et al. "RAG2-/-yc-/-Mice Transplanted with CD34+ Cells from Human Cord Blood Show Low Levels of Intestinal Engraftment and Are Resistant to Rectal Transmission of Human Immunodeficiency Virus", Journal of Virology 82(24): (Dec. 2008), 12145-12153.
Holyoake et al. (1999) "Functional differences between transplantable human hematopoietic stem cells from fetal liver, cord blood, and adult marrow"; Exp Hematol. 27(9): pp. 1418-1427.
Houdebine, Louis-Marie (2007) "Transgenic animal models in biomedical research"; Methods in Molecular Biology, vol. 360; pp. 163-202.
Hu, Z. et al; "Macrophages prevent human red blood cell reconstitution in immunodeficient mice"; Blood, vol. 118, No. 22; Nov. 24, 2011; pp. 5938-5946.
Huo; et al. "Humanized Mouse Model of Cooley's Anemia", J. Biol. Chem 284(8): (Feb. 2009), 4889-4896.
Huntington et al., (2009), "IL-15 trans-presentation promotes human NK cell development and differentiation in vivo"; Journal of experimental medicine 206(1); pp. 25.
Huston et al., (1988), "Protein engineering of antibody binding sites: recovery of specific activity in an anti-digoxin single-chain Fv analogue produced in Escherichia coli"; Proc. Natl. Acad. Sci. USA 85(16): pp. 5879-5883.
Irvine et al., "Colony-stimulating factor-1 (CSF-1) delivers a proatherogenic signal to human macrophages" Journal of Leukocyte Biology, 85:278-288 (Feb. 2009).
Ishikawa et al. (2005), "Development of functional human blood and immune systems in NOD/SCID/IL2 receptor {gamma} chain-(null) mice"; Blood. 106(5); Sep. 1, 2005: 1565-73. Epub May 26, 2005.
Ito et al., "NOD/SCID/gamma(c)(null) mouse: an excellent recipient mouse model for engraftment of human cells" Blood 100(9); Nov. 1, 2002; pp. 3175-3182.
IWHM2 2nd International Workshop on Humanized Mice, Colorado State University, Program & Abstract Book. (Apr. 3-6, 2009), Sint Olofskapei/Amsterdam, NL.
The Jackson Laboratory, "Strain Name: C; 129S4-Rag2tm1.1Flv; Csf1tm1.1(CSF1)Flv; Il2rgtm1.1Flv/J" JAX Mice Database, http://jaxmic.jax.org/strain/107708.html, 6 pages (Jan. 26, 2012).
Jacob et al: (2010) "Gene targeting in the rat: advances and opportunities"; Trends Genet. 26(12):510-8. doi: 10.1016/j.tig.2010.08.006. Epub Oct. 1, 2010.
Jacobs et al., "IL-7 Is Essential for Homeostatic Control ofT Cell Metabolism In Vivo" The Journal of Immunology, 184: 3461-3469, (2010).
Jimenez-Diaz et al. (2009) "Improved murine model of malaria using Plasmodium falciparum competent strains and non-

(56) References Cited

OTHER PUBLICATIONS myelodepleted NOD-scid IL2Rgnull mice engrafted with human erythrocytes. Antimicrob Agents"; *Chemother* 53: pp. 4533-4536.
Kalueff A.V. et al., (2004) "Intranasal administration of human IL-6 increases the severity of chemically induced seizures in rats" *Neurosci Lett.* 365(2):106-110.
Kamel-Reid and Dick, "Engraftment of immune-deficient mice with human hematopoietic stem cells"; *Science.* 242 (4886):Dec. 23, 1988; 1706-1709.
Kandalaft et al., "Angiogenesis and the tumor vasculature as antitumor immune modulators: the role of vascular endothelial growth factor and endothelin"; *Curr Top Microbiol Immunol.* (2011); 344: 129-48.
Kang et al., "Defective Development of y/o T Cells in Interleukin 7 Receptor-deficient Mice Is Due to Impaired Expression of T Cell Receptor y Genes," *J. Exp. Med.*, 190(7): 973-982, (1999).
Katano, I. et al; (2015) "Predominant development of mature and functional human NK cells in a novel human IL-2-producing transgenic NOG mouse"; *Journal of Immunology*,194(7): pp. 3513-3525.
Kaufmann et al., (2004), "Both IGH translocations and chromosome 13q deletions are early events in monoclonalgammopathy of undetermined significance and do not evolve during transition to multiple myeloma" *Leukemia.* 18: pp. 1879-1882.
Kaushansky, K. et al. (1994) "Promotion of megakaryocyte progenitor expansion and differentiation by the c-Mpl ligand thrombopoietin", *Nature* 369: pp. 568-571.
Kaushansky, K. (1998) "Thrombopoietin", *N Engl J Med* 339: pp. 746-754.
Kaushansky, K. (2005) "The molecular mechanisms that control thrombopoiesis", *J Clin Invest* 115: pp. 3339-3347.
Kaushansky, K. (2008) "Historical review: megakaryopoiesis and thrombopoiesis", *Blood* 111: pp. 981-986.
Keller et al., "Molecular and Cellular Biology of Interleukin-6 and its Receptor," *Frontiers in Bioscience*, 1: 340-357, 1996.
Kieper et al., (2002) "Overexpression of Interleukin (IL)-7 Leads to IL-15-independent Generation of Memory Phenotype CD+T Cells" *J. Exp. Med.*, 195(12): 1533-1539.
Kieran Seay et al; (2015) In Vivo Activation of Human NK Cells by Treatment with an Interleukin-15 Superagonist Potently Inhibits Acute InVivo HIV-1 Infection in Humanized Mice; *Journal of Virology*, vol. 89. No. 12; pp. 6264-6274.
Kim et al., (2011) "Seeing is Believing: Illuminating the Source of In Vivo Interleukin-7"; *Immune Network*, 11(1): pp. 1-7.
Kim, D. K., et al., (1998) "Engraftment of human myelodysplastic syndrome derived cell line in transgenic severe combined immunodeficient (TG-SCID) mice expressing human GM-CSF and IL-3"; *European Journal of Haematology*, vol. 61; pp. 93-99.
Kinoshita Ichiro, et al (2008) "Molecular pathophysiology of lung cancer-identification of lung cancer stem cells"; Nippon Rinsho, vol. 66, Suppl 6; pp. 95-99 (w/partial English translation).
Kirito, K. et al. (2003) "Thrombopoietin stimulates Hoxb4 expression: an explanation for the favorable effects of TPO on hematopoietic stem cells"; *Blood* 102:3172-3178.
Kishimoto, Tadamitsu, (1989) "The Biology of Interleukin-6"; *Blood*, 74(1): pp. 1-10.
Kishimoto, Tadamitsu, (2010) "IL-6: from its discovery to clinical applications"; International *Immunology*, 22(5): pp. 347-352.
Kirma et al., "Overexpression of the Colony-Stimulating Factor (CSF-1) and/or Its Receptor c-fms in Mammary Glands of Transgenic Mice Results in Hyperplasia and Tumor Formulation" *Cancer Resesarch*, 64:4162-4170 (Jun. 15, 2004).
Kondo; et al. (2001) "Lymphocyte development from hematopoietic stem cells", *Current Opn Gen & Dev* 11: 520-526.
Kosco-Vilbois; et al. "A mightier mouse with human adaptive immunity", *Nature Biotechnology* (Jun. 2004), 22 (6):684-685.
Kovalchuk et al., (2002) "IL-6 transgenic mouse model for extraosseous plasmacytoma" *PNAS*, 99(3): pp. 1509-1514.
Kraus et al. (2010), "A more cost effective and rapid high percentage germ-line transmitting chimeric mouse generation procedure via microinjection of 2-cell, 4-cell, and 8-cell embryos with ES and iPS cells" *Genesis* 48(6): pp. 394-399.
Kuehl and Bergsagel, (2002), "Multiple myeloma: evolving genetic events and host interactions"; *Nat Rev Cancer.* 2(3): pp. 175-187.
Kukreja et al., (2006) "Enhancement of clonogenicity of human multiple myeloma by dendritic cells", *J Exp Med.* 203(8): pp. 1859-1865.
Kuruvilla; et al, "Dengue virus infection and immune response in humanized RAG2-1-yc-1-(RAG-hu) mice", *Virology* (2007), 369:143-152.
Kuter, D.J. & Rosenberg, R.D. (1995) "The reciprocal relationship of thrombopoietin (c-Mpl ligand) to changes in the platelet mass during busulfan-induced thrombocytopenia in the rabbit", *Blood* 85: pp. 2720-2730.
Landgren et al., (2009), "Monoclonal gammopathy of undetermined significance (MGUS) consistently precedes multiple myeloma: a prospective study"; *Blood* 113(22): pp. 5412-5417.
Lapidot et al., (1992) "Cytokine stimulation of multilineage hematopoiesis from immature human cells engrafted in SCID mice", *Science* 255(5048):Feb. 28, 1992; 1137-41.
Lebrec Herve, et al: "Homeostasis of human NK cells is not IL-15 dependent"; *J Immunol.* 191(11): Dec. 1, 2013; pp. 5551-5558. doi: 10.4049/jimmunol.1301000. Epub Nov. 1, 2013.
Legrand; et al. "Experimental Models to Study Development and Function of the Human Immune System in Vivo", *The Journal of Immunology* (2006), 176: 2053-2058.
Legrand; et al. "Humanized Mice for Modeling Human Infectious Disease: Challenges, Progress, and Outlook", *Cell Host & Microbe*, vol. 6, No. 1; (Jul. 2009); pp. 5-9. XP00258476.
Legrand et al., (2011) "Functional CD47/signal regulatory protein alpha (SIRP(alpha)) interaction is required for optimal human T- and natural killer-(NK) cell homeostasis in vivo", *Proc Natl Acad Sci USA* 108(32): pp. 13224-13229.
Lemay L.G. et al; (1990) "Role of interleukin 6 in fever in rats"; *Am J Physiol.* 258(3 Pt 2):R798-803.
Libby; et al. "Humanized nonobese diabetic-scid IL2ry null mice are susceptible to lethal *Salmonella typhi* infection", *PNAS* 107(35): (Aug. 2010), 15589-15594.
Lie and Petropoulos (1998) "Advances in quantitative PCR technology: 5' nuclease assays"; Curr. Opin. Biotechnology 9(1); pp. 43-48.
Liton et al., (2005), "Specific Targeting of Gene Expression to a Subset of Human Trabecular Meshwork Cells Using the Chitinase 3-Like 1 Promoter"; Invest Ophthalmol Vis Sci. 46(1):183-90.
Lombard-Platet et al., (1995) "Expression of Functional MHC Class II Molecules by a Mouse Pro-B Cell Clone," *Developmental Immunology*, 4: 85-92.
Lok, S. et al. (1994) "Cloning and expression of murine thrombopoietin cDNA and stimulation of platelet production in vivo", Nature 369: pp. 565-568.
Luo; et al., (2001) "Knock-in mice with chimeric human/murine p53 gene develop normally and show wild-type p53 responses to DNA damaging agents: a new biomedical research tool", *Oncogene* 20:320-328.
Lupton et al., (1990) "Characterization of the Human and Murine IL-7 Genes," *The Journal of Immunology*, 144(9): 3592-3601.
Ma et al., (2006), "Diverse functions of IL-2, IL-15, and IL-7 in lymphoid homeostasis"; *Annu Rev Immunol.* 24: 657-79.
MacBride Megan M.; "Meeting report: International Workshop on Humanized Mice 5"; Mar. 8, 2016; XP002758867.
MacChiarini, et al. "Humanized mice: are we there yet?"; *Journal of Experimental Medicine*, vol. 202, No. 10; (Nov. 2005); pp. 1307-1311; XP002559426.
Mahajan et al., (2005) "Homeostasis of T Cell Diversity," *Cellular & Molecular Immunology*, 2(1): pp. 1-10.
Maione et al., "Coexpression of IL-6 and soluble IL-6R causes nodular regenerative hyperplasia and adenomas of the liver"; *The EMBO Journal*, 17(19): 5588-5597, (1998).
Majumder et al. (1996) "Xenogeneic expression of human stem cell factor in transgenic mice mimics codominant c-kit mutations", *Blood* 87(8):Apr. 15, 1996; 3203-11.

(56) References Cited

OTHER PUBLICATIONS

Maksimenko, et al (2013) "Use of transgenic animals in biotechnology: prospects and problems"; Acta Naturae, vol. 5, No. 1; pp. 33-46.
Manz Markus M., et al.; "Human-Hemato-Lymphoid-System Mice: Opportunities and Challenges", *Immunity*, vol. 26, No. 5; (May 2007); pp. 537-541.
Manz; et al. "Renaissance for mouse models of human hematopoiesis and immunobiology", *Nature Immun.* 10(10): (Oct. 2009), 1039-1042.
Mason; et al. "Alcohol Exacerbates Murine Pulmonary Tuberculosis", *Infection and Immunity* 72 (5): (May 2004):2556-2563.
Mazurier; et al. (1999) "A Novel Immunodeficient Mouse Model-RAG2 X Common Cytokine Receptor y Chain Double Mutants-Requiring Exogenous Cytokine Administration for Human Hematopoietic Stem Cell Engraftment", *Journal of Interferon and Cytokine Research* 19:533-541.
Mazzucchelli et al., "lnterleukin-7 receptor expression: intelligent design," *Nature*, 7: 144-154, (2007).
Mazzucchelli et al., (2009) "Visualization and Identification of IL-7 Producing Cells in Reporter Mice" *PLOS ONE*, 4(11): p. e7637.
McBurney et al. "Murine PGK-1 promoter drives widespread but not uniform expression in transgenic mice"; *Dev Dyn.* 200(4): (Aug. 1994); 278-93.
McCune et al., "The SCID-hu mouse: murine model for the analysis of human hematolymphoid differentiation and function" *Science* 241(4873): Sep. 23, 1988; 1632-9.
Mestas & Hughes, "Of mice and not men: differences between mouse and human immunology"; *J Immunol.* 172(5): Mar. 1, 2004: 2731-8.
Mertsching et al., (1995) "IL-7 transgenic mice: analysis of the role of IL-7 in teh differentiation of thymocytes in vivo and in vitro"; *International Immunology*, 7(3): 401-414.
Meyer et al. "Gene targeting by homologous recombination in mouse zygotes mediated by zinc-finger nucleases"; *Proc Natl Acad Sci U S A.* 107(34) :Aug. 24, 2010; 15022-6. doi: 10.1073/pnas. 1009424107. Epub Aug. 4, 2010.
Miller et al. "Generation of helper-free amphotropic retroviruses that transduce a dominant-acting, methotrexate-resistant dihydrofolate reductase gene"; *Mol Cell Biol.*5(3): (Mar. 1985) pp. 431-437 . . . .
Miller et al. "Redesign of retrovirus packaging cell lines to avoid recombination leading to helper virus production"; *Mol Cell Biol.* 6(8): (Aug. 1986); 2895-902.
Mittrucker; et al. (2000) "Cutting Edge: Role of B Lymphocytes in Protective Immunity Against *Salmonella typhimurium* Infection", *J. lmmunol.*164: pp. 1648-1652.
Miyakawa et al.; (2004) "Establishment of a new model of human multiple myeloma using NOD/SCID/$y_c^{null}$ (NOG) mice"; *Biochem. Biophys. Res. Comm.*, vol. 313; pp. 258-262.
Mlecnik Bernhard, et al; (2014) "Functional network pipeline reveals genetic determinants associated with in situ lymphocyte proliferation and survival of cancer patients"; *Sci Transl Med.* 6: 228ra37.
Moreadith et al. (1997) "Gene targeting in embryonic stem cells: the new physiology and metabolism"; J. Mol. Med.75(3); pp. 208-216.
Moreno et al. (2006) The course of infections and pathology in immunomodulated NOD/LtSz-SCID mice inoculated with Plasmodium falciparum laboratory lines and clinical isolates. *Int. J. Parasitol.* 36:361-369).
Mosier et al., "Transfer of a functional human immune system to mice with severe combined immunodeficiency"; *Nature* 335(6187): Sep. 15, 1988; pp. 256-259.
Motz and Coukos, "Deciphering and reversing tumor immune suppression"; *Immunity* 39(1): Jul. 25, 2013; 61-73.
Mullins (1996) "Transgenesis in the rat and larger mammals"; J Clin Invest,97; pp. 1557 15-60.
Munitic et al., (2004) "Dynamic regulation of IL-7 receptor expression is required for normal thymopoiesis" *Blood*, 104: 4165-4172.

Munoz et al., (2009) "Constraints to Progress in Embryonic Stem Cells from Domestic Species," Stem Cell Rev. and Rep., 5:6-9.
Murphy et al., (1993) "Antitumor Effects of Interleukin-7 and Adoptive Immunotherapy on Human Colon Carcinoma Xenografts" *J. Clin. Invest.*, 92: 1918-1924.
Murphy, D., BAC-based Modifications of the Mouse Genome: The Big and the Backward, Wellcome Trust Advanced Course: Genetic Manipulation of ES Cells, 58 pages (2009).
Murphy, D. MFA: the turducken of alleles*, Wellcome Trust Advanced Course: Genetic Manipulation of ES Cells, 76 pages (2010).
Murphy William J. et al; (2012) "NK cells—from bench to clinic"; *Biol Blood Marrow Transplant* 18: pp. S2-S7.
Murray; et al. "Thrombopoietin mobilizes CD34+ cell subsets into peripheral blood and expands multilineage progenitors in bone marrow of cancer patients with normal hematopoiesis", *Exp Hematol* 26(3): (Mar. 1998), 207-216.
Nagaki et al. (2000) "SHPS-1 regulates integrin-mediated cytoskeletal reorganization and cell motility"; EMBO J. 19(24); pp. 6721-6731.
Nagy et al. "Embryonic stem cells alone are able to support fetal development in the mouse"; *Development* 110(3) (Nov. 1990):815-21.
Naka et al., (2002) "The paradigm of IL-6: from basic science to medicine," *Arthritis Research*, 4(3): S233-S242.
Nelson and Bissell, (2006) "Of extracellular matrix, scaffolds, and signaling: tissue architecture regulates development, homeostasis, and cancer"; *Annu Rev Cell Dev Biol.* 22:287-309.
Nevus Biologicals-a Bio-Techne Brand, "Human IL-6 Protein 5 µg", *NBP2-34901* (4 pages) (2016).
Nicolini; et al.; (2004) "NOD/SCID mice engineered to express human IL-3, GM-CSF and Steel factor constitutively mobilize engrafted human progenitors and compromise human stem cell regeneration", *Leukemia*, 18:341-347.
Niemann et al., "Transgenic farm animals. present and future," *Rev. Sci. Tech. Off. Int. Epiz.*, 24(1):285-298, (2005).
Nishimura, et al; (2000) "Differential Roles of Interleukin 15 mRNA Isoforms Generated by Alternative Splicing in Immune Responses In Vivo"; J Exp Med. 191(1); pp. 157-170.
Nochi T, et al. (2013) "Cryptopatches are essential for the development of human GALT"; Cell Rep; 3(6); pp. 1874-1884.
Northemann, et al (1989) "Structure of the Rat Interleukin 6 Gene and Its Expression in Macrophage-derived Cell" *J Biol Chem.* 264(27):16072-82.
O'Connell et al., (2010) "Lentiviral Vector Delivery of Human Interleukin-7 (hiL-7) to Human Immune System (HIS) Mice Expands T Lymphocyte Populations," *PLOS ONE*, 5(8): 1-10.
Papanicolaou Dimitris et al., (1998) "The Pathophysiologic Roles of Interleukin-6 in Human Disease," *Ann Intern Med.*, 128: 127-137.
Pear et al. "Production of high-titer helper-free retroviruses by transient transfection"; Proc Natl *Acad Sci U S A.* 90(18): Sep. 15, 1993; pp. 8392-8396.
Pearson et al. (2008), "Creation of "Humanized" Mice to Study Human Immunity"; Curr. *Protoc. Immunol.* 81: pp. 1-15.
Pek et al., "Characterization and IL-15 dependence of NK cells in humanized mice"; *Immunobiology*. 216(1-2): (Jan.-Feb. 2011); pp. 218-224. doi: 10.1016/j.imbio.2010.04.008. Epub May 13, 2010.
Peters et al., (1996) "The Function of the Soluble Interleukin 6 (IL-6) Receptor In Vivo: Sensitization of Human Soluble IL-6 Receptor Transgenic Mice Towards IL-6 and Prolongation of the Plasma D Half-life ofiL-6" *J. Exp. Med.*, 183:1399-1406.
Pierfrancesco Tassone, et al: "A clinically relevant SCID-hu in vivo model of human multiple myeloma"; *Blood. American Society of Hematology*. US. vol. 106. No. 2; Jul. 15, 2005; pp. 713-716; XP002633148.
Pixley et al., "CSF-1 regulation of the wandering macrophage: complexity in action" Trends in *Cell Biology*, 14(11): 628-638 (Nov. 2004).
Pleiman et al., (1991) "Organization of the Murine and Human lnterleukin-7 Receptor Genes: Two mRNAs Generated by Differential Splicing and Presence of a Type 1-lnterferon-lnducible Promoter" *Molecular and Cellular Biology*, 11 (6): 3052-3059.
Polejaeva et al (2000) "Cloned pigs produced by nuclear transfer from adult somatic cells"; Nature 407; pp. 86-90.

(56) References Cited

OTHER PUBLICATIONS

Pollard, Jeffrey W.; "Tumour-educated macrophages promote tumour progression and metastasis"; *Nature Reviews*, 4; (Jan. 2004); pp. 71-78 . . . .

Poueymirou et al. (2007) "F0 generation mice that are essentially fully derived from the donor gene-targeted ES cells allowing immediate phenotypic analyses," *Nat Biot* 25(1):91-99.

Prelle et al., (2002) "Pluripotent Stem Cells—Model of Embryonic Development, Tool for Gene Targeting, and Basis of Cell Therapy," *Anal. Histol. Embryol.* 31; pp. 169-186.

Qian, H. et al. (2007) "Critical role of thrombopoietin in maintaining adult quiescent hematopoietic stem cells," *Cell Stem Cell* 1:671-684.

Qian and Pollard, (2010) "Macrophage diversity enhances tumor progression and metastasis" *Cell* 141(1) pp. 39-51.

Rämer Patrick C. et al; (2011) "Mice with human immune system components as in vivo models for infections with human pathogens"; *Immunol Cell Biol.* 89(3):408-16. doi: 10.1038/icb.2010.151. Epub Feb. 8, 2011.

Rathinam et al., "Efficient differentiation and function of human macrophages in humaized CSF-1 mice" *Blood*, 118(11):3119-3132 (Sep. 15, 2011).

Rathinam et al., "Efficient differentiation and function of human macrophages in humaized CSF-1 mice" *Blood*, 118(11):3119-3128 (Sep. 15, 2011)—Supplemental Figures.

Raulet, (2006) "Missing self recognition and self tolerance of natural killer (NK) cells" *Seminars in immunology* 18(3):145-50.

Repass et al., (2009) "IL7-hCD25 and IL7-Cre BAC transgenic mouse lines: New tools for analysis of IL-7 expressing cells," *Genesis*, 47(4): 281-287.

Rich et al., (1993) "Cutaneous Lymphoproliferation and Lymphomas in lnterleukin 7 Transgenic Mice," *J. Exp. Med.*, 177: 305-316.

Rieger et al.; "Hematopoietic Cytokines Can Instruct Lineage Choice"; *Science*, 325; (Jul. 10, 2009); pp. 217-218.

Ring, Aaron M. et al; (2012) "Mechanistic and structural insight into the functional dichotomy between IL-2 and IL-15"; *Nat Immunol.* 13(12): pp. 1187-1195.

Rohrschneider, L.R. et al. (1997) "Growth and differentiation signals regulated by the MCSF receptor", *Mol. Reprod. Dev.* 46:96-103.

Rongvaux, Anthony; "Improvement of human-hemato-lymphoid-system mice: the human Thrombopoietin knock-in mouse"; IWHM2 2nd International Workshop on Humanized Mice, PowerPoint Presentation; (Apr. 3-6, 2009); Sint Olofskapei/Amsterdam, NL; pp. 1-20.

Rongvaux; "Human Thrombopoietin knockin mice efficiently support human hematopoiesis", Flavell Lab, Yale University (ASH—Dec. 6, 2010).

Rongvaux, A., et al.; "Human thrombopoietin knockin mice efficiently support human hematopoiesis in vivo", PNAS, vol. 108, No. 6; (Feb. 2011); pp. 2378-2383.

Rongvaux et al., (2013), "Human hemato-lymphoid system mice: current use and future potential for medicine," *Annu Rev Immunol.* 31: 635-74. doi: 10.1146/annurev-immunol-032712-095921. Epub Jan. 16, 2013.

Rongvaux Anthony et al: "Development and function of human innate immune cells in a humanized mouse model"; *Nature Biotechnology*. vol. 32. No. 4; (Apr. 2014) pp. 364-372.

Rongvaux A. et al: (2012) "MISTRG: a novel humanised mouse model to study human hematopoiesis and myeloid development and function in vivo"; *Immunology*, vol. 137, No. 1, Suppl. 1; pp. 184.

Roychowdhury Sameek, et al; (2005) "IL-15 but not IL-2 rapidly induces lethal xenogeneic graft-versus-host disease"; *Blood* 106(7): pp. 2433-2435. Epub Jun. 23, 2005.

Ryan et al., "Rescue of the colony-stimulating factor 1 (CSF-1)-nullizygous mouse (Csflop/Csflop) phenotype with CSF-1 transgene and identification of sites of local CSF-1 synthesis" *Blood*, 98(1):74-84 (Jul. 2001).

Saha et al; (2009) "Technical challenges in using human induced pluripotent stem cells to model disease"; *Cell Stem Cell.*5(6); pp. 584-595.

Samaridis et al., (1991) "Development of lymphocytes in intereleukin 7-transgenic mice" *Eur. J. lmmunol.*, 21: 453-460.

Sarrazin et al., "MafB Restricts M-CSF-Dependent Myeloid Commitment Divisions of Hematopoietic Stem Cells" *Cell*, 138:300-313 (Jul. 24, 2009).

Sawamura D. et al.; (1998) "Induction of keratinocyte proliferation and lymphocytic infiltration by in vivo introduction of the IL-6 gene into keratinocytes and possibility of keratinocyte gene therapy for inflammatory skin diseases using IL-6 mutant genes"; *J Immunol.* 161(10): 5633-5639.

Schluns et al.; "lnterleukin-7 mediates the homeostasis of naive and memory COST cells in vivo"; *Nature Immunology*,1(5); (2000); pp. 426-432.

Schorpp et al. (1996) "The human ubiquitin C promoter directs high ubiquitous expression of transgenes in mice," *Nucleic Acids Res.* 24(9):1787-8.

Scudellari, Megan; "The innate debate over HSCs"; *Nature Reports Stem Cells*; (published online Aug. 6, 2009 / doi: 10.1038/stemcells.2009.103). 1 page.

Semenza, G. L. et al; "Polycythemia in transgenic mice expressing the human erythropoietin gene"; *Proceedings of The National Academy of Sciences*, vol. 86, No. 7; (Apr. 1989); pp. 2301-2305.

Semenza Gregg L., et al; "Cell-type-specific and hypoxia-inducible expression of the human erythropoietin gene in transgenic mice"; *Genetics*, vol. 88; (Oct. 1991); pp. 8725-8729.

Setty Mala, et al: (2015) "Distinct and Synergistic Contributions of Epithelial Stress and Adaptive Immunity to Functions of Intraepithelial Killer Cells and Active Celiac Disease"; *Gastroenterology* 149(3):681-91.e10. doi: 10.1053/j.gastro.2015.05.013. Epub May 19, 2015.

Shalapour et al.; (2010) "Commensal microflora and interferon-[gamma] promote steady-state interleukin-7 production in vivo"; *European Journal of Immunology*, 40(9); pp. 2391-2399.

Sherr, C.J. et al. (1988) "Macrophage colony-stimulating factor, CSF-1, and its proto-oncogeneencoded receptor," *Cold Spring Harb. Symp. Quant. Biol.* 53 Pt 1:521-530.

Shinobara, et al. (2007) "Active integration: new strategies for transgenesis"; Transgenic research, vol. 16; pp. 333-339.

Shultz et al., (2000), "NOD/LtSz-Rag1null mice: an immunodeficient and radioresistant model for engraftment of human hematolymphoid cells, HIV infection, and adoptive transfer of NOD mouse diabetogenic T cells" *J Immunol.* 164(5):2496-507.

Shultz; et al; "Human Lymphoid and Myeloid Cell Development in NOD/LtSz-scid IL2Ry null Mice Engrafted with Mobilized Human Hempoietic Stem Cells", *J Immunol* (2005), 174:6477-6489.

Shultz, Leonard D., et al; "Humanized mice for immune system investigation: progress, promise and challenges"; *Nature Reviews Immunology*, vol. 12, No. 11; (Nov. 1, 2012); pp. 786-798. XP055064740.

Shultz L D et al; "Humanized mice in translational biomedical research"; *The Journal of Immunology. Nature Pub. Group*. GB, vol. 7. No. 2; (Feb. 2007) pp. 118-130. XP002493022.

Silva et al.; (2011) "IL-7 Contributes to the Progression of Human T-cell Acute Lymphoblastic Leukemias"; *Cancer Research*, 71 (14); pp. 4780-4789.

Skjot et al. (2002) "Epitope mapping of the immunodominant antigen TB10.4 and the two homologous proteins TB10.3 and TB12.9, which constitute a subfamily of the esat-6 gene family," *Infect. Immun.* 70:5446-5453.

Socolovsky, M. et al. (1998) "Cytokines in hematopoiesis: specificity and redundancy in receptor function," *Adv. Protein Chem.* 52:141-198.

Soderquest et al., (2011) "Monocytes control natural killer cell differentiation to effector phenotypes," *Blood.* 117(17):4511-8. doi: 10.1182/blood-2010-10-312264. Epub Mar. 9, 2011.

Sohn B; et al. "Expression and characterization of bioactive human thrombopoietin in the milk of transgenic mice", *DNA Cell Biol* (Nov. 1999), 18(11):845-852.

Song; et al; "A Mouse Model for the Human Pathogen *Salmonella typhi*", *Cell Host & Microbe* (Oct. 2010), 17(8):369-376.

(56) References Cited

OTHER PUBLICATIONS

Spits, Hergen; "New models of human immunity"; *Nature Biotechnology* vol. 32, No. 4; (Apr. 2014), pp. 335-336.
Stanley, E. Richard, "Lineage Commitment: Cytokines Instruct, At Last!" *Cell Stem Cell*, 5; (Sep. 4, 2009); pp. 234-236.
Stanley, E.R. et al. (1997) "Biology and action of colony—stimulating factor-1," *Mol. Reprod. Dev.* 1997; 46:4-10.
Strowig et al., (2011) "Transgenic expression of human signal regulatory protein alpha in Rag2-/-γc-/-mice improves engraftment of human hematopoietic cells in humanized mice", *PNAS* 108(32); pp. 13218-13223.
Strowig Till et al; "Humanized mouse models of infectious diseases"; *Drug Discovery Today: Disease Models*.; (Jan. 2012); pp. e11-e16; XP055166844.
Strowig et al., (2010) "Human NK cells of mice with reconstituted human immune system components require preactivation to acquire functional competence," *Blood*. 116(20):4158-67. doi: 10.1182/blood-2010-02-270678. Epub Jul. 29, 2010.
Suematsu et al.; (1989) "IgG1 plasmacytosis in interleukin 6 transgenic mice"; *Proc. Natl. Acad. Sci. USA*, 86; pp. 7547-7551.
Suematsu et al.; (1992) "Generation of plasmacytomas with the chromosomal translocation t(12;15) in interleukin 6 transgenic mice"; *Proc. Natl. Acad. Sci. USA*, 89; pp. 232-235.
Sugita et al.; (1990) "Functional Murine lnterleukin 6 Receptor with the Intracisternal a Particle Gene Product at its Cytoplasmic Domain"; *J. Exp. Med.*, 171; pp. 2001-2009.
Takagi et al., (2012) "Membrane-bound human SCF/KL promotes in vivo human hematopoietic engraftment and myeloid differentiation," *Blood*. 119(12):2768-77. doi: 10.1182/blood-2011-05-353201. Epub Jan. 25, 2012.
Takenaka et al., (2007), Polymorphism in Sirpa modulates engraftment of human hematopoietic stem cells; *Nature Immunology* 8: 1313-1323.
Takizawa & Manz, (2007) "Macrophage tolerance: CD47-SIRP-alpha-mediated signals matter," *Nat Immunol*. 8(12):1287-9.
Tan et al.; (2001) "IL-7 is critical for homeostatic proliferation and survival of naive T cells"; *PNAS*, 98(15); pp. 8732-8737.
Tanabe et al.; (1988) "Genomic Structure of the Murine IL-6 Gene—High Degree Conservation of Potential Regulatory Sequences between Mouse and Human"; *The Journal of Immunology, D* 141; pp. 3875-3881.
Tang, 920130 "Tumor-associated macrophages as potential diagnostic and prognostic biomarkers in breast cancer," *Cancer Lett*. 332(1):3-10. doi: 10.1016/j.canlet.2013.01.024. Epub Jan. 21, 2013.
Tassone et al., (2005) "A clinically relevant SCID-hu in vivo model of human multiple myeloma," *Blood*. 106(2):713-6. Epub Apr. 7, 2005.
Theocharides, et al; (2012) "Disruption of SIRPα signaling in macrophages eliminates human acute myeloid leukemia stem cells in xenografts"; *J Exp Med*. 209(10); pp. 1883-1899.
Tong et al; "Production of p53 gene knockout rats by homologous recombination in embryonic stem cells"; *Nature*. Sep. 9, 2010; pp. 211-215.
Traggiai; et al. "Development of a Human Adaptive Immune System in Cord Blood Cell-Transplanted Mice", *Science* (Apr. 2004), 304:104-107.
Tsantikos et al.; (2010) "Autoimmune Disease in Lyn-Deficient Mice is Dependent on an Inflammatory Environment Established by IL-6"; *The Journal of Immunoloqy*, 184; pp. 1348-1360.
Tsujinaka et al.; (1995) "Muscle Undergoes Atrophy in Associate with Increase of Lysosomal Cathepsin Activity in Interleukin-6 Transgenic Mouse"; *Biochemical and Biophysical Research Communication*, 207(1); pp. 168-174.
Tsujinaka et al.; (1996) "Interleukin 6 Receptor Antibody Inhibits Muscle Atrophy and Modulates Proteolytic Systems in Interleukin 6 Transgenic Mice"; *J. Clin. Invest.*, 97(1 ); pp. 244-249.
Tsuruta, Lisako, et al, (2003) "Transcriptional Regulation of Cytokine Genes"; *Cytokines & Cytokine Receptors: Physiology and Pathological Disorders*, Chapter 23, pp. 383-403.

Ueda, Otoya et al; "Novel genetically-humanized mouse model established to evaluate efficacy of therapeutic agents to human interleukin-6 receptor"; *Scientific Reports. Nature Publishing Group*, GB, vol. 3; Jan. 1, 2013; pp. 1196; XP002692003.
Uehira et al.; (1998) "Immunologic Abnormalities Exhibited in IL-7 Transgenic Mice with Dermatitis"; *J. Invest Dermatol*, 110; pp. 740-745.
Uehira et al.; (1993) "The development of dermatitis infiltrated by γδ T cells in IL-7 transgenic mice"; *International Immunology*, 5(12); pp. 1619-1627.
Valenzuela et al. (2003) "High-throughput engineering of the mouse genome coupled with high-resolution expression analysis," *Nat Biot* 21 (6):652-659.
Valmori et al., (1998) "Enhanced Generation of Specific Tumor-Reactive CTL In Vitro by Selected Melan-A/MART-1 Immunodominant Peptide Analogues" *Journal of Immunology* 160:1750-1758.
Van De Wiele et al.; (2007) "Impaired thymopoiesis in interleukin-7 receptor transgenic mice is not corrected by Bcl-2"; *Cellular Immunology*, 250; pp. 31-39.
Van Der Weyden et al., (2002) "Tools for Targeted Manipulation of the Mouse Genome" *Physiological Genomics* 11; pp. 133-164.
Van Lent et al., (2009) "IL-7 enhances thymic human T cell development in "human immune system" Rag2-/-IL-2Rgammac-/-mice without affecting peripheral T cell homeostasis" *J Immunol*. 183(12):7645-55. doi: 10.4049/jimmunol.0902019.
Vaughan, Ashley M. et al; "Development of humanized mouse models to study human malaria parasite infection"; *Future Microbiology*, vol. 7, No. 5; (May 2012); pp. 657-665.
Verstegen et al. (2003) "Thrombopoietin is a major limiting factor for selective outgrowth of human umbilical cord blood cells in non-obese diabetic/severe combined immunodeficient recipient mice" *British Journal of Hematology* 122; pp. 837-846.
Vivier et al., (2008) "Functions of natural killer cells," *Nat Immunol*. 9(5):503-10. doi: 10.1038/ni1582.
Waldron-Lynch, et al. (2012) "Teplizumab induces human gut-tropic regulatory cells in humanized mice and patients"; Sci Transl Med. 4(118):118ra12; pp. 1-12.
Wall (1997) "Transgenic dairy cattle: genetic engineering on a large scale"; J Dairy Sci;80: pp. 2213-2224.
Watanabe (1997), "GM-CSF-mobilized peripheral blood CD34+ cells differ from steady-state bone marrow CD34+ cells in adhesion molecule expression"; *Bone Marrow Transplant*. 19(12): 1175-81.
Watanabe et al.; (1998) "Interleukin 7 Transgenic Mice Develop Chronic Colitis with Decreased Interleukin 7 Protein Accumulation in the Colonic Mucosa"; *J. Exp. Med.*, 187(3); pp. 389-402.
Watanabe Takeshi (2008) "Development of Humanized Mouse and Its Application"; Chemistry and Biology, vol. 46, No. 9, pp. 614-620 (Partial English translation attached).
Watanabe et al., (2009) "The analysis of the functions of human B and T cells in humanized NOD/shi-scid/gammac(null) (NOG) mice (hu-HSC NOG mice)," *Int Immunol*. 21(7):843-58. doi: 10.1093/intimm/dxp050. Epub Jun. 10, 2009.
Wei et al., "Transgenic expression of CSF-1 in CSF-1 receptor-expressing cells lead to macrophage activation, osteoporosis, and early death" *Journal of Leukocyte Biology*, 80:1445-1453 (Dec. 2006).
Weissenbach et al; (1980) "Two interferon mRNAs in human fibroblasts: In Vitro translation and D *Escherichia coli* cloning studies"; *Proc. Natl. Acad. Sci. USA*, 77(12); pp. 7152-7156.
Wendling, F. et al. (1994) "cMpl ligand is a humoral regulator of megakaryocytopoiesis," *Nature* 369:571-574.
Wheeler et al.; (2001) "Transgenic Technology and Applications in Swine"; *Theriogenology*, 56; pp. 1345-1369.
Wilmut (2003) "Dolly-her life and legacy"; Cloning Stem Cell 5; pp. 99-1 00.
Wiktor-Jedrzejczak, W. et al. (1990) "Total absence of colony-stimulating factor 1 in the macrophage-deficient osteopetrotic (op/op) mouse" *Proc. Natl Acad. Sci. USA* 87:4828-4832.
Williams, et al.; (1997) "IL-7 Overexpression in Transgenic Mouse Keratinocytes Causes a Lymphoproliferative Skin Disease Dominated by Intermediate TCR Cells"; *The Journal of Immunoloqy*, 159; pp. 3044-3056.

(56) References Cited

OTHER PUBLICATIONS

Willinger Tim; "A new flavor of the humanized mouse: The human IL-3/GM-CSF knock-in mouse"; IWHM2 2nd International Workshop on Humanized Mice, PowerPoint Presentation; Apr. 3-6, 2009; Sint Olofskapei/Amsterdam, NL; pp. 1-23.
Willinger, et al; "Human IL-3/GM-CSF knock-in mice support human alveolar macrophage development and human immune responses in the lung", PNAS 108(6); (Feb. 2011); pp. 2390-2395.
Willinger et al.; (2011) "Improving human hemato-lymphoid-system mice by cytokine knock-in gene replacement"; Trends in Immunology, 32(7); pp. 321-327.
Woodroofe et al.; (1992) "Long-Term Consequences of lnterleukin-6 Overexpression in Transgenic Mice"; DNA and Cell Bioloqy, 11(8); pp. 587-592.
Yaccoby et al., (1998) "Primary myeloma cells growing in SCID-hu mice: a model for studying the biology and treatment of myeloma and its manifestations" Blood. 92(8):2908-13.
Yaccoby and Epstein, (1999) "The proliferative potential of myeloma plasma cells manifest in the SCID-hu host" Blood. 94(10):3576-82.
Yajima et al., "A new humanized mouse model of Epstein-Barr virus infection that reproduces persistent infection, lymphoproliferative disorder, and cell-mediated and humoral immune responses," J Infect Dis. Sep. 1, 2008; 198(5):673-82. doi: 10.1086/590502.
Yamasaki et al.; (1988) "Cloning and Expression of the Human lnterleukin-6 (BSF-2/lFNβ 2) Receptor"; Science, 241; pp. 825-828.
Yanagimachi (2002) "Cloning: experience from the mouse and other animals"; Mol Cell Endocrinol. 187; pp. 241-248.
Yao et al. (2014) "CyTOF supports efficient detection of immune cell subsets from small samples"; J. of Immunological Methods 415; pp. 1-5.
Yasukawa et al.; (1987) "Structure and expression of human B cell stimulatory factor-2 (BSF-2/IL-6) gene"; The EMBO Journal, 6(10); pp. 2939-2945.
Yeung, Y.G. and Stanley, E.R. (2003) "Proteomic approaches to the analysis of early events in colony-stimulating factor-1 signal transduction," Mol. Cell. Proteomics 2:1143-1155.
Yoshihara, H. et al. "Thrombopoietin/MPL signaling regulates hematopoietic stem cell quiescence and interaction with the osteoblastic niche," Cell Stem Cell. Dec. 13, 2007; 1(6):685-97. doi: 10.1016/j.stem.2007.10.020. Epub Nov. 20, 2007.
Yoshida, H. et al. (1990) "The murine mutation osteopetrosis is in the coding region of the macrophage colony stimulating factor gene," Nature 345:442-444.
Young; et al. (2009) "Infectious disease: Tuberculosis", Eur. J. lmmunol, 39:1991-2058. U.S. Appl. No. 14/469,308.
Yu et al., "CSF-1 receptor structure/function in MacCsflr-/- macrophages: regulation of proliferation, differentiation, and morphology" Journal of Leukocyte Biology, 84: (Sep. 2008). pp. 852-863.
Yu et al (2017) "A novel humanized mouse model with significant improvement of class-switched, antigen-specific antibody production"; Blood. 129(8); pp. 959-969.
Zang, WP et al. "Transfer and Expression of Recombinant Human Thrombopoietin Gene in COS-7 Cells and Mice In Vivo", [Article in Chinese] Zhongguo Shi Yan Xue Ye Xue Za Zhi 9(1): (Mar. 2001), English Abstract.
Zang, W, et al. "Thrombopoietic effect of recombinant human thrombopoietin gene transferred to mice mediated by electric pulse on normal and experimental thrombocytopenia mice", [Article in Chinese] Zhonghua Xue Ye Xue Za Zhi. 22(3): (Mar. 2001), English Abstract.
Zhan et al., "The molecular classification of multiple myeloma"; Blood. Sep. 15, 2006; 108(6):2020-8. Epub May 25, 2006.
Zhao; et al."Thrombopoietin: a potential T-helper lymphocyte stimulator. Change in T-lymphocyte composition and blood cytokine levels in thrombopoietin eDNA transferred mice", Haematolgica (Jun. 1998), 83(6):572-573.
Zhou et al., (1997) "Transgenic Mice Overexpressing Human c-mpl Ligand Exhibit Chronic Thrombocytosis and Display Enhanced Recovery From 5-Fluorouracil or Antiplatelet Serum Treatment" Blood 89:1551-1559.
Zhou Hongxia, et al. (2009) "Developing tTA transgenic rats for inducible and reversible gene expression"; International Journal of Biological Sciences 5, pp. 171-181.
Zilberstein et al.; (1986) "Structure and expression of cDNA and genes for human interferon-beta-2; a distinct species inducible by growth-stimulatory cytokines"; The EMBO Journal, 5(10; pp. 2529-2537.
Houdebine Louis-Marie (2009) "Methods to Generate Transgenic Animals"; Genetic Engineering in Livestock: New Applications and Interdisciplinary Perspectives; pp. 31-48.
Patil et al.(2011) "Transgenic animals and drug development: A review"; Indian Journal of Public Health research & Development, vol. 2, No. 1; pp. 106-109.
U.S. Appl. No. 15/954,450, filed Apr. 16, 2018, Herndler-Brandstetter, Dietmar.
U.S. Appl. No. 15/980,602, filed May 15, 2018, Flavell, et al.
Bernier et al. (2001) "M-CSF Transgenic Mice: Role of M-CSF in Infection and Autoimmunity"; Exp. Toxic Pathology 53(2); pp. 165-173.
Doherty et al. (1999) "Infection of HIV-1 Transgenic Mice with Mycobacterium avium Induces the Expression of Infectious Virus Selectively from a Mac-1-Positive Host Cell Population"; The Journal of Immunology 163(3); pp. 1506-1515.
Jones et al (1995) "Antimicrobial Chemotherapy of Human Infection due to Listeria Monocytogenes"; Eur. J. Clin. Microbial. Infect. Dis.,14(3); pp. 165-175.
Nichterlein et al (1991) "Effect of various antibiotics on Listeria monocytogenes multiplying in L 929 cells"; Infection 19, Supplement 4; S234-S238.
U.S. Appl. No. 16/586,573, filed Sep. 27, 2019, Flavell, et al.
U.S. Appl. No. 16/672,042, filed Nov. 1, 2019, Stevens, et al.
Madan A., et al (1995) "Regulated basal, inducible, and tissue-specific human erythropoietin gene expression in transgenic mice requires multiple cis DNA sequences"; Blood, vol. 85, No. 10; pp. 2735-2741.
Brevini TA, et al. (2010) "No shortcuts to pig embryonic stem cells"; Theriogenology 74(4); pp. 544-550.
Cao Shanbo et al. (2009) "Isolation and culture of primary bovine embryonic stem cell colonies by a novel method"; Journal of Experimental Zoology, 311(5); pp. 368-376.
Herndler-Brandstetter D. et al. (2017) "Humanized mouse model supports development, function, and tissue residency of human natural killer cells"; Proc Natl Acad Sci U S A. 114(45); pp. E9626-E9634.
Kaushansky, et al (2014) "Of men in mice: the success and promise of humanized mouse models for human malaria parasite infections"; Cellular Microbiology, vol. 16, No. 5; pp. 602-611.
Paris DB and Stout TA (2010) "Equine embryos and embryonic stem cells: defining reliable markers of pluripotency"; Theriogenology 74(4); pp. 516-524.

\* cited by examiner

```
                           SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 1
ttgccggttt tccctttct c                                                    21

<210> SEQ ID NO 2
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 2
agggaaggcc gtggttgtc                                                      19

<210> SEQ ID NO 3
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 3
ccagcatcag tcccaagaag gcaact                                              26

<210> SEQ ID NO 4
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 4
tcagagtgtg ggcgaacaaa g                                                   21

<210> SEQ ID NO 5
<211> LENGTH: 20
<212> TYPE: DNA
<213> ORGANISM: Artificial sequence
<220> FEATURE:
<223> OTHER INFORMATION: synthetic polynucleotide
```

```
<400> SEQUENCE: 5
gtggcaaaag cagccttagc                                               20

<210> SEQ ID NO 6
<211> LENGTH: 28
<212> TYPE: DNA
<213> ORGANISM: Artificial sequence
<220> FEATURE:
<223> OTHER INFORMATION: synthetic polynucleotide

<400> SEQUENCE: 6
tcattccagg cccttcttat tgcatctg                                      28

<210> SEQ ID NO 7
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 7
ccccactcca ctggaatttg                                               20

<210> SEQ ID NO 8
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 8
gttcaaccac agccaggaaa g                                             21

<210> SEQ ID NO 9
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 9
agctacaact cattggcatc ctggcaa                                       27

<210> SEQ ID NO 10
<211> LENGTH: 197
<212> TYPE: DNA
<213> ORGANISM: Homo sapiens

<400> SEQUENCE: 10
aattagagag ttgactccta ataaatatga gactggggat gtctgtagct cattctgctc   60
tggagcccac caagaacgat agtcaattcc agaaaccgct atgaactcct tctccacaag  120
taagtgcagg aaatccttag ccctggaact gccagcggcg gtcgagccct gtgtgaggga  180
ggggtgtgtg gcccagg                                                 197

<210> SEQ ID NO 11
<211> LENGTH: 151
<212> TYPE: DNA
<213> ORGANISM: Homo sapiens

<400> SEQUENCE: 11
ttttaaagaa atatttatat tgtatttata taatgtataa atggttttta taccaataaa   60
tggcatttta aaaaattcag caactttgag tgtgtcacgc tcccgggctc gataactata  120
```

```
                                           -continued acggtcctaa ggtagcgact cgagataact t                            151

<210> SEQ ID NO 12
<211> LENGTH: 128
<212> TYPE: DNA
<213> ORGANISM: Homo sapiens

<400> SEQUENCE: 12
tatacgaagt tatcctaggt tggagctcct aagttacatc caaacatcct cccccaaatc   60
aataattaag cacttttat gacatgtaaa gttaaataag aagtgaaagc tgcagatggt   120
gagtgaga                                                            128
```

GENETICALLY MODIFIED NON-HUMAN ANIMALS AND METHODS OF USE THEREOF

CROSS REFERENCE TO RELATED APPLICATIONS

Pursuant to 35 U.S.C. § 119 (e), this application claims priority to the filing date of the U.S. Provisional Patent Application Ser. No. 61/722,437 filed Nov. 5, 2012; the full disclosure of which is herein incorporated by reference.

STATEMENT REGARDING FEDERALLY SPONSORED RESEARCH OR DEVELOPMENT

This invention was made with government support under grant number 5R01CA156689-04 awarded by the National Institutes of Health (NIH). The government has certain rights in the invention.

BACKGROUND OF THE INVENTION

The aim of biomedical research is to gain a better understanding of human physiology and to use this knowledge to prevent, treat or cure human diseases. Due to practical and ethical barriers to the experimentation on human subjects, many studies are conducted on small animal models, such as the mouse. Animal models of these human diseases are therefore needed.

For example, in the United States, around 20,000 patients are annually newly diagnosed with multiple myeloma (MM), a mostly incurable malignancy of antibody-secreting terminally differentiated B cells (Hideshima et al., 2007, Nat Rev Cancer. 7:585-98; Kuehl and Bergsagel, 2002, Nat Rev Cancer. 2:175-87). MINI is characterized by the infiltration of malignant plasma cells in the bone marrow (BM) and clinical manifestations include bone disease, hypercalcemia, cytopenia, renal dysfunction, and peripheral neuropathy (Hideshima et al., 2007, Nat Rev Cancer. 7:585-98; Kuehl and Bergsagel, 2002, Nat Rev Cancer. 2:175-87). In most cases, MM is preceded by a premalignant condition called monoclonal gammopathy of undetermined significance (MGUS) that affects around 3% of persons older than 50 years (Landgren et al., 2009, Blood 113:5412-7). Complex heterogeneous genetic abnormalities characterize MINI cells including changes in the karyotype as well as IgH translocations (Kuehl and Bergsagel, 2002, Nat Rev Cancer. 2:175-87; Zhan et al., 2006, Blood 108:2020-8). Plasma cell clones that are amplified in MGUS are thought to have genetic and phenotypic profiles similar to myelomatous plasma cells (Chng et al., 2005, Blood 106:2156-61; Fonseca et al., 2002, Blood 100:1417-24; Kaufmann et al., 2004, Leukemia. 18:1879-82). While mutations in cyclin D genes have been suggested to drive development of MM, the potential contributions of other factors have not been conclusively demonstrated (Bergsagel et al., 2005, Blood 106: 296-303). Nonetheless, heritable genetic alterations are not the sole determinants of the behavior of MM cells. Instead, resistance towards drugs and aberrant biological responses towards cytokines are strongly influenced by interactions with the microenvironment offering an opportunity to develop novel therapeutics.

Like many other tumors, MM is characterized by heterogeneous cell populations strongly interacting with non-malignant stroma cells that create a supportive environment (De Raeve and Vanderkerken, 2005, Histol Histopathol. 20:1227-50; Dhodapkar, 2009, Am J Hematol. 84:395-6). The BM microenvironment for MM cells consists of a diverse extracellular matrix (ECM) and of cellular components of both hematopoietic and non-hematopoietic origin. While the BM provides a protected environment for normal hematopoiesis, the interaction of MM cells with ECM proteins and accessory cells plays a crucial role in MM pathogenesis (De Raeve and Vanderkerken, 2005, Histol Histopathol. 20:1227-50; Dhodapkar, 2009, Am J Hematol. 84:395-6; Hideshima et al., 2007, Nat Rev Cancer. 7:585-98). Stroma cells, myeloid cells, osteoclasts, and osteoblasts produce growth factors such as interleukin 6 (IL-6), B-cell activating factor (BAFF), fibroblast growth factor, and stroma cell-derived factor 1a that activate signal pathways mediating migration, survival, and growth of MM cells. In particular, IL-6 produced by stroma cells, osteoclasts, and myeloid cells seems to be a crucial factor in the early stages and for pathogenesis of MM (De Raeve and Vanderkerken, 2005, Histol Histopathol. 20:1227-50). Similarly, upon interaction with MINI cells, osteoclasts and dendritic cells produce BAFF and/or a proliferation-inducing ligand (APRIL) providing anti-apoptotic signals that also increase drug resistance (De Raeve and Vanderkerken, 2005, Histol Histopathol. 20:1227-50; Kukrej a et al., 2006, J Exp Med. 203:1859-65).

The major events in cancer pathogenesis—uncontrolled proliferation, survival and spread of the malignant cells—depend on specific combinations of supportive cell types and soluble factors present in microenvironmental niches. Mouse models play an important role in characterizing key aspects of the driving forces of malignant transformation and disease in humans. However, they rarely represent the genetic complexity and clinicopathologic characteristics of human disease. While xenotransplantation of human tumors into immunocompromised mice has been extensively employed, reliable engraftment has typically been feasible only with highly aggressive tumors or cell lines.

The best models currently available to grow human tumor cells are severely immunodeficient mice that lack B cells, T cells, and NK cells. In the case of MM, engraftment of primary myeloma cells into these mice has been unsuccessful, but primary myeloma cells are able to engraft human fetal bone pieces upon co-transplantation into immunocompromised mice (Yaccoby et al., 1998, Blood 92:2908-13). In this model MM cells are found in the human bone, but are not detected in the mouse bone or in the periphery demonstrating high residual xenorejection and a need for the human BM microenvironment (Yaccoby et al., 1998, Blood 92:2908-13; Yaccoby and Epstein, 1999, Blood 94:3576-82). Proving its potential as in vivo model for MM, it was recently demonstrated that NOD/Scid/$\gamma c^{-/-}$ mice allow the engraftment of several MM cell lines (Dewan et al., 2004, Cancer Sci. 95:564-8; Miyakawa et al., 2004, Biochem Biophys Res Commun. 313:258-62). However, even those mouse models with low xenorejection have constricted growth environments by virtue of a large number of factors that do not cross species barriers but are essential to support growth and survival of transformed cells (Manz, 2007). In vivo models that allow us to probe the complex pathogenic interplay between the tumor and its environment will be essential to design new drugs and therapies.

Therefore there is an unmet need to develop humanized non-human animals and methods to reliably grow and study human hematopoietic cells, including primary human hematopoietic tumor cells in mice. The present invention addresses these unmet needs in the art.

SUMMARY OF THE INVENTION

Genetically modified non-human animals are provided that may be used to model human hematopoietic cell development, function, or disease. The genetically modified non-human animals comprise a nucleic acid encoding human IL-6 operably linked to an IL-6 promoter. In some instances, the genetically modified non-human animal expressing human IL-6 also expresses at least one of human M-CSF, human IL-3, human GM-CSF, human SIRPa or human TPO. In some instances, the genetically modified non-human animal is immunodeficient. In some such instances, the genetically modified non-human animal is engrafted with healthy or diseased human hematopoietic cells. Also provided are methods for using the subject genetically modified non-human animals in modeling human hematopoietic cell development, function, and/or disease, as well as reagents and kits thereof that find use in making the subject genetically modified non-human animals and/or practicing the subject methods.

In various aspects of the invention, a genetically modified non-human animal is provided, the genetically modified non-human animal comprising a genome comprising a nucleic acid encoding human IL-6 operably linked to an IL-6 promoter, wherein the animal expresses human IL-6 polypeptide under the regulatory control of the IL-6 promoter. In some embodiments, the genetically modified non-human animal does not express the animal's native IL-6.

In some embodiments, the genetically modified non-human animal is a rodent. In some embodiments, the non-human animal is a mouse. In some such embodiments, the IL-6 promoter to which the nucleic acid encoding human IL-6 is operably linked is the mouse IL-6 promoter, and the human IL-6 gene is operably linked to the mouse IL-6 promoter at the mouse IL-6 locus.

In some embodiments, the genetically modified non-human animal further comprises one or more additional nucleic acids selected from a nucleic acid encoding human SIRPa under the control of a SIRPa promoter; a nucleic acid encoding human M-CSF operably linked to an M-CSF promoter, wherein the animal expresses human M-CSF; a nucleic acid encoding human IL-3 operably linked to an IL-3 promoter, wherein the animal expresses human IL-3; a nucleic acid encoding human GM-CSF operably linked to a GM-CSF promoter, wherein the animal expresses human GM-CSF; and a nucleic acid encoding human TPO operably linked to a TPO promoter, wherein the animal expresses human TPO. In some embodiments, the promoter is the human promoter for the gene. In other embodiments, the promoter is the non-human animal promoter for the gene. In some embodiments, the genetically modified non-human animal expresses the animal's corresponding native protein. In other embodiments, the genetically modified non-human animal does not express the animal's corresponding native protein.

In some embodiments, the genetically modified non-human animal is immunodeficient for the non-human animal immune system. In some such embodiments, the immunodeficient genetically modified non-human animal does not express a recombination activating gene (RAG). In some such embodiments the immunodeficient genetically modified non-human animal does not express the IL2 receptor gamma chain (IL2rg, or "γc"). In some such embodiments the immunodeficient genetically modified non-human animal does not express either a RAG (e.g. RAG1, RAG2) or IL2rg.

In some embodiments, the immunodeficient genetically modified non-human animal is engrafted with human hematopoietic cells to form a genetically modified and engrafted non-human animal. In one embodiment, the human hematopoietic cells are selected from human umbilical cord blood cells, human fetal liver cells, and cells of a human hematopoietic cell line. In one embodiment, the human hematopoietic cells are CD34+ progenitor cells. In one embodiment, the human hematopoietic cells are cancer cells. In certain embodiments, the cancer cells are human multiple myeloma cells.

In some embodiments, the genetically modified and engrafted animal gives rise to a human cell selected from a CD34+ cell, a hematopoietic stem cell, a hematopoeitic cell, a myeloid precursor cell, a myeloid cell, a dendritic cell, a monocyte, a granulocyte, a neutrophil, a mast cell, a thymocyte, a T cell, a B cell, a plasma cell, a platelet, and a combination thereof. In one embodiment, the human cell is present at 1 month, at 2 months, at 3 months, at 4 months, 5 months, 6 months, 7 months, 8 months, 9 months, 10 months, 11 months, or 12 months after engraftment.

In some embodiments, the genetically modified and engrafted animal gives rise to a human hemato-lymphoid system that comprises human hematopoietic stem and progenitor cells, human myeloid progenitor cells, human myeloid cells, human dendritic cells, human monocytes, human granulocytes, human neutrophils, human mast cells, human thymocytes, human T cells, human B cells, human plasma cells, and human platelets. In one embodiment, the human hemato-lymphoid system is present at 4 months, 5 months, 6 months, 7 months, 8 months, 9 months, 10 months, 11 months, or 12 months after engraftment.

In some aspects of the invention, methods are provided for generating a non-human animal engrafted with human hematopoietic cells. In some embodiments, methods are provided for generating an animal model of human immune cell development and function. In certain embodiments, methods are provided for generating an animal model of human B cell development and function.

In some embodiments, the methods comprise transplanting a population of human hematopoietic cells to a genetically modified non-human animal that is immunodeficient and expresses a nucleic acid encoding human IL-6 operably linked to an IL-6 promoter. In some embodiments, the animal does not express native IL-6. In some embodiments, the IL-6 promoter is the non-human animal IL-6 promoter and the human IL-6 gene is operably linked to the non-human animal IL-6 promoter at the non-human animal IL-6 locus. In some embodiments, the non-human animal is a rodent. In some such embodiments, the non-human animal is a mouse. As such, in some embodiments, the IL-6 promoter to which the nucleic acid encoding human IL-6 is operably linked is the mouse IL-6 promoter, and the human IL-6 gene is operably linked to the mouse IL-6 promoter at the mouse IL-6 locus.

In some embodiments, the transplanted population of hematopoietic cells comprises CD34+ cells. In some embodiments, the transplanted population of hematopoietic cells comprises cancer cells. In some embodiments, the transplanted population of cancer cells comprises multiple myeloma cells. In some embodiments, the transplanting comprises intrafemoral and/or intratibial injection.

In some embodiments, the immunodeficient, genetically modified animal expresses at least one additional human nucleic acid selected from the group consisting of a nucleic acid encoding human SIRPa operably linked to a SIRPa promoter; a nucleic acid encoding human M-CSF operably linked to a M-CSF promoter; a nucleic acid encoding human IL-3 operably linked to an IL-3 promoter; a nucleic acid encoding human GM-CSF operably linked to a GM-CSF promoter; and a nucleic acid encoding human TPO operably linked to a TPO promoter.

In some aspects of the invention, engrafted, genetically modified non-human animals expresses a nucleic acid encoding human IL-6 operably linked to an IL-6 promoter are provided, these engrafted, non-human animals having been prepared according to the methods described herein or as known in the art. In some embodiments, the engrafted, genetically modified non-human animal is an animal model of human B cell development and differentiation In various embodiments, methods are provided that encompass the use of human hematopoietic cell-engrafted, genetically modified non-human animals of the subject disclosure. These methods include, for example, methods for the in vivo evaluation of the growth and differentiation of hematopoietic and immune cells, methods for the in vivo evaluation of human hematopoiesis, methods for the in vivo evaluation of cancer cells, methods for the in vivo assessment of an immune response, methods for the in vivo evaluation of vaccines and vaccination regimens, methods for the use in testing the effect of agents that modulate cancer cell growth or survival, methods for the in vivo evaluation of a treatment of cancer, and methods for the in vivo production and collection of immune mediators, including human antibodies, and for use in testing the effect of agents that modulate hematopoietic and immune cell function. For example, in some embodiments, methods are provided for screening a candidate agent for the ability to treat a hematopoietic cancer. In some embodiments, the method comprises contacting a genetically modified non-human animal of the present disclosure that has been engrafted with human hematopoietic cancer cells with a candidate agent, and comparing the viability and/or proliferative rate of human hematopoietic cancer cells in the contacted engrafted, genetically modified non-human animal to the human hematopoietic cancer cells in a similarly engrafted, genetically modified non-human animal that is not contacted with candidate agent, wherein a decrease in the viability and/or rate of proliferation of the human hematopoietic cancer cells in the contacted engrafted, non-human animal indicates that the candidate agent will treat a hematopoietic cancer. These and other methods will be apparent to the ordinarily skilled artisan from the disclosure herein.

BRIEF DESCRIPTION OF THE DRAWINGS

The following detailed description of preferred embodiments of the invention will be better understood when read in conjunction with the appended drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. For the purpose of illustrating the invention, there are shown in the drawings embodiments which are presently preferred. It should be understood, however, that the invention is not limited to the precise arrangements and instrumentalities of the embodiments shown in the drawings. Included in the drawings are the following figures.

DETAILED DESCRIPTION

Figure 1:
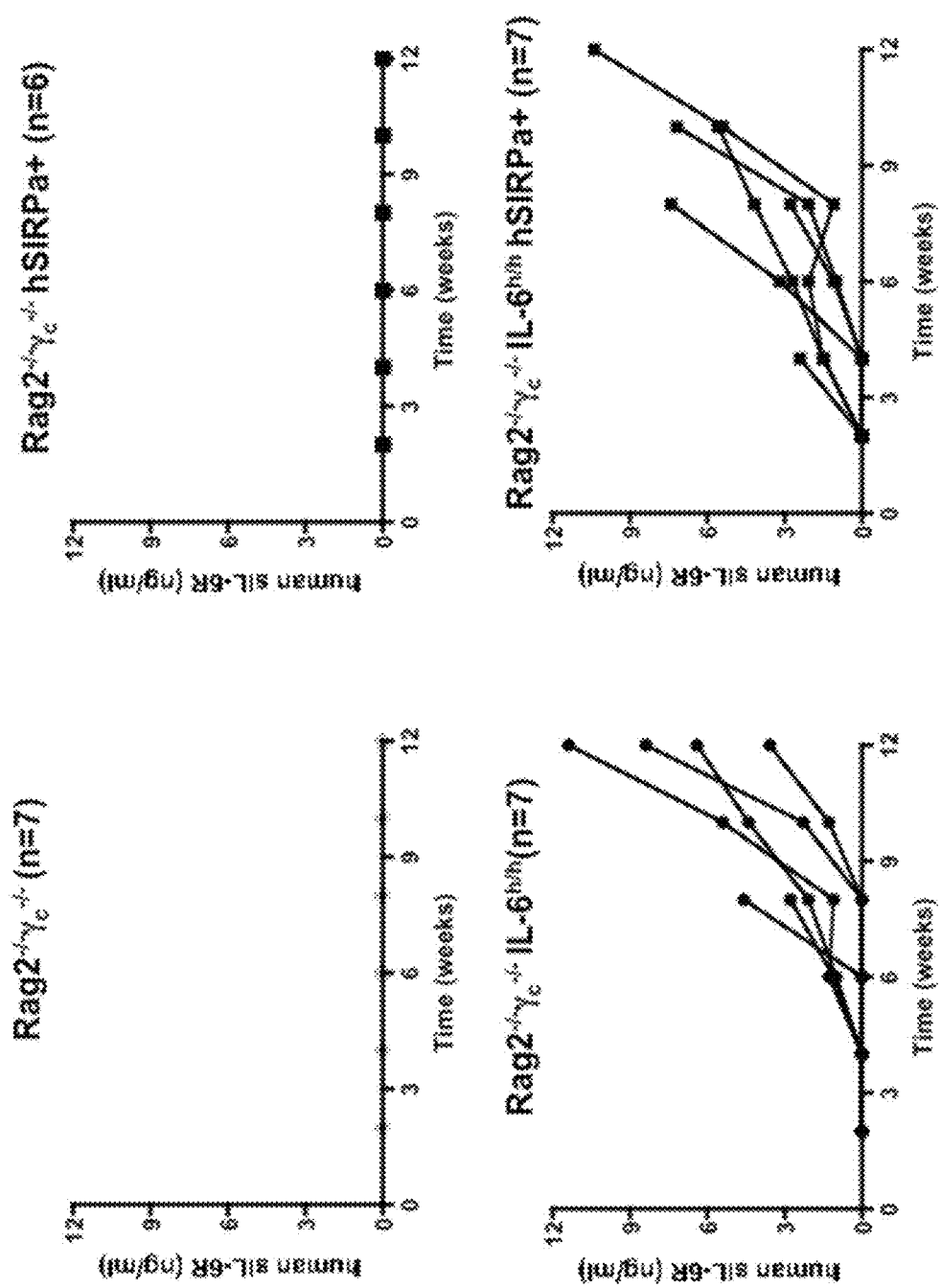
FIG. 1 is a set of graphs depicting the results of experiments demonstrating the engraftment of INA-6 cells in human IL-6 knock-in mice. Soluble IL-6R levels were measured in mice of the indicated genotypes transplanted with $5\times10^6$ INA-6 cells intravenously. N indicates the number of transplanted mice per group.

Genetically modified non-human animals are provided that may be used to model human hematopoietic cell development, function, or disease. The genetically modified non-human animals comprise a nucleic acid encoding human IL-6 operably linked to an IL-6 promoter. In some embodiments, the genetically modified non-human animal expressing human IL-6 also expresses at least one of human M-CSF, human IL-3, human GM-CSF, human SIRPa or human TPO. The invention also relates to methods of generating and methods of using the genetically modified non-human animals described herein. In some embodiments, the genetically modified non-human animal is a mouse. In some embodiments, the genetically modified non-human animal described herein is engrafted with human hematopoietic cells, including either normal or neoplastic cells, or combinations thereof. In some embodiments, the genetically modified non-human animal described herein is engrafted with human multiple myeloma (MM) cells. In various embodiments, the human hematopoietic cell engrafted, genetically modified non-human animals of the invention are useful for the in vivo evaluation of the growth and differentiation of hematopoietic and immune cells, for the in vivo evaluation of human hematopoiesis, for the in vivo evaluation of cancer cells, for the in vivo assessment of an immune response, for the in vivo evaluation of vaccines and vaccination regimens, for the use in testing the effect of agents that modulate cancer cell growth or survival, for the in vivo evaluation of a treatment of cancer, for the in vivo production and collection of immune mediators, including human antibodies, and for use in testing the effect of agents that modulate hematopoietic and immune cell function.

These and other objects, advantages, and features of the invention will become apparent to those persons skilled in the art upon reading the details of the compositions and methods as more fully described below.

Definitions

Unless defined otherwise, all technical and scientific terms used herein have the same meaning as commonly understood by one of ordinary skill in the art to which this invention belongs. Such terms are found defined and used in context in various standard references illustratively including J. Sambrook and D. W. Russell, Molecular Cloning: A Laboratory Manual, Cold Spring Harbor Laboratory Press; 4th Ed., 2012; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, includes those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, includes an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Constitutive" expression includes a state in which a gene product is produced in a living cell under most or all physiological conditions of the cell.

A "coding region" of a gene includes the nucleotide residues of the coding strand of the gene and the nucleotides of the non-coding strand of the gene which are homologous with or complementary to, respectively, the coding region of an mRNA molecule which is produced by transcription of the gene. A "coding region" of a mRNA molecule also includes the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

A "disease" includes a state of health of an animal wherein the animal cannot maintain homeostasis, and wherein if the disease is not ameliorated then the animal's health continues to deteriorate.

In contrast, a "disorder" in an animal includes a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound includes that amount of compound which is sufficient to provide a beneficial effect to the subject to which the compound is administered. An "effective amount" of a delivery vehicle includes that amount sufficient to effectively bind or deliver a compound.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" includes any material from or produced inside an organism, cell, tissue or system.

As used herein, the term "exogenous" includes any material introduced from or produced outside an organism, cell, tissue or system.

The terms "expression construct" and "expression cassette" as used herein include a double-stranded recombinant DNA molecule containing a desired nucleic acid human coding sequence and containing one or more regulatory elements necessary or desirable for the expression of the operably linked coding sequence.

As used herein, the term "fragment," as applied to a nucleic acid or polypeptide, includes a subsequence of a larger nucleic acid or polypeptide. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between). A "fragment" of a polypeptide can be at least about 15 nucleotides in length; for example, at least about 50 amino acids to about 100 amino acids; at least about 100 to about 500 amino acids, at least about 500 to about 1000 amino acids, at least about 1000 amino acids to about 1500 amino acids; or about 1500 amino acids to about 2500 amino acids; or about 2500 amino acids (and any integer value in between).

As used herein, the terms "gene" and "recombinant gene" includes nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Homologous" as used herein, includes the subunit sequence similarity between two polymeric molecules, e.g. between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g. if half (e.g., five positions in a polymer ten subunits in length) of the positions in two compound sequences are homologous then the two sequences are 50% homologous, if 90% of the positions, e.g. 9 of 10, are matched or homologous, the two sequences share 90% homology. By way of example, the DNA sequences 5'-ATTGCC-3' and 5'-TATGGC-3' share 50% homology.

The terms "human hematopoietic stem and progenitor cells" and "human HSPC" as used herein, include human self-renewing multipotent hematopoietic stem cells and hematopoietic progenitor cells.

"Inducible" expression includes a state in which a gene product is produced in a living cell in response to the presence of a signal in the cell.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

The term "operably linked" as used herein includes a polynucleotide in functional relationship with a second polynucleotide, e.g. a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

The term "polynucleotide" as used herein includes a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and include a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term includes both short chains, which also commonly are referred to in the art as peptides, oligopeptides and oligomers, for example, and to longer chains, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. The term "peptide" typically refers to short polypeptides. The term "protein" typically refers to large polypeptides.

The term "progeny" as used herein includes a descendent or offspring and includes the differentiated or undifferentiated decedent cell derived from a parent cell. In one usage, the term progeny includes a descendent cell which is genetically identical to the parent. In another use, the term progeny includes a descendent cell which is genetically and phenotypically identical to the parent. In yet another usage, the term progeny includes a descendent cell that has differentiated from the parent cell.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "recombinant polypeptide" includes one which is produced upon expression of a recombinant polynucleotide.

The term "regulatory element" as used herein includes a nucleotide sequence which controls some aspect of the expression of nucleic acid sequences. Exemplary regulatory elements illustratively include an enhancer, an internal ribosome entry site (IRES), an intron; an origin of replication, a polyadenylation signal (pA), a promoter, an enhancer, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The term "specifically binds," as used herein with respect to an antibody, includes an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. As another example, an antibody that specifically binds to an antigen may also bind to different allelic forms of the antigen. However, such cross reactivity does not itself alter the classification of an antibody as specific.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "synthetic antibody" as used herein includes an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Variant" as the term is used herein, includes a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

The term "genetically modified" includes an animal, the germ cells of which comprise an exogenous human nucleic acid or human nucleic acid sequence. By way of non-limiting examples a genetically modified animal can be a transgenic animal or a knock-in animal, so long as the animal comprises a human nucleic acid sequence.

As used herein, the term "transgenic animal" includes an animal comprising an exogenous human nucleic acid sequence integrated into the genome of the animal.

As used herein, by "knock-in" "knock in" or "knockin" includes a genetic modification that is targeted to a particular chromosomal locus of the non-human animal genome and inserts a nucleic acid of interest into that targeted locus. In some instances, the genetic modification replaces the genetic information encoded at the chromosomal locus in the non-human animal with a different DNA sequence.

Genetically Modified Non-Human Animals

In some aspects of the invention, a genetically modified non-human animal that expresses human IL-6 is provided. By human IL-6 (hIL6) it is meant the 184 amino acid protein the sequence for which is described at, e.g, Genbank Accession Nos. NM_000600.3 and NP_000591.1. Human IL-6 is a secreted protein that is produced by, for example, T cells, B cells, monocytes, macrophages, fibroblasts, keratinocytes, endothelial cells and myeloma cells. IL-6 acts through a cell surface heterodimeric receptor complex comprising a binding subunit (IL-6R) and a signal transducing subunit (gp130). gp130 is a common component of other receptors, such the ones for IL-11, IL-27, LIF, whereas the IL-6R is predominantly restricted to hepatocytes, monocytes, activated B cells, resting T cells and myeloma cell lines. IL-6 plays a central role in hematopoiesis, in immune responses and in acute phase reactions, having been shown to be an important factor for the final maturation of B cells into antibody secreting cells (ASC), especially for the expansion of plasmablasts during the germinal center reaction in the T-dependent (TD) antibody response. IL-6 is required for T cell proliferation in vitro and for generation of cytotoxic T cells (CTL) in vivo, making them more responsive to IL-2.

In some aspects of the invention, the genetically modified non-human animal that expresses human IL-6 also expresses at least one additional human protein selected from human M-CSF, human IL-3, human GM-CSF, human TPO, and human SIRPa, or any combination thereof. In other words, the non-human animal that expresses human IL-6 may express one, two three, four or all five of the human proteins selected from hM-CSF, hIL-3, hGM-CSF, hTPO, and hSIRPa. Genetically modified non-human animals that express hM-CSF, hIL-3, hGM-CSF, hTPO, and/or hSIRPa on which the subject non-human animals may be designed or from which the subject non-human animals may be generated are well known in the art, and are discussed in greater detail in, for example, US Application No. US 2013/0042330 and Rathinam et al. 2011, Blood 118:3119-28, disclosing knock-in mice that express human M-CSF; U.S. Pat. No. 8,541,646 and Willinger et al. 2011, Proc Natl Acad Sci USA, 108:2390-2395, disclosing knock-in mice that express human IL-3 and human GM-CSF; U.S. Pat. No. 8,541,646 and Rongvaux et al. 2011, Proc Natl Acad Sci USA, 108:2378-83, disclosing knock-in mice that express human TPO; and PCT Application No. WO 2012/040207 and Strowig et al. 2011, Proc Natl Acad Sci USA 108(32): 13218-13223, disclosing transgenic mice that express human Sirpa; the full disclosures of which are incorporated herein by reference.

In various embodiments, the nucleic acid encoding the human protein is operatively linked to one or more regulatory sequences in a manner which allows for transcription of the nucleic acid into mRNA and translation of the mRNA into the human protein. The term "regulatory sequence" is art-recognized and intended to include promoters, enhancers and other expression control elements (e.g., polyadenylation signals). Such regulatory sequences are known to those skilled in the art and are described in 1990, Goeddel, Gene Expression Technology: Methods in Enzymology 185, Academic Press, San Diego, Calif. In one embodiment, the human nucleic acid is expressed by the native regulatory elements of the human nucleic acid. In another embodiment, the human nucleic acid is expressed by the native regulatory elements of the corresponding nucleic acid of the non-human host animal.

Thus, in some embodiments, the nucleic acid encoding human IL-6 is operably linked to the non-human animal's IL-6 promoter. In other embodiments, the nucleic acid encoding human IL-6 is operably linked to the human IL-6 promoter. As another example, in some embodiments, the nucleic acid encoding human M-CSF is operably linked to the animal's M-CSF promoter. In other embodiments, the nucleic acid encoding human M-CSF is operably linked to the human M-CSF promoter. As a third example, in some embodiments, the nucleic acid encoding human IL-3 is operably linked to the animal's IL-3 promoter. In other embodiments, the nucleic acid encoding human IL-3 is operably linked to the human IL-3 promoter. As a fourth example, in some embodiments, the nucleic acid encoding human GM-CSF is operably linked to the animal's GM-CSF promoter. In other embodiments, the nucleic acid encoding human GM-CSF is operably linked to the human GM-CSF promoter. As a fifth example, in some embodiments, the nucleic acid encoding human TPO is operably linked to the animal's TPO promoter. In other embodiments, the nucleic acid encoding human TPO is operably linked to the human TPO promoter.

The skilled artisan will understand that the genetically modified animals of the invention include genetically modified animals that express at least one human nucleic acid from a promoter. Nonlimiting examples of ubiquitously expressed promoters useful in the invention include, but are not limited to, DNA pol II promoter, PGK promoter, ubiquitin promoter, albumin promoter, globin promoter, ovalbumin promoter, SV40 early promoter, the Rous sarcoma virus (RSV) promoter, retroviral LTR and lentiviral LTR, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and a CMV (cytomegalovirus) promoter. Promoter and enhancer expression systems useful in the invention also include inducible and/or tissue-specific expression systems. Non-limiting examples of tissue-specific promoters useful in the expression construct of the compositions and methods of the invention include a promoter of a gene expressed in the hematopoietic system, such as an IL-6 promoter, a M-CSF promoter, an IL-3 promoter, a GM-CSF promoter, a SIRPA promoter, a TPO promoter, an IFN-f3 promoter, a Wiskott-Aldrich syndrome protein (WASP) promoter, a CD45 (also called leukocyte common antigen) promoter, a Flt-1 promoter, an endoglin (CD105) promoter and an ICAM-2 (Intracellular Adhesion Molecule 2) promoter. These and other promoters useful in the compositions and methods of the invention are known in the art as exemplified in Abboud et al. (2003, J. Histochem & Cytochem. 51:941-949), Schorpp et al. (1996, NAR 24:1787-1788), McBurney et al. (1994, Devel. Dynamics, 200:278-293) and Majumder et al. (1996, Blood 87:3203-3211). Further to comprising a promoter, one or more additional regulatory elements, such as an enhancer element or intron sequence, is included in various embodiments of the invention. Examples of enhancers useful in the compositions and methods of the invention include, but are not limited to, a cytomegalovirus (CMV) early enhancer element and an SV40 enhancer element. Examples of intron sequences useful in the compositions and methods of the invention include, but are not limited to, the beta globin intron or a generic intron. Other additional regulatory elements useful in some embodiments of the invention include, but are not limited to, a transcription termination sequence and an mRNA polyadenylation (pA) sequence.

The skilled artisan will also appreciate that in addition to the naturally occurring human nucleic acid and amino acid sequences, the terms human nucleic acid and human amino acid encompass variants of human nucleic acid and amino acid sequences as well. As used herein, the term "variant" defines either an isolated naturally occurring genetic mutant of a human or a recombinantly prepared variation of a human, each of which contain one or more mutations compared with the corresponding wild-type human. For example, such mutations can be one or more amino acid substitutions, additions, and/or deletions. The term "variant" also includes non-human orthologues. In some embodiments, a variant polypeptide of the present invention has at least 90%, 91%, 92%, 93%, 94%, 95%, 96%, 97%, 98% or 99% identity to a wild-type human polypeptide.

The percent identity between two sequences is determined using techniques as those described elsewhere herein. Mutations can be introduced using standard molecular biology techniques, such as site-directed mutagenesis and PCR-mediated mutagenesis. One of skill in the art will recognize that one or more amino acid mutations can be introduced without altering the functional properties of human proteins.

Conservative amino acid substitutions can be made in human proteins to produce human protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, methylhistidine, and ornithine.

Human variants are encoded by nucleic acids having a high degree of identity with a nucleic acid encoding a wild-type human. The complement of a nucleic acid encoding a human variant specifically hybridizes with a nucleic acid encoding a wild-type human under high stringency conditions. Nucleic acids encoding a human variant can be isolated or generated recombinantly or synthetically using well-known methodology.

In some embodiments, the genetically modified non-human animal that expresses a human nucleic acid sequence also expresses the corresponding non-human animal nucleic acid sequence. For example, and as described in greater detail below, in certain embodiments, the human nucleic acid sequence is randomly integrated into the genome of the non-human animal, e.g. such that the animal comprises the exogenous human nucleic acid sequence at a locus other than the non-human animal locus encoding the corresponding non-human animal protein. In other embodiments, the genetically modified non-human animal that expresses a human nucleic acid sequence does not express the corresponding non-human animal nucleic acid sequence. For example, and as described in greater detail below, in certain embodiments, the nucleic acid encoding the human protein is introduced into the animal so as to replace genomic material encoding the corresponding non-human animal protein, rendering the animal null for the corresponding non-human animal gene and deficient for the corresponding non-human animal protein. In other words, the non-human animal is a "knock-in" for the human gene.

Thus, in some embodiments, the genetically modified non-human animal that expresses human IL-6 also expresses non-human animal IL-6. In other embodiments, the genetically modified non-human animal that expresses human IL-6 does not express non-human animal IL-6. As a second example, in some embodiments, the genetically modified non-human animal that expresses human M-CSF also expresses non-human animal M-CSF. In other embodiments, the genetically modified non-human animal that expresses human M-CSF does not express non-human animal M-CSF. As a third example, in some embodiments, the genetically modified non-human animal that expresses human IL-3 also expresses non-human animal IL-3. In other embodiments, the genetically modified non-human animal that expresses human IL-3 does not express non-human animal IL-3. As a fourth example, in some embodiments, the genetically modified non-human animal that expresses human GM-CSF also expresses non-human animal GM-CSF. In other embodiments, the genetically modified non-human animal that expresses human GM-CSF does not express non-human animal GM-CSF. As a fifth example, in some embodiments, the genetically modified non-human animal that expresses human TPO also expresses non-human animal TPO. In other embodiments, the genetically modified non-human animal that expresses human TPO does not express non-human animal TPO.

In some embodiments, the subject genetically modified animal is immunodeficient. By "immunodeficient," it is meant that the non-human animal is deficient in one or more aspects of its native immune system, e.g the animal is deficient for one or more types of functioning host immune cells, e.g. deficient for non-human B cell number and/or function, non-human T cell number and/or function, non-human NK cell number and/or function, etc.

As one example, the immunodeficient animal may have severe combined immune deficiency (SCID). SCID refers to a condition characterized by the absence of T cells and lack of B cell function. Examples of SCID include: X-linked SCID, which is characterized by gamma chain gene mutations or loss of the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+), and Prkdc$^{scid}$ mutations (Bosma et al. (1989, Immunogenetics 29:54-56) and the lymphocyte phenotype T(−), B(−), lymphopenia, and hypoglobulinemia. As such, in some embodiments, the genetically modified immunodeficient non-human animal has one or more deficiencies selected from an IL2 receptor gamma chain deficiency, an ADA gene mutation, an IL7R mutation, a CD3 mutation, a RAG1 and/or RAG2 mutation, an Artemis mutation, a CD45 mutation, and a Prkdc mutation.

The subject genetically modified non-human animal may be any non-human mammal animal, for example, laboratory animals, domestic animals, livestock, etc., that is genetically modified to comprise human IL-6 coding sequence operably linked to an IL-6 promoter, e.g., species such as murine, rodent, canine, feline, porcine, equine, bovine, ovine, non-human primates, etc.; for example, mice, rats, rabbits, hamsters, guinea pigs, cattle, pigs, sheep, goats, and other transgenic animal species, particularly-mammalian species, as known in the art. In certain embodiments, the subject genetically modified animal is a mouse, a rat or a rabbit.

In one embodiment, the non-human animal is a mammal. In some such embodiments, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae.

In one embodiment, the subject genetically modified non-human animal is a rat. In one such embodiment, the rat is selected from a Wistar rat, an LEA strain, a Sprague Dawley strain, a Fischer strain, F344, F6, and Dark Agouti. In one another embodiment, the rat strain is a mix of two or more strains selected from the group consisting of Wistar, LEA, Sprague Dawley, Fischer, F344, F6, and Dark Agouti.

In another embodiment, the subject genetically modified animal is a mouse, e.g. a mouse of a C57BL strain (e.g. C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola, etc.); a mouse of the 129 strain (e.g. 129P1, 129P2, 129P3,129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2); a mouse of the BALB strain; e.g., BALB/c; and the like. See, e.g., Festing et al. (1999) Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In yet another embodiment, the mouse is a mix of a BALB strain and another aforementioned strain.

Thus, for example, in some embodiments, the subject genetically modified non-human animal is an immunodeficient mouse deficient in B cell number and/or function, and/or T cell number and/or function, and/or NK cell number and/or function (for example, due to an IL2 receptor gamma chain deficiency (i.e., $\gamma_c^{-/-}$) and/or a RAG deficiency), and having a genome that comprises a human nucleic acid, e.g. a nucleic acid encoding human IL-6, hM-CSF, hIL-3, hGM-CSF, hTPO, and/or hSIRPa, operably linked to its corresponding promoter, e.g. a M-CSF, IL-3, GM-CSF, TPO or SIRPa promoter, respectively, wherein the animal expresses the encoded human protein(s).

In certain specific embodiments, the subject genetically modified animal is an immunodeficient mouse comprising a nucleic acid encoding human IL-6 operably linked to an IL-6 promoter at the mouse IL-6 locus, and a nucleic acid encoding human SIRPa operably linked to the human SIRPa promoter randomly integrated into the genome of the non-human animal (i.e., the mouse expresses mouse SIRPa), i.e. an immunodeficient hIL6, hSirpa mouse, e.g. a Rag2$^{-/-}$ IL2rg$^{-/-}$ IL-6$^{h/+}$ hSIRPa$^+$ mouse or a Rag2$^{-/-}$IL2rg$^{-/-}$ IL-6$^{h/h}$ hSIRPa$^-$ mouse. In some such embodiments, the mouse further comprises a nucleic acid encoding a human M-CSF operably linked to an M-CSF promoter, a nucleic acid encoding human IL-3 operably linked to an IL-3 promoter, a nucleic acid encoding human GM-CSF operably linked to a GM-CSF promoter, and a nucleic acid encoding human TPO operably linked to a TPO promoter, i.e. an immunodeficient hIL-6, hSirpa, hM-CSF, hIL-3, hGM-CSF, hTPO mouse, e.g. a Rag2$^{-/-}$IL2rg$^{-/-}$ IL-6$^{h/+}$ M-CSF$^{h/+}$ IL-3$^{h/+}$ GM-CSF$^{h/+}$ TPO$^{h/+}$ hSIRPa$^+$ mouse, a Rag2$^{-/-}$ IL2rg$^{-/-}$ IL-6$^{h/+}$ M-CSF$^{h/h}$ IL-3$^{h/h}$ GM-CSF$^{h/h}$ TPO$^{h/h}$ hSIRPa$^1$ mouse.

In certain specific embodiments, the subject genetically modified animal is an immunodeficient mouse comprising a nucleic acid encoding human IL-6 operably linked to an IL-6 promoter and deficient for mouse IL-6, a nucleic acid encoding human SIRPa operably linked to the human SIRPa promoter randomly integrated into the genome of the non-human animal (i.e., the mouse still expresses mouse SIRPa), a nucleic acid encoding human M-CSF operably linked to an M-CSF promoter and deficient for mouse M-CSF, a nucleic acid encoding human IL-3 operably linked to an IL-3 promoter and deficient for mouse IL-3, a nucleic acid encoding human GM-CSF operably linked to a GM-CSF promoter and deficient for mouse GM-CSF, and a nucleic acid encoding human TPO operably linked to a TPO promoter and deficient for mouse TPO, i.e. a Rag2$^{-/-}$ IL2rg$^{-/-}$ IL-6$^{h/h}$ M-CSF$^{h/h}$ IL-3$^{h/h}$ GM-CSF$^{h/h}$ TPO$^{h/h}$, hSIRPa+ mouse.

Methods of Making Genetically Modified Non-Human Animals

The subject genetically modified non-human animals may be generated using any convenient method for the generation of genetically modified animals, e.g. as known in the art or as described herein.

For example, a nucleic acid encoding the human protein of interest, e.g. IL-6, hM-CSF, hIL-3, hGM-CSF, hTPO, or hSIRPa, may be incorporated into a recombinant vector in a form suitable for insertion into the genome of the host cell and expression of the human protein in a non-human host cell. In various embodiments, the recombinant vector includes the one or more regulatory sequences operatively linked to the nucleic acid encoding the human protein in a manner which allows for transcription of the nucleic acid into mRNA and translation of the mRNA into the human protein, as described above. It will be understood that the design of the vector may depend on such factors as the choice of the host cell to be transfected, the amount of human protein to be expressed, and/or how the encoding nucleic acid will integrate into the genome of the non-human host, e.g. as known in the art.

Any of various methods may then be used to introduce the human nucleic acid sequence into an animal cell to produce a genetically modified animal that expresses the human gene. Such techniques are well-known in the art and include, but are not limited to, pronuclear microinjection of oocytes, transformation of embryonic stem cells, homologous recombination and knock-in techniques. Methods for generating genetically modified animals that can be used include, but are not limited to, those described in Sundberg and Ichiki (2006, Genetically Engineered Mice Handbook, CRC Press), Hofker and van Deursen (2002, Genetically modified Mouse Methods and Protocols, Humana Press), Joyner (2000, Gene Targeting: A Practical Approach, Oxford University Press), Turksen (2002, Embryonic stem cells: Methods and Protocols in Methods Mol Biol., Humana Press), Meyer et al. (2010, Proc. Nat. Acad. Sci. USA 107:15022-15026), and Gibson (2004, A Primer Of Genome Science 2' ed. Sunderland, Massachusetts: Sinauer), U.S. Pat. No. 6,586,251, Rathinam et al. (2011, Blood 118:3119-28), Willinger et al., (2011, Proc Natl Acad Sci USA, 108:2390-2395), Rongvaux et al., (2011, Proc Natl Acad Sci USA, 108:2378-83) and Valenzuela et al. (2003, Nat Biot 21:652-659).

For example, the subject genetically modified animals can be created by introducing the nucleic acid encoding the human protein into an oocyte, e.g., by microinjection, and allowing the oocyte to develop in a female foster animal. In preferred embodiments, the construct comprising the human nucleic acid sequence is injected into fertilized oocytes. Fertilized oocytes can be collected from superovulated females the day after mating and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo (2002, A Laboratory Manual, 3rd edition, Cold Spring Harbor Laboratory Press). Offspring can be evaluated for the presence of the introduced nucleic acid by DNA analysis (e.g., PCR, Southern blot, DNA sequencing, etc.) or by protein analysis (e.g., ELISA, Western blot, etc.). Such methods typically result in the random integration of the injected nucleic acid sequence—in this instance, the construct comprising the nucleic acid encoding the human protein of interest—into the genome of the oocyte and hence the non-human animal, i.e. at a locus other than the locus in the host animal expressing the corresponding protein.

As another example, the construct comprising the nucleic acid encoding the human protein may be transfected into stem cells (ES cells or iPS cells) using well-known methods, such as electroporation, calcium-phosphate precipitation, lipofection, etc. The cells can be evaluated for the presence of the introduced nucleic acid by DNA analysis (e.g., PCR, Southern blot, DNA sequencing, etc.) or by protein analysis (e.g., ELISA, Western blot, etc.). Cells determined to have incorporated the expression construct can then be introduced into preimplantation embryos. For a detailed description of methods known in the art useful for the compositions and methods of the invention, see Nagy et al., (2002, Manipulating the Mouse Embryo: A Laboratory Manual, 3rd edition, Cold Spring Harbor Laboratory Press), Nagy et al. (1990, Development 110:815-821), U.S. Pat. Nos. 7,576,259, 7,659,442, 7,294,754, and Kraus et al. (2010, Genesis 48:394-399). Such methods are typically used in the targeted integration of the transfected nucleic acid sequence—in this instance, the construct comprising the nucleic acid encoding the human protein of interest—into the genome of the stem cells and hence the non-human animal. Often, such methods result in the replacement of host genomic material, e.g. genomic material encoding the corresponding host protein, with the nucleic acid encoding the human protein of interest.

A genetically modified founder animals can be used to breed additional animals carrying the genetic modification. Genetically modified animals carrying a nucleic acid encoding the human protein(s) of the present disclosure can further be bred to other genetically modified animals carrying other genetic modifications, or be bred to knockout animals, e.g., a knockout animal that does not express one or more of its genes.

In some embodiments, the genetically modified immunodeficient animals comprise a genome that includes a nucleic acid encoding a human polypeptide operably linked to a promoter, wherein the animal expresses the encoded human polypeptide. In various embodiments, the genetically modified immunodeficient non-human animals comprise a genome that comprises an expression cassette that includes a nucleic acid encoding at least one human polypeptide, wherein the nucleic acid is operably linked to a promoter and a polyadenylation signal and further contains an intron, and wherein the animal expresses the encoded human polypeptide.

As discussed above, in some embodiments, the subject genetically modified animal is an immunodeficient animal. Genetically modified non-human animals that are immunodeficient and comprise one or more human cytokines, e.g. IL-6, M-CSF, IL-3, GM-CSF, TPO, and/or SIRPa, may likewise be generated using any convenient method for the generation of genetically modified animals, e.g. as known in the art or as described herein, e.g. DNA injection of an expression construct into a preimplantation embryo or by use of stem cells, such as embryonic stem (ES) cells or induced pluripotent stem (iPS) cells, for example, comprising a mutant SCID gene allele that, when homozygous, will result in immunodeficiency, e.g. as described in greater detail above and in the working examples herein. Mice are then generated with the modified oocyte or ES cells using, e.g. methods described herein and known in the art, and mated to produce the immunodeficient mice comprising the desired genetic modification. As another example, genetically modified non-human animals can be generated in a non-immunodeficient background, and crossed to an animal comprising a mutant SCID gene allele that, when homozygous, will result in immunodeficiency, and the progeny mated to create an immunodeficient animal expressing the at least one human protein of interest.

Various embodiments of the invention provide genetically modified animals that include a human nucleic acid in substantially all of their cells, as well as genetically modified animals that include a human nucleic acid in some, but not all their cells. In some instances, e.g. targeted recombination, one copy of the human nucleic acid will be integrated into the genome of the genetically modified animals. In other instances, e.g. random integration, multiple copies, adjacent or distant to one another, of the human nucleic acid may be integrated into the genome of the genetically modified animals.

Thus, in some embodiments, the subject genetically modified non-human animal may be an immunodeficient animal comprising a genome that includes a nucleic acid encoding a human polypeptide operably linked to the corresponding non-human animal promoter, wherein the animal expresses the encoded human polypeptide. In other words, the subject genetically modified immunodeficient non-human animal comprises a genome that comprises an expression cassette that includes a nucleic acid encoding at least one human polypeptide, wherein the nucleic acid is operably linked to the corresponding non-human promoter and a polyadenylation signal, and wherein the animal expresses the encoded human polypeptide.

Utility

The genetically modified non-human animals provided in various embodiments of the present invention find many uses including, for example, for use as models of growth and differentiation of hematopoietic cells, for the in vivo evaluation of human hematopoiesis, for the in vivo evaluation of cancer cells, for in vivo study of an immune response, for in vivo evaluation of vaccines and vaccination regimens, for the use in testing the effect of agents that modulate cancer cell growth or survival, for the in vivo evaluation of a treatment of cancer, for in vivo production and collection of immune mediators, such as an antibody, and for use in testing the effect of agents that affect hematopoietic and immune cell function.

Towards this end, in some instances, the subject genetically modified non-human animal (a "host") is engrafted with at least one human hematopoietic cell. In some embodiments, methods are provided for producing an animal model for studies of the human hematopoietic system, comprising engrafting human hematopoietic cells into a subject genetically modified non-human animal (the "host"). In certain embodiments, methods are provided for engrafting human hematopoietic cells into the genetically modified non-human animal disclosed herein.

In some particular instances, the subject genetically modified non-human animal is engrafted with at least one human multiple myeloma cell. In some such embodiments, methods are provided for producing an animal model for cancer studies, comprising engrafting human multiple myeloma cells into a subject genetically modified non-human animal. In some such embodiments, the invention is a method of engrafting human multiple myeloma cells into a subject genetically modified non-human animal. The engrafted human multiple myeloma cells useful in the compositions and methods of the invention include any human multiple myeloma cell.

The human hematopoietic cells useful in the engraftment of the subject genetically modified non-human animals include any convenient human hematopoietic cell. Non-limiting examples of human hematopoietic cells useful in the invention include, but are not limited to, HSC, HSPC, leukemia initiating cells (LIC), and hematopoietic cells of any lineage at any stage of differentiation, including terminally differentiated hematopoietic cells of any lineage. In some instances, the human hematopoietic cell is a primary cell, where "primary cells", "primary cell lines", and "primary cultures" are used interchangeably herein to include acutely isolated cells, or cell cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. In other embodiments, the human hematopoietic cell is from a cell line, that is, the cell is from a culture that is immortalized, e.g. it has been passaged more than about 15 times. In some instances, the hematopoietic cells that are engrafted comprise healthy cells. In other instances, the hematopoietic cells that are engrafted comprise diseased hematopoietic cells, e.g. cancerous hematopoietic cells, e.g. cancerous effector B cells, i.e. multiple myeloma cells. In some instances, the hematopoietic cells that are engrafted comprise both healthy and diseased cells, e.g. healthy B cells and cancerous effector B cells, healthy T cells and cancerous effector B cells, etc.

Hematopoietic cells, i.e. primary cells, cell lines generated therefrom, etc., can be derived from any tissue or location of a human donor, including, but not limited to, bone marrow, peripheral blood, liver, fetal liver, or umbilical cord blood. Such hematopoietic cells can be isolated from any human donor, including healthy donors, as well as donors with disease, such as cancer, including leukemia. Engraftment of hematopoietic cells in the subject genetically modified animal is characterized by the presence of human hematopoietic cells in the engrafted animal. In particular embodiments, engraftment of hematopoietic cells in the subject genetically modified animal is characterized by the presence of differentiated human hematopoietic cells in the engrafted animal in which hematopoietic cells are provided, as compared with appropriate control animals.

Isolation of human hematopoietic cells, administration of the human hematopoietic cells to a host animal and methods for assessing engraftment thereof are well-known in the art. Hematopoietic cells, including either normal and neoplastic cells, or combinations thereof, for administration to a host animal can be obtained from any tissue containing hematopoietic cells such as, but not limited to, umbilical cord blood, bone marrow, peripheral blood, cytokine or chemotherapy-mobilized peripheral blood and fetal liver. Exemplary methods of isolating human hematopoietic cells, of administering human hematopoietic cells to a host animal, and of assessing engraftment of the human hematopoietic cells in the host animal are described herein and in Pearson et al. (2008, Curr. Protoc. Immunol. 81:1-15), Ito et al. (2002, Blood 100:3175-3182), Traggiai et al. (2004, Science 304:104-107), Ishikawa et al. (2005, Blood 106: 1565-1573), Shultz et al. (2005, J. Immunol. 174:6477-6489) and Holyoake et al. (1999, Exp Hematol. 27:1418-27).

In some embodiments of the invention, the human hematopoietic cells, including either normal and neoplastic cells, or combinations thereof, are isolated from an original source material to obtain a population of cells enriched for a particular hematopoietic cell population (e.g., HSCs, HSPCs, LICs, CD34+, CD34−, lineage specific marker, cancer cell marker, etc.). The isolated hematopoietic cells may or may not be a pure population. In one embodiment, hematopoietic cells useful in the compositions and methods of the invention are depleted of cells having a particular marker. In another embodiment, hematopoietic cells useful in the compositions and methods of the invention are enriched by selection for a marker. In some embodiments, hematopoietic cells useful in the compositions and methods of the invention are a population of cells in which the selected cells constitute about 1-100% of the cells, although in certain embodiments, a population of cells in which the selected cells constitute fewer than 1% of total cells can also be used. In one embodiment, hematopoietic cells useful in the compositions and methods of the invention are depleted of cells having a particular marker, such as CD34. In another embodiment, hematopoietic cells useful in the compositions and methods of the invention are enriched by selection for a marker, such as CD34. In some embodiments, hematopoietic cells useful in the compositions and methods of the invention are a population of cells in which CD34+ cells constitute about 1-100% of the cells, although in certain embodiments, a population of cells in which CD34+ cells constitute fewer than 1% of total cells can also be used. In certain embodiments, the hematopoietic cells useful in the compositions and methods of the invention are a T cell-depleted population of cells in which CD34+ cells make up about 1-3% of total cells, a lineage-depleted population of cells in which CD34+ cells make up about 50% of total cells, or a CD34+ positive selected population of cells in which CD34+ cells make up about 90% of total cells.

The number of hematopoietic cells administered is not considered limiting with regard to the generation of a human hematopoietic and/or immune system in a genetically modified non-human animal expressing at least one human gene. Thus, by way of non-limiting example, the number of hematopoietic cells administered can range from about $1\times10^3$ to about $1\times10^7$, although in various embodiments, more or fewer can also be used. By way of another non-limiting example, the number of HSPCs administered can range from about $3\times10^3$ to about $1\times10^6$ CD34+ cells when the recipient is a mouse, although in various embodiments, more or fewer can also be used. For other species of recipient, the number of cells that need to be administered can be determined using only routine experimentation.

For example, in one embodiment, the genetically modified and treated mouse is engrafted with human hematopoietic cells or human hematopoietic stem cells (HPSCs) to form a genetically modified and engrafted mouse. In one embodiment, the hematopoietic cells are selected from human umbilical cord blood cells and human fetal liver cells. In one embodiment, engraftment is with about $1-2\times10^5$ human CD34+ cells.

In some instances, administration of the hematopoietic cells (e.g., normal or neoplastic) may be preceded by conditioning, e.g. either sub-lethal irradiation of the recipient animal with high frequency electromagnetic radiation, generally using gamma or X-ray radiation, or treatment with a radiomimetic drug such as busulfan or nitrogen mustard. Conditioning is believed to reduce numbers of host hematopoietic cells, create appropriate microenvironmental factors for engraftment of human hematopoietic cells, and/or create microenvironmental niches for engraftment of human hematopoietic cells. Standard methods for conditioning are known in the art, such as described herein and in J. Hayakawa et al, 2009, Stem Cells, 27(1):175-182. In one embodiment, the genetically modified mouse is treated so as to eliminate endogenous hematopoietic cells that may exist in the mouse. In one embodiment, the treatment comprises irradiating the genetically modified mouse. In a specific embodiment, newborn genetically modified mouse pups are irradated sublethally. In a specific embodiment, newborn pups are irradiated 2×200 cGy with a four hour interval.

Hematopoietic cells (e.g., normal or neoplastic) can be administered into newborn or adult animals by administration via various routes, such as, but not limited to, intravenous, intrahepatic, intraperitoneal, intrafemoral and/or intratibial. Methods for engraftment of human hematopoietic cells, including either normal and neoplastic cells, or combinations thereof, in immunodeficient animals are provided according to embodiments of the present invention which include providing human hematopoietic cells to the immunodeficient animals, with or without irradiating the animals prior to administration of the hematopoietic cells. Methods for engraftment of human hematopoietic cells in immunodeficient animals are provided according to embodiments of the present invention which include providing human hematopoietic cells, including either normal and neoplastic cells, or combinations thereof, to the genetically modified non-human animals of the invention, with or without, administering a radiomimetic drug, such as busulfan or nitrogen mustard, to the animals prior to administration of the hematopoietic cells.

Engraftment of human hematopoietic cells, including either normal and neoplastic cells, or combinations thereof, in the genetically modified animal of the invention can be assessed by any of various methods, such as, but not limited to, flow cytometric analysis of cells in the animals to which the human hematopoietic cells are administered at one or more time points following the administration of hematopoietic cells.

Generally, engraftment can be considered successful when the number (or percentage) of human hematopoietic cells, including either normal and neoplastic cells, or combinations thereof, present in the genetically modified non-human animal is greater than the number (or percentage) of human cells that were administered to the non-human animal, at a point in time beyond the lifespan of the administered human hematopoietic cells. Detection of the progeny of the administered hematopoietic cells can be achieved by detection of human DNA in the recipient animal, for example, or by detection of intact human hematopoietic cells, such as by the detection of the human cell marker, such as human CD45, human CD34, or sIL-6R for example. Serial transfer of human hematopoietic cells from a first recipient into a secondary recipient, and engraftment of human hematopoietic cells in the second recipient, is a further optional test of engraftment in the primary recipient. Engraftment can be detected by flow cytometry as 0.05% or greater human CD45+ cells in the blood, spleen or bone marrow at 1-4 months after administration of the human hematopoietic cells. A cytokine (e.g., GM-CSF) can be used to mobilize stem cells, for example, as described in Watanabe (1997, Bone Marrow Transplantation 19:1175-1181).

In one embodiment, the immunodeficient genetically modified and engrafted animal gives rise to a human cell selected from a CD34+ cell, a hematopoietic stem cell, a hematopoietic cell, a myeloid precursor cell, a myeloid cell, a dendritic cell, a monocyte, a granulocyte, a neutrophil, a mast cell, a thymocyte, a T cell, a B cell, a platelet, and a combination thereof. In one embodiment, the human cell is present at 4 months, 5 months, 6 months, 7 months, 8 months, 9 months, 10 months, 11 months, or 12 months after engraftment.

In one embodiment, the immunodeficient genetically modified and engrafted animal gives rise to a human hemato-lymphoid system that comprises human hematopoietic stem and progenitor cells, human myeloid progenitor cells, human myeloid cells, human dendritic cells, human monocytes, human granulocytes, human neutrophils, human mast cells, human thymocytes, human T cells, human B cells, and human platelets. In one embodiment, the human hemato-lymphoid system is present at 4 months, 5 months, 6 months, 7 months, 8 months, 9 months, 10 months, 11 months, or 12 months after engraftment.

In one embodiment, the immunodeficient genetically modified and engrafted animal gives rise to a human hemato-lymphoid system that comprises cancerous human hematopoietic cells, for example neoplastic plasma (effector B) cells. In one embodiment, the cancerous human hematopoietic cells are present at 4 weeks, at 6 weeks, at 8 weeks, at 12 weeks, or at more than 12 weeks after engraftment. In certain embodiments, the cancerous human hematopoietic cells are present at 2 weeks, at 4 weeks, at 6 weeks, at 8 weeks, at 12 weeks, or at more than 12 weeks after engraftment.

Once engrafted with human hematopoietic cells, the subject genetically modified non-human animals find many uses in the art. For example, engrafted genetically modified animals of the present disclosure are useful for studying the function of human hematopoietic cells in peripheral blood. As demonstrated in working example 2, genetically modified mice that are immunodeficient and comprise a nucleic acid encoding human IL-6 operably linked to an IL-6 promoter at the IL-6 mouse locus (e.g., Rag2$^{-/-}$IL2rg$^{null}$IL-6$^{h/h}$ mice, Rag2$^{-/-}$IL2rg$^{null}$IL-6$^{h/h}$ hSIRPa$^1$ mice, and Rag2$^{-/-}$IL2rg$^{-/-}$ IL-6$^{h/h}$ M-CSF$^{h/h}$ IL-3$^{h/h}$ GM-CSF$^{h/h}$ TPO$^{h/h}$, hSIRPa+) support engraftment of human hematopoietic cells, e.g. CD34$^+$ progenitor cells, into the peripheral blood and spleen better than immunodeficient mice that do not express human IL-6, i.e. Rag2$^{-/-}$IL2rg$^{null}$ mice. Moreover, these genetically modified mice promote the differentiation of human hematopoietic cells more efficiently than immunodeficient mice that do not express human IL-6. For example, these genetically modified mice better promote the differentiation of CD5+ B cells and CD27+ B cells. CD5 is a protein found on a subset of IgM-secreting B cells called B-1 cells, and serves to mitigate activating signals from the B cell receptor so that the B-1 cells can only be activated by very strong stimuli (such as bacterial proteins) and not by normal tissue proteins. CD27 is a marker for memory B cells. Additionally, these genetically modified mice support the development of better-functioning human hematopoietic cells than immunodeficient mice that do not express human IL-6. For example, B cells differentiate into IgG secreting plasma cells more rapidly in these genetically modified mice than in immunodeficient mice that do not express human IL-6. As such, engrafted genetically modified animals of the present disclosure find use in studying hematopoietic cell development and function, and more particularly, B lymphocyte differentiation and function.

As another example, engrafted genetically modified animals of the present disclosure are useful for studying hematopoietic cancers. As demonstrated in working example 1 below, genetically modified mice that are immunodeficient and comprise a nucleic acid encoding human IL-6 operably linked to an IL-6 promoter at the mouse IL-6 locus, e.g. Rag2$^{-/-}$IL2rg$^{null}$IL-6$^{h/h}$ mice, Rag2$^{-/-}$IL2rg$^{null}$IL-6$^{h/h}$ hSIRPa$^+$ mice, and Rag2$^{-/-}$ IL2rg$^{-/-}$ IL-6$^{h/h}$ M-CSF$^{h/h}$ IL-3$^{h/h}$ GM-CSF$^{h/h}$ TPO$^{h/h}$, hSIRPa+, engraft with primary human multiple myeloma cells and cells of human multiple myeloma cell lines, whereas immunodeficient mice that do not express human IL-6, i.e. Rag2$^{-/-}$ IL2rg$^{null}$ mice, do not. Expression of human SIRPa by the genetically modified host further improves the rate and extent of engraftment observed. Furthermore, engraftment of the multiple myeloma cells directly to bone of these immunodeficient, genetically modified mice disclosed herein reproduces the bone pathology typically associated with human multiple myeloma, e.g. bone destruction and resorption, e.g. as quantified by µCT scan.

As such, engrafted genetically modified animals of the present disclosure find use in screening candidate agents to identify those that will treat hematopoietic cancers. The terms "treatment", "treating" and the like are used herein to generally include obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein include any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Candidate agents of interest as therapeutics for hematopoietic cancers include those that may be administered before, during or after the onset of cancer. The treatment of ongoing disease, where the treatment stabilizes or reduces the undesirable clinical symptoms of the patient, is of particular interest. The terms "individual," "subject," "host," and "patient," are used interchangeably herein and include any mammalian subject for whom diagnosis, treatment, or therapy is desired, particularly humans.

As another example, engrafted genetically modified animals of the present disclosure are useful for studying human pathogens, i.e. pathogens that infect humans; the response of the human immune system to infection by human pathogens; and the effectiveness of agents in protecting against and/or treating infection by human pathogens. The pathogen may be a virus, a fungus, a bacterium, etc. Non-limiting examples of viral pathogens include human or porcine or avian influenza virus. Non-limiting examples of bacterial pathogens include mycobacterium, e.g. *Mycobacterium tuberculosis* (*M. tuberculosis*), and enterobacterium, e.g. *Salmonella typhi* (*S. typhi*). Examples of methods for infecting mice with *S. typhi* and for assessing infection may be found in, for example, US Published Application No. 2011/0200982, the disclosure of which is incorporated herein by reference. Examples of methods for infecting mice with *M. tuberculosis* and for assessing infection may be found in, for example, US Published Application No. 2011/0200982, the disclosure of which is incorporated herein by reference. Other examples of human pathogens that do not infect wild-type mice, or that infect wild-type mice but the infected mice do not model an immune response that a human mounts in response to the pathogen, will be well-known to the ordinarily skilled artisan. Such mouse models of pathogen infection are useful in research, e.g. to better understand the progression of human infection. Such mouse models of infection are also useful in drug discovery, e.g. to identify candidate agents that protect against or treat infection.

Engrafted genetically modified mice of the present disclosure also provide a useful system for screening candidate agents for desired activities in vivo, for example, to identify agents that are able to modulate (i.e., promote or suppress) hematopoietic cell development and/or activity, e.g. the activity of B cells, T cells, NK cells, macrophages, neutrophils, eosinophils, basophils, etc., e.g. in a healthy or a diseased state, e.g. as cancerous cells, during pathogen infection, for example to identify novel therapeutics and/or develop a better understanding of the molecular basis of the development and function of the immune system; for agents that are toxic to hematopoietic cells, e.g. B cells, T cells, NK cells, macrophages, neutrophils, eosinophils, basophils, etc., and progenitors thereof; and for agents that prevent against, mitigate, or reverse the toxic effects of toxic agents on hematopoietic cells, e.g. B cells, T cells, NK cells, macrophages, neutrophils, eosinophils, basophils, etc., and progenitors thereof; etc. As yet another example, engrafted genetically modified animals of the present disclosure provide a useful system for predicting the responsiveness of an individual to a disease therapy, e.g. by providing an in vivo platform for screening the responsiveness of an individual's immune system to an agent, e.g. a therapeutic agent, to predict the responsiveness of an individual to that agent.

In screening assays for biologically active agents, a human hematopoietic cell-engrafted genetically modified mouse of the present disclosure, e.g. an engrafted $Rag2^{-/-}$ $IL2rg^{-/-IL-}6^{h/h}$ hSIRPa+ mouse, an engrafted $Rag2^{-/-}$ $IL2rg^{-/-}$ $IL-6^{h/h}$ $M\text{-}CSF^{h/h}$ $IL\text{-}3^{h/h}$ $GM\text{-}CSF^{h/h}$ $TPO^{h/h}$ hSIRPa+ mouse, etc. is contacted with a candidate agent of interest and the effect of the candidate agent is assessed by monitoring one or more output parameters. These output parameters may be reflective of the viability of the cells, e.g. the total number of hematopoietic cells or the number of cells of a particular hematopoietic cell type, or of the apoptotic state of the cells, e.g. the amount of DNA fragmentation, the amount of cell blebbing, the amount of phosphatidylserine on the cell surface, and the like by methods that are well known in the art. Alternatively or additionally, the output parameters may be reflective of the differentiation capacity of the cells, e.g. the proportions of differentiated cells and differentiated cell types. Alternatively or additionally, the output parameters may be reflective of the function of the cells, e.g. the cytokines and chemokines produced by the cells, the antibodies (e.g. amount or type) produced by the cells, the ability of the cells to home to and extravasate to a site of challenge, the ability of the cells to modulate, i.e. promote or suppress, the activity of other cells in vitro or in vivo, etc. Other output parameters may be reflective of the extent of damage induced by diseased hematopoietic cells, e.g. bone destruction and resorption induced by multiple myeloid cells. Yet other parameters may be reflective of the effect of the agent on infection, e.g. pathogen infection in the animal, e.g. the titer of pathogen in the mouse, the presence of granuloma in the mouse, etc., as relevant to the studies being performed.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, vaccines, antibiotics or other agents suspected of having antibiotic properties, peptides, polypeptides, antibodies, agents that have been approved pharmaceutical for use in a human, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the pluripotent cells are contacted with vectors comprising the nucleic acid of interest such that the vectors are taken up by the cells.

Methods for contacting cells, e.g. cells in culture or cells in a mouse, with nucleic acid vectors, such as electroporation, calcium chloride transfection, and lipofection, are well known in the art. Alternatively, the nucleic acid of interest may be provided to the cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the cells of interest—in some instance, the engrafted cells, in some instance, the cells of the host, i.e. the genetically modified animal—are targeted by the packaged viral particles.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Additionally or alternatively, such polypeptides may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The candidate polypeptide agent may be produced from eukaryotic cells, or may be produced by prokaryotic cells. It may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured. Antibody production and screen is discussed in greater detail below.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by administering the agent to at least one and usually a plurality of samples, sometimes in conjunction with samples lacking the agent. The change in parameters in response to the agent is measured, and the result evaluated by comparison to reference cultures, e.g. in the presence and absence of the agent, obtained with other agents, etc. In instances in which a screen is being performed to identify candidate agents that will prevent, mitigate or reverse the effects of a toxic agent, the screen is typically performed in the presence of the toxic agent, where the toxic agent is added at the time most appropriate to the results to be determined. For example, in cases in which the protective/preventative ability of the candidate agent is tested, the candidate agent may be added before the toxic agent, simultaneously with the candidate agent, or subsequent to treatment with the candidate agent. As another example, in cases in which the ability of the candidate agent to reverse the effects of a toxic agent is tested, the candidate agent may be added subsequent to treatment with the candidate agent. As mentioned above, in some instances, the "sample" is a genetically modified non-human animal that has been engrafted with cells, e.g. the candidate agent is provided to an immunodeficient animal, e.g. mouse, comprising a nucleic acid encoding human IL-6 operably linked to an IL-6 promoter that has been engrafted with human hematopoietic cells. In some instances, the sample is the human hematopoietic cells to be engrafted, i.e. the candidate agent is provided to cells prior to engraftment into the immunodeficient genetically modified animal.

If the candidate agent is to be administered directly to the engrafted genetically modified animal, the agent may be administered by any of a number of well-known methods in the art for the administration of peptides, small molecules and nucleic acids to mice. For example, the agent may be administered orally, mucosally, topically, intrdermally, or by injection, e.g. intraperitoneal, subcutaneous, intramuscular, intravenous, or intracranial injection, and the like. The agent may be administered in a buffer, or it may be incorporated into any of a variety of formulations, e.g. by combination with appropriate pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. The agent may be systemic after administration or may be localized by the use of regional administration, intramural administration, or use of an implant that acts to retain the active dose at the site of implantation. The active agent may be formulated for immediate activity or it may be formulated for sustained release. For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. A BBB disrupting agent can be co-administered with the agent when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

If the agent(s) are provided to cells prior to engraftment, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

An analysis of the response of cells in the engrafted genetically modified animal to the candidate agent may be performed at any time following treatment with the agent. For example, the cells may be analyzed 1, 2, or 3 days, sometimes 4, 5, or 6 days, sometimes 8, 9, or 10 days, sometimes 14 days, sometimes 21 days, sometimes 28 days, sometimes 1 month or more after contact with the candidate agent, e.g. 2 months, 4 months, 6 months or more. In some embodiments, the analysis comprises analysis at multiple time points. The selection of the time point(s) for analysis will be based upon the type of analysis to be performed, as will be readily understood by the ordinarily skilled artisan.

The analysis may comprise measuring any of the parameters described herein or known in the art for measuring cell viability, cell proliferation, cell identity, cell morphology, and cell function, particularly as they may pertain to cells of the immune cells. For example, flow cytometry may be used to determine the total number of hematopoietic cells or the number of cells of a particular hematopoietic cell type. Histochemistry or immunohistochemistry may be performed to determine the apoptotic state of the cells, e.g. terminal deoxynucleotidyl transferase dUTP nick end labeling (TUNEL) to measure DNA fragmentation, or immunohistochemistry to detect Annexin V binding to phosphatidylserine on the cell surface. Flow cytometry may also be employed to assess the proportions of differentiated cells and differentiated cell types, e.g. to determine the ability of hematopoietic cells to differentiate in the presence of agent. ELISAs, Westerns, and Northern blots may be performed to determine the levels of cytokines, chemokines, immunoglobulins, etc. expressed in the engrafted genetically modified mice, e.g. to assess the function of the engrafted cells, to assess the survival of cancerous plasma cells, etc. μCT scans may be performed to determine the extent of damage induced by diseased hematopoietic cells, e.g. bone destruction and resorption induced by multiple myeloid cells. In vivo assays to test the function of immune cells, as well as assays relevant to particular diseases or disorders of interest such as diabetes, autoimmune disease, graft v. host disease, AMD, etc. may also be performed. See, e.g. Current Protocols in Immunology (Richard Coico, ed. John Wiley & Sons, Inc. 2012) and Immunology Methods Manual (I. Lefkovits ed., Academic Press 1997), the disclosures of which are incorporated herein by reference.

So, for example, a method is provided for determining the effect of an agent on multiple myeloma, comprising administering the agent to a humanized IL-6 mouse, e.g. a Rag2$^{-/-}$IL2rg$^{-/-}$IL-6$^{h/h}$ mouse, that has been engrafted with human multiple myeloma cells; measuring a parameter of the viability and/or proliferative ability of the multiple myeloma cells over time in the presence of the agent; and comparing that measurement to the measurement from an engrafted humanized IL-6 mouse not exposed to the agent. The agent is determined to be anti-cancerous if it reduces the proliferation of and/or reduces the number of multiple myeloma cells in blood or a tissue of the mouse by at least 20%, 30%, 40% or more, in some instances 50%, 60%, 70% or more, e.g. 80%, 90% or 100%, i.e., to undetectable amounts, following a single administration or two or more administrations of the agent over a selected period of time. In a specific embodiment, the administration of the drug or combination of drugs is at least a week, 10 days, two week, three weeks, or four weeks after engraftment of the multiple myeloma cells.

Other examples of uses for the subject mice are provided elsewhere herein. Additional applications of the genetically modified and engrafted mice described in this disclosure will be apparent to those skilled in the art upon reading this disclosure.

Human Antibody Production

Also provided are compositions and methods useful for the production of human monoclonal antibodies from an engrafted immunodeficient animal, as elsewhere described herein. In various embodiments, the methods comprise contacting an immunodeficient animal with a human hematopoietic cell to generate an immune system-transplanted non-human animal (engrafted animal), subsequently contacting the engrafted animal with an antigen, collecting from the engrafted animal a human cell producing a human antibody against the antigen, and isolating the antibody from the antibody producing cell.

In various embodiments, the invention comprises a method that includes establishing an antibody producing cell (e.g., a human B-cell) by a transformation method (e.g. EBV) or a cell fusion method (e.g. hybridoma). Preferably the antibody producing cell is capable of being maintained under suitable cell culture conditions for at least about 50 passages.

In various embodiments, the engrafted animal is a non-human mammal. In some embodiments, the engrafted animal is a mouse, rat or a rabbit.

In various embodiments of the invention, the human hematopoietic cell is CD34+ cell obtained from a human fetal liver, bone marrow, cord blood, peripheral blood, or spleen sample.

In various embodiments, the antigen is at least one of: a peptide, a polypeptide, an MHC/peptide complex, DNA, a live virus, a dead virus or portion thereof, a live bacteria, a dead bacteria or portion thereof, or a cancer cell or portion thereof.

In some embodiments, the engrafted animal has been contacted with the antigen 1-5 months after the animal has been contacted with the human hematopoietic cell. In some embodiments, the engrafted animal is contacted only one time with the antigen, while in other embodiments, the engrafted animal is contacted two, three, four, five, six, seven, eight, or more times with the antigen.

In one embodiment, human antibody producing cell collected from the engrafted animal is a B cell. In various embodiments, the human antibody producing cell collected from the animal expresses on its surface at least one of: CD19, CD20, CD22, and CD27. The human antibody-producing cell of the invention can be recovered by removal of any suitable cellular components of the immune system from the animal. In various embodiments, the antibody-producing cell is removed from the engrafted animal by removal of at least one of the spleen, the lymph nodes, the peripheral blood, the bone marrow or portions thereof.

In various embodiments, the method of the invention employs a conventional hybridoma technology using a suitable fusion partner. In various embodiments, the fusion partner is at least one cell selected from the group consisting of: MOPC21, P3X63AG8, SP2/0, NS-1, P3.X63AG8.653, FO, S194/5.XXO.BU-1, FOX-NY, SP2/0-Ag14, MEG-01, HEL, UT-7, M07e, MEG-A2, and DAMI, and cell lines derived from these cells.

Methods of isolating an antibody from the engrafted animal of the invention are well known in the art. Isolation of the antibody from the antibody producing cell, the media in which the antibody producing cell is culture, and/or the ascites of the engrafted animal, can be performed according to the methods known in the art, such as, by way of example, chromatography and dialysis. In other various embodiments, the antibody can be isolated using one or more of immunoaffinity purification, ammonium sulphate precipitation, protein A/G purification, ion exchange chromatography and gel filtration. Such methods are described in Nau (1989, Optimization of monoclonal antibody purification, In: Techniques in Protein Chemistry, Hugli, T. (ed.), Academic Press, New York) and Coligan et al. (2005, Current Protocols in Immunology, John Wiley & Sons, Inc.).

The antigen may be administered to the engrafted animal by any suitable means known in art. In various embodiments, the antigen can be administered to the engrafted animal by at least one of intrasplenically, intravenously, intraperitoneally, intradermally, intramuscularly, and subcutaneously. In some embodiments, the antigen is administered alone and in other embodiments, the antigen is administered in combination with appropriate immunomodulating agent or adjuvant. Examples of adjuvants useful in the methods of the invention include, but are not limited to, Complete Freund's Adjuvant (CFA), Incomplete Freund's Adjuvant (IFA), and Alum ($Al_3(OH)_4$).

Reagents and Kits

Also provided are reagents and kits thereof for practicing one or more of the above-described methods. The subject reagents and kits thereof may vary greatly. In some embodiments, the reagents or kits will comprise one or more reagents for use in the generation and/or maintenance of the subject genetically modified non-human animals. For example, the kit may comprise an immunodeficient mouse comprising a nucleic acid encoding human IL-6 operably linked to an IL-6 promoter and a nucleic acid encoding human SIRPa operably linked to a SIRPa promoter; or a mouse comprising a nucleic acid encoding human IL-6 operably linked to an IL-6 promoter and further comprising a nucleic acid encoding human M-CSF operably linked to an M-CSF promoter; a nucleic acid encoding human IL-3 operably linked to an IL-3 promoter; a nucleic acid encoding human GM-CSF operably linked to a GM-CSF promoter; a nucleic acid encoding human TPO operably linked to a TPO promoter; and/or a nucleic acid encoding human SIRPa operably linked to a SIRPa promoter. The kit may comprise reagents for breeding such mice, e.g. primers for genotyping for the human IL-6 gene, for the human M-CSF gene, for the human IL-3 gene, for the human GM-CSF gene, for the human SIRPa gene, and/or for the human TPO gene, PCR buffer, $MgCl_2$ solution, etc.

In some embodiments, the reagents or kits will comprise one or more reagents for use in engrafting the subject genetically modified non-human animals, for example human hematopoietic cells, an enriched population of human hematopoietic progenitor cells, a hematopoietic cell line, a neoplastic hematopoietic cell line, etc. for transplantation into the subject genetically modified non-human animals, or reagents for preparing a population of hematopoietic cells, an enriched population of hematopoietic cells from a human, a hematopoietic cell line, a neoplastic hematopoietic cell line, etc. for transplantation into a subject genetically modified non-human animals.

In some embodiments, the reagents or kits will include reagents for determining the viability and/or function of hematopoietic cells, e.g. in the presence/absence of a candidate agent, e.g. one or more antibodies that are specific for markers expressed by different types of hematopoietic cells, or reagents for detecting particular cytokines, chemokine, etc. Other reagents may include culture media, culture supplements, matrix compositions, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present Example 1

Genetic Humanization of Cytokine Genes Enables Engraftment of Mice with Human Multiple Myeloma Cells The data described herein demonstrate that the genetically modified non-human animals described herein represent a novel in vivo animal model for multiple myeloma.

Materials and Methods

Mice. Humanized IL-6 knock-in mice were generated by replacing 6.8 kb of the murine IL-6 gene locus with a 4.8-kb human IL-6 gene sequence containing exons 1 through 5 including 3' untranslated region of the human IL-6 gene.

Briefly, a targeting construct for replacing the mouse with the human IL-6 gene in a single targeting step was constructed using VELOCIGENE® genetic engineering technology (see, Valenzuela et al. (2003) High-throughput engineering of the mouse genome coupled with high-resolution expression analysis, Nature Biotech, 21(6):652-659). Mouse and human IL-6 DNA were obtained from bacterial artificial chromosome (BAC) RPCI-23 clone 368C3, and from BAC CTD clone 2369M23, respectively. Briefly, a NotI linearized targeting construct generated by gap repair cloning containing mouse IL-6 upstream and downstream homology arms flanking a 4.8 kb human IL-6 sequence extending from ATG in exon 1 to exon 5 with 16 nucleotides of 3' downstream sequence (genomic coordinates: NCBIh37.1: ch7:22,766,882 to 22,771,637) and a foxed neo selection cassette, was electroporated into $Rag2^{+/-}$ $IL2rg^{Y/-}$ ES cells. The parental ES cell line in which the RAG2 gene and IL2rg gene knockout was made was a commercially available V17 ES cell (BALB/cx129 heterozygote). Correctly targeted ES cells may be electroporated with a transient Cre-expressing vector to remove the drug selection cassette.

Correctly targeted ES cell clones were identified by a loss-of-native-allele (LONA) assay (Valenzuela et al. 2003) in which the number of copies of the native, unmodified Il6 gene were determined by two TaqMan™ quantitative polymerase chain reactions (qPCRs) specific for sequences in the mouse 116 gene that were targeted for deletion. The qPCR assays comprised the following primer-probe sets (written 5' to 3'): upstream forward primer, TTGCCGGTTT TCCCTTTTCT C (SEQ ID NO:1); upstream reverse primer, AGGGAAGGCC GTGGTTGTC (SEQ ID NO:2); upstream probe, FAM-CCAGCATCAG TCCCAAGAAG GCAACT-BHQ (SEQ ID NO:3); downstream forward primer, TCAGAGTGTG GGCGAACAAA G (SEQ ID NO:4); downstream reverse primer, GTGGCAAAAG CAGCCTTAGC (SEQ ID NO:5); downstream probe, FAM-TCATTCCAGG CCCTTCTTAT TGCATCTG-BHQ (SEQ ID NO:6); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream Il6-specific qPCRs and two qPCRs for non-targeted reference genes were run for each DNA sample. The differences in the Ct values (ΔCt) between each Il6-specific qPCR and each reference gene qPCR were calculated, and then the difference between each ΔCt and the median ΔCt for all samples assayed was calculated to obtain ΔΔCt values for each sample. The copy number of the IL-6 gene in each sample was calculated from the following formula: copy number=$2 \cdot 2^{-\Delta\Delta Ct}$. A correctly targeted clone, having lost one of its native copies, will have an IL-6 gene copy number equal to one. Confirmation that the human IL-6 gene sequence replaced the deleted mouse Il-6 gene sequence in the humanized allele was confirmed by a TaqMan™ qPCR assay that comprises the following primer-probe sets (written 5' to 3'): the human forward primer, CCCCACTCCACTGGAATTTG (SEQ ID NO:7); the human reverse primer, GTTCAACCACAGCCAGGAAAG (SEQ ID NO:8); and the human probe, FAM-AGCTA-CAACTCATTGGCATCCTGGCAA-BHQ (SEQ ID NO:9).

The upstream junction of the murine locus and the sequence containing the hIL-6 gene is designed to be within 5'-AATTAGAGAG TTGACTCCTA ATAAATATGA GACTGGGGAT GTCTGTAGCT CATTCTGCTC TGGAGCCCAC CAAGAACGAT AGTCAATTCC AGAAACCGCT ATGAACTCCT TCTCCACAAG TAAGTGCAGG AAATCCTTAG CCCTGGAACT GCCA-GCGGCG GTCGAGCCCT GTGTGAGGGA GGGGTGT-GTG GCCCAGG (SEQ ID NO:10), wherein the final mouse nucleotide prior to the first nucleotide of the human gene is the "T" in CCGCT, and the first nucleotide of the human sequence is the first "A" in ATGAA. The downstream junction of the sequence containing the hIL-6 gene and the murine locus is designed to be within 5'-TTTTAAAGAA ATATTTATAT TGTATTTATA TAATGTATAA ATG-GTTTTTA TACCAATAAA TGGCATTTTA AAAAAT-TCAG CAACTTTGAG TGTGTCACGC TCCCGGGCTC GATAACTATA ACGGTCCTAA GGTAGCGACT CGA-GATAACT T-3' (SEQ ID NO:11), wherein the final nucleotide of the human sequence is with the final "G" in TCACG and the first nucleotide of the mouse sequence is the first "C" in CTCCC; the downstream junction region also contained a loxP site at the 3' end (the beginning of which is shown) for removal of a foxed ubiquitin promoter-driven neo cassette. The junction of the neo cassette with the mouse IL-6 locus is designed to be within 5'-TATACGAAGT TATC-CTAGGT TGGAGCTCCT AAGTTACATC CAAACATCCT CCCCCAAATC AATAATTAAG CACTTTTTAT GACATGTAAA GTTAAATAAG AAGT-GAAAGC TGCAGATGGT GAGTGAGA (SEQ ID NO:12), where the final "C" of AGCTC is the final nucleotide of the neo cassette; the first nucleotide of the mouse genome following the cassette is the initial "C" of CTAAG.

To generate a mouse comprising hIL-6 and lacking Rag2 and Il2rg, correctly targeted ES cells are identified, and are introduced into preimplantation embryo using techniques known in the art.

Humanized IL-6 KI mice were then backcrossed to generate mice lacking Rag2 and Il2rg and expressing hIL-6, and crossed to mice expressing a human SIRPa transgene (Strowig et al., 2011, Proc Natl Acad Sci USA, 108(32): 13218-13223) to generate mice deficient for Rag2 and Il2rg as well as expressing both hIL-6 and hSIRPa ($Rag2^{-/-}$ $Il2rg^{null}$ $Il6^{h/h}hSIRI^3a^+$). In addition, $Rag2^{-/-}$, $IL-2rg^{Y/-}$, hIL-6 KI mice were crossed with mice expressing human TPO (Rongvaux et al., 2011, Proc Natl Acad Sci USA, 108(6): 2378-2383), human IL-3 and human GM-CSF (Willinger et al, 2011, Proc Natl Acad Sci USA, 108(6):

2390-2395), and human M-CSF (Rathinam et al, 2011, Blood, 118(11): 3119-3128) as well as hSIRPa (Strowig et al., 2011, Proc Natl Acad Sci USA, 108(32): 13218-13223) to generate mice expressing a combination of these human proteins (Rag2$^{-/-}$ Il2rg$^{null}$hSIRPa$^+$ Tpo$^{h/h}$ Mcsf$^{h/h}$ Il3/Gmcsf$^{h/h}$ Il6$^{h/h}$).

Cell lines and primary cells. The multiple myeloma cell line INA-6 (Burger et al., 2001, Hematol J, 2(1): 42-53) was maintained in RPMI1640 medium supplemented with 20% FCS, penicillin/streptomycin, L-glutamine, and 2.5 ng/ml of hIL-6 in a standard incubator at 37 C and 5% $CO_2$.

Primary cells from multiple myeloma patients were isolated from bone marrow aspirates after obtaining informed consent from patients. Mononuclear cells were purified by Ficoll density-gradient centrifugation and subsequently, different cell subsets were isolated by Magnetic-activated cell sorting)(MACS®). To obtain, T cell-depleted populations, CD3+ cells were depleted by negative selection on an AutoMACS system using anti-CD3 microbeads (Miltenyi Biotec). To obtain CD138+ cells, CD138+ cells were isolate by positive selection on an AutoMACS® system using anti-CD138 microbeads (Miltenyi Biotec). Purity of cells after MACS® selection was analyzed by flow cytometry.

Transplantation of cells. For intrafemoral transplantation of INA6 cells, Rag2$^{-/-}$ Il2rg$^{null}$ Il6$^{h/h}$hSIRPa$^+$ mice were irradiated twice with 200 rad from an X-ray source. Indicated amounts of cells were then transplanted into the femur of recipient mice. Briefly, mice were anaesthetized using Ketamine/Xylazine and a hole was drilled into the patellar surface of the femur using a 26 gauge needle. The cells were then slowly injected in a volume of 20 µl using a 27 gauge needle. For transplantation of primary patient-derived cells, Rag2$^{-/-}$Il2rg$^{null}$hSIRPa$^+$ Tpo$^{h/h}$ Mcsf$^{h/h}$ Il3/Gmcsf$^{h/h}$ Il6$^{h/h}$ mice were irradiated twice with 150 rad from an X-ray source and transplantation was performed as described above.

ELISA. Commercial ELISA kits were used to measure the concentrations of human soluble IL-6R (R&D Systems), human Igκ, and Igλ, (Bethyl Laboratories). Detection of these proteins was performed according to manufacturer's instructions.

µCT. Femur morphometry was quantified using conebeam microfocus x-ray computed tomography (µCT40; ScancoMedicalAG). Serial tomographic images were acquired, and 3D images were reconstructed and used to determine the parameters. Trabecular morphometry was characterized by measuring the bone volume fraction, trabecular thickness, trabecular number, and trabecular separation. Cortical measurements included average cortical thickness, cross-sectional area of cortical bone, subperiosteal cross-sectional area, and marrow area.

Histology. Femurs were stripped of soft tissue, fixed in 10% buffered formalin, dehydrated, and embedded in methyl methacrylate before being sectioned and stained with toluidine blue according to standard procedures.

Results

Engraftment of multiple myeloma cell line in mice with humanized IL-6 gene. A human IL-6 dependent MM cell line (INA6-gfp) was utilized to evaluate if mice expressing human SIRPα and IL-6 are suitable hosts for multiple myeloma (MM) cell lines. The INA6-gfp cell line shows high dependency on human microenvironment, i.e., human fetal bone chips, when transplanted in xenograft systems of scid-hu mice (Epstein et al., 2005, Methods Mol Med, 113: 183-190). Specifically, INA-6 cells are only able to engraft the human bone graft in scid-hu mice, suggesting dependence on a human bone marrow microenvironment, similar to primary MM cells (Tassone et al., 2005, Blood, 106(2): 713-716).

Figure 2:
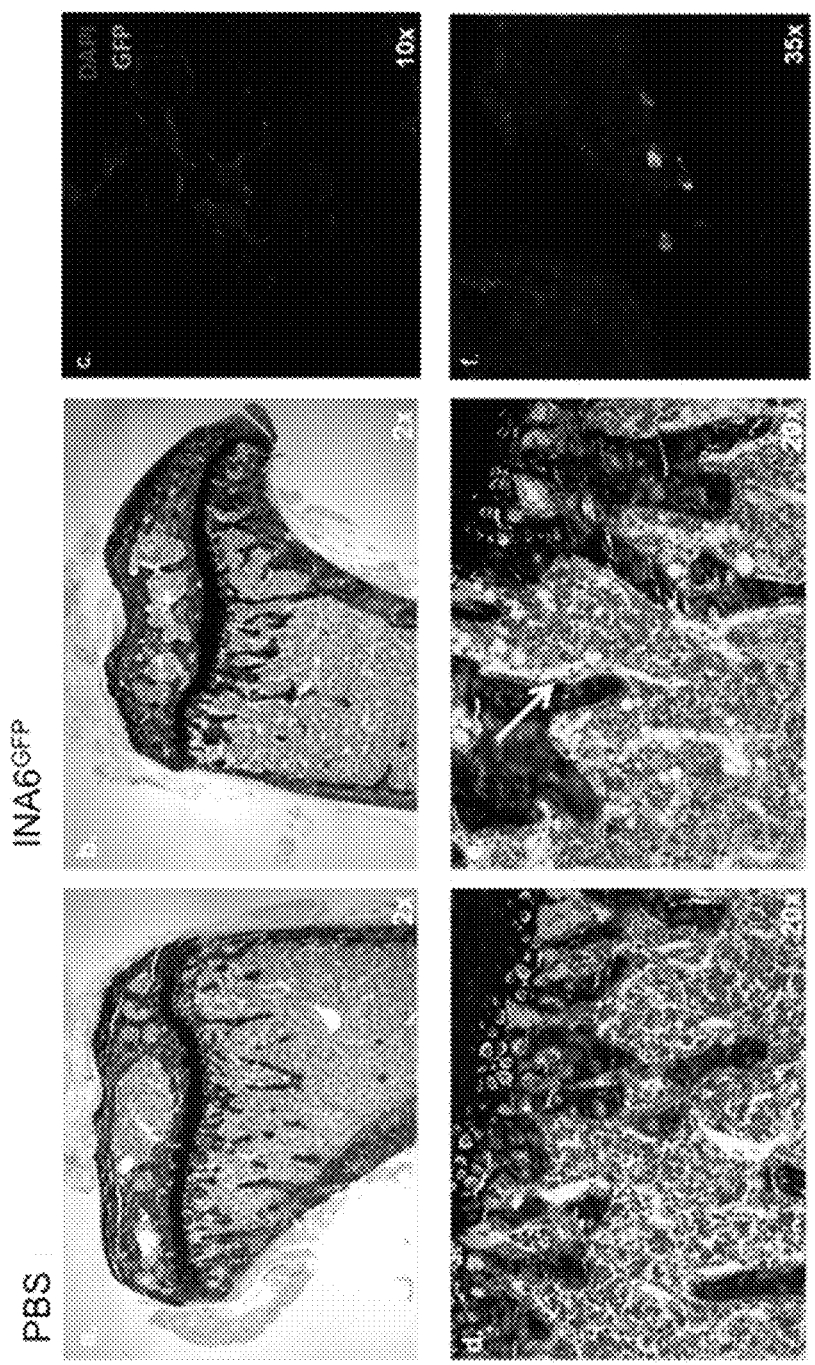
FIG. 2, comprising Panels A through F, is a set of images depicting the histological analysis of femurs after intravenous engraftment of INA-6 cells. $Rag2^{-/-}Il2rg^{null}$ $Il6^{h/h}$hSIRPa+ mice were sacrificed eight weeks after engraftment with $5\times10^6$ INA-6 cells intravenously. Femurs were fixed in 10% Formalin and decalcified. 10 µM sections were stained with Toluidine blue or directly analyzed for GFP expression using a Leica Confocal microscope.

Hence, to directly test the potential of IL-6 humanization in enabling the growth of myeloma cells, INA-6 cells were transplanted intravenously into i) Rag2$^{-/-}$Il2rg$^{null}$, ii) Rag2$^{-/-}$Il2rg$^{null}$hSIRPa+, iii) Rag2$^{-/-}$Il2rg$^{null}$ Il6$^{h/h}$, and iv) Rag2$^{-/-}$Il2rg$^{null}$ Il6$^{h/h}$hSIRPa+ mice. Engraftment was analyzed by measuring sIL-6R protein secreted by INA-6 cells in the blood. Engraftment was only detected in mice expressing human IL-6, (FIG. 1) demonstrating that INA-6 cells were indeed able to engraft mice expressing human IL-6. Next, the location of INA-6 cells (modified to express GFP) in the engrafted mice was investigated by fluorescent microscopy. Few GFP+ cells was detected in the bone marrow (FIG. 2), but an increased number of GFP+ cells was detected in the lung of engrafted mice (FIG. 3).

Analysis of human Il6 gene expression revealed that the highest level of human Il6 gene expression was found in the lung (FIG. 3), hence correlating with the presence of INA-6 cells in the lung. In summary, the data disclosed herein demonstrate the successful engraftment of INA-6 cells after intravenous injection (i.v.) into mice genetically modified to express human IL6 or human IL6 and SIRPa, suggesting that genetic humanization is able to overcome growth restrictions of human MM cells in mice.

Figure 3:
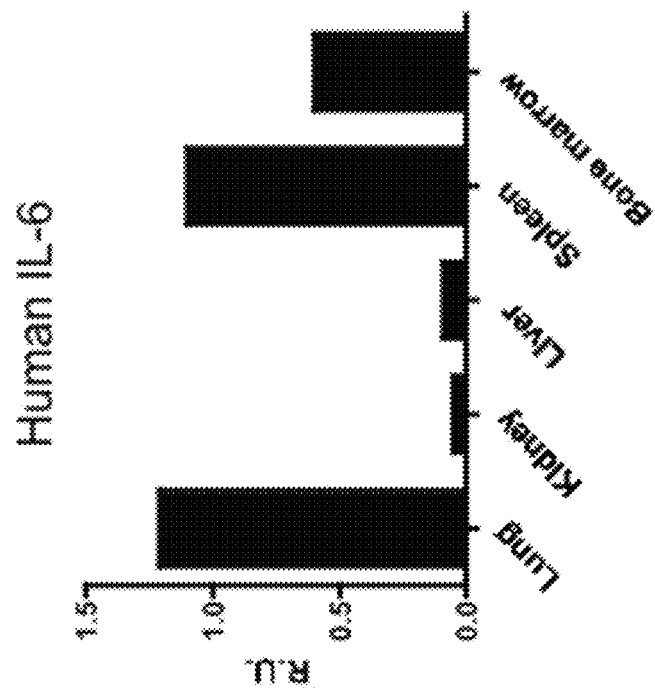
FIG. 3 is a set of images and a graph depicting the analysis of lungs after intravenous engraftment of INA-6 cells. $Rag2^{-/-}Il2rg^{null}$ $Il6^{h/h}$hSIRPa+ mice were sacrificed eight weeks after engraftment with $5\times10^6$ intravenously injected INA-6 cells. Lung tissue was fixed in 10% Formalin and 10 µM sections were directly analyzed for GFP expression using a Leica Confocal microscope. Images (left) depict a 10× (top) and 63× (bottom) magnification of sections. The graph (right) depicts human Il6 gene expression measured in indicated tissues and normalized to murine hprt expression.
Figure 3:
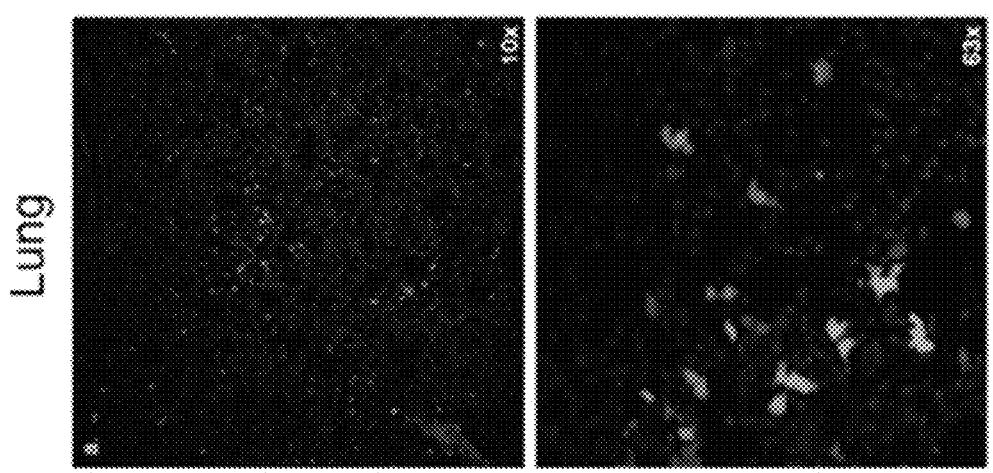
Figure 4:
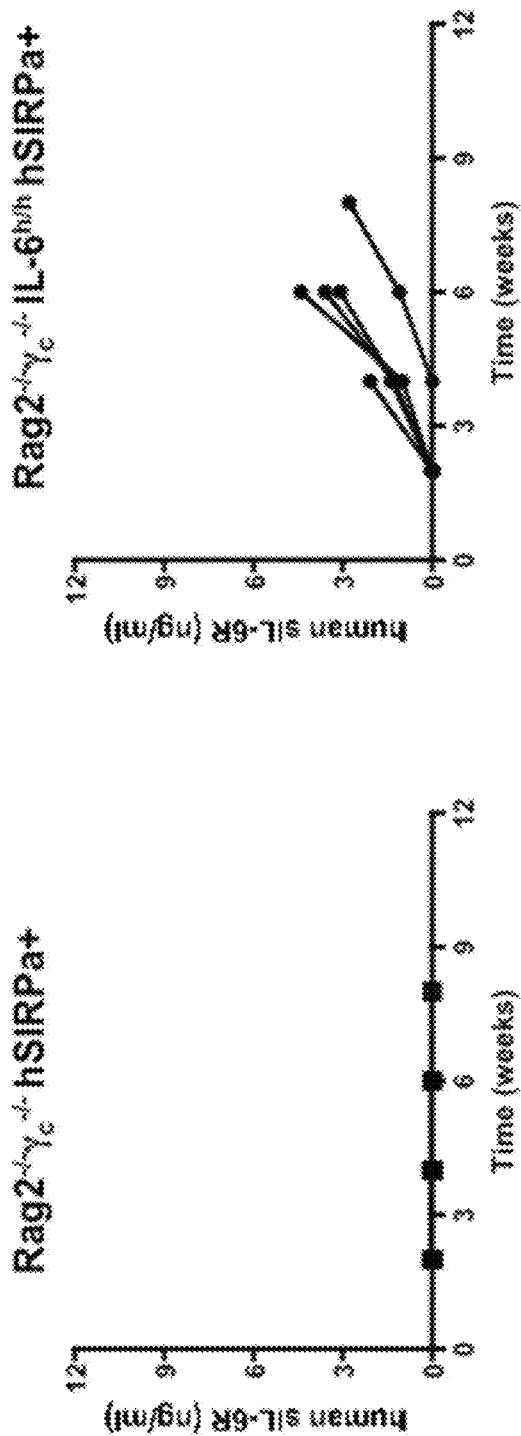
FIG. 4 is a set of graphs depicting the results of experiments demonstrating the engraftment of INA-6 cells in human IL-6 knock-in mice. Soluble IL-6R levels were measured in mice of the indicated genotypes transplanted with $5\times10^5$ INA-6 cells intrafemorally. Each line indicates an individual mouse.
Figure 5:
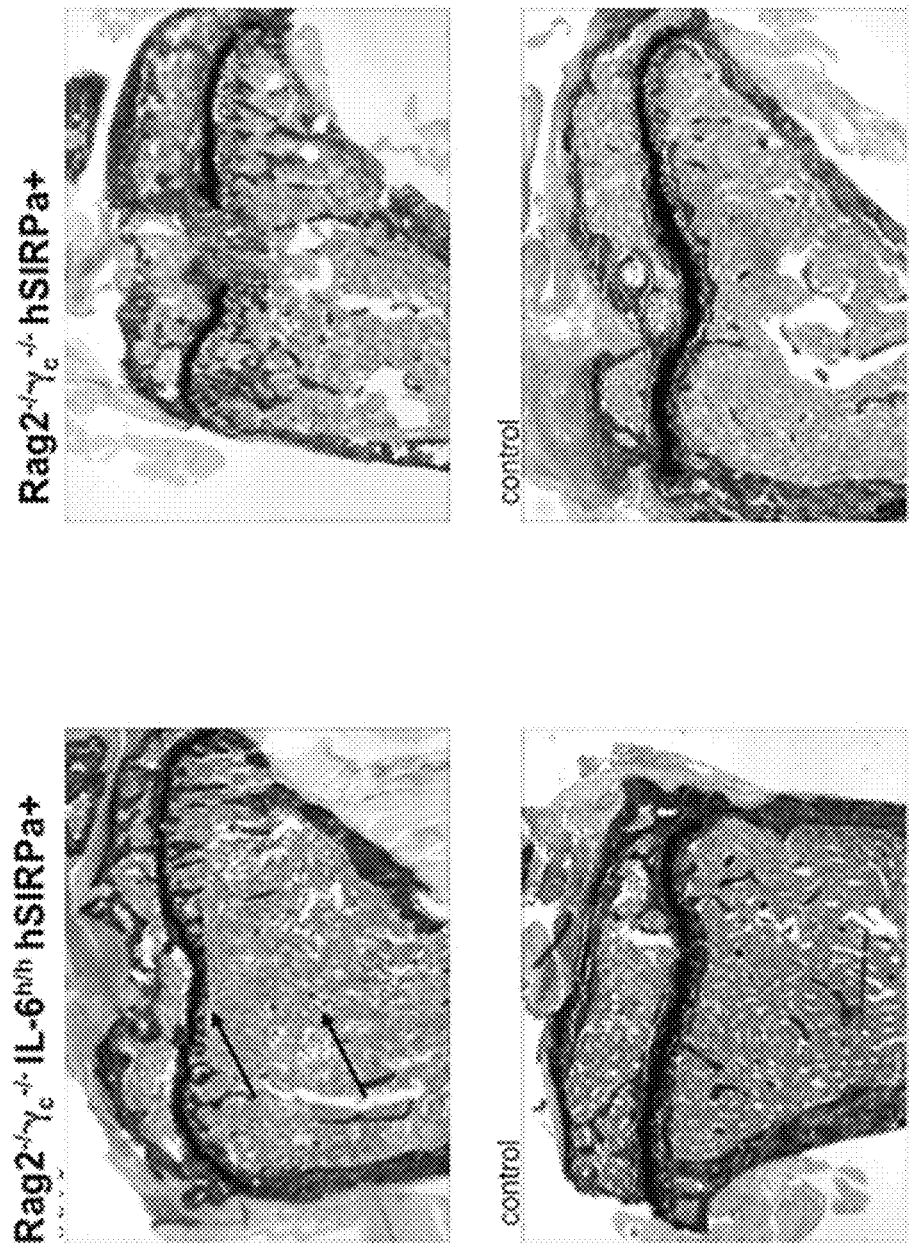
FIG. 5 is a set of images depicting the histological analysis of femurs after intrafemoral engraftment of INA-6 cells. $Rag2^{-/-}Il2rg^{null}$ $Il6^{h/h}$hSIRPa+ mice were sacrificed four to six weeks after engraftment with $5\times10^5$ intrafemorally injected INA-6 cells. Femurs were fixed in 10% Formalin and decalcified. 10 µM sections were stained with Toluidine blue.
Figure 6:
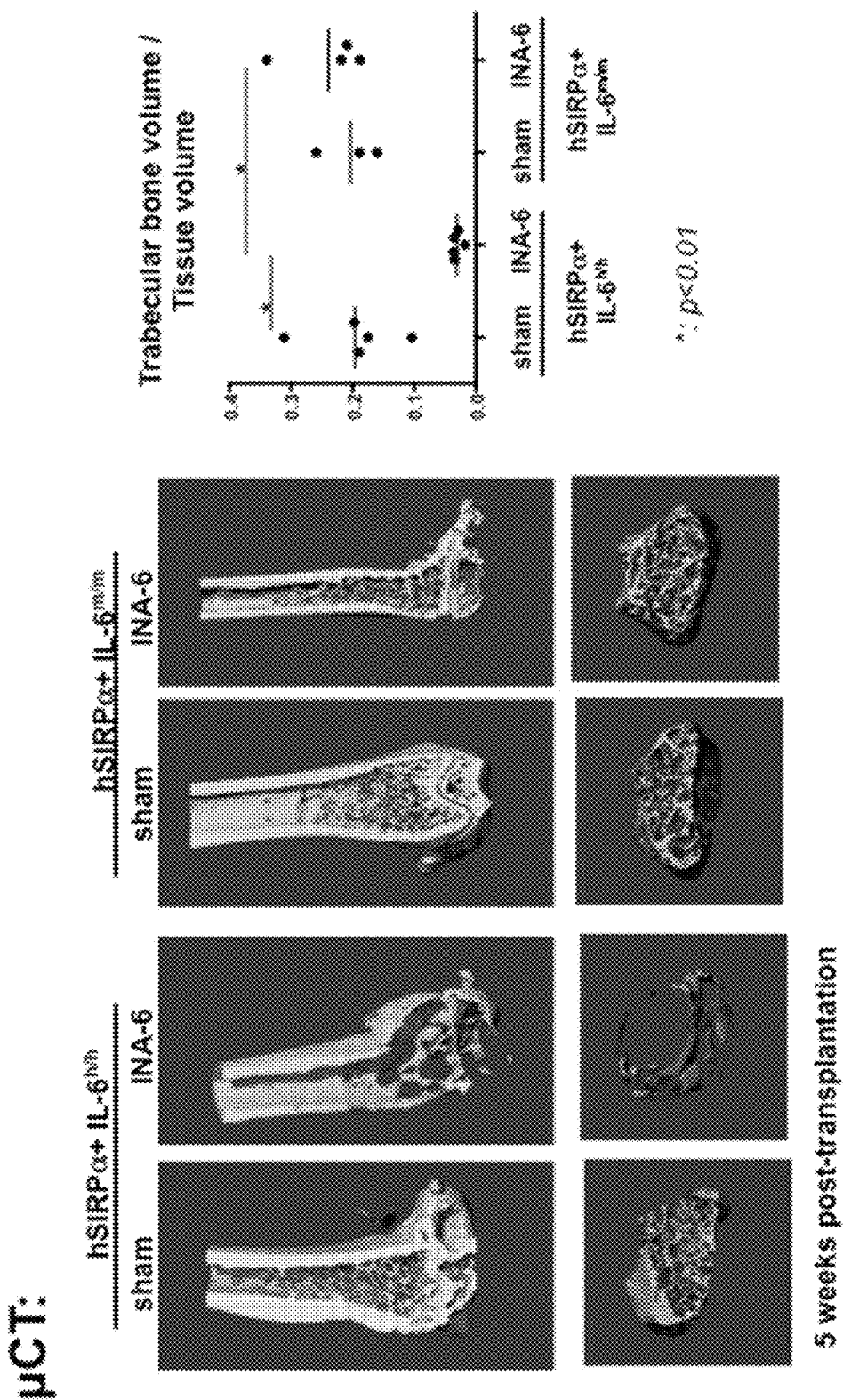
FIG. 6 is a set of images and a graph depicting the results of µCT analysis of murine femurs after INA-6 transplantation. $Rag2^{-/-}Il2rg^{null}$ $Il6^{h/h}$hSIRPa+ and control mice were sacrificed four weeks after engraftment with $5\times10^5$ intrafemorally injected INA-6 cells. Femurs were fixed in 70% ethanol and analyzed using a murine µCT. Trabecular bone and tissue volumes were quantified to calculate the ratio between bone to tissue volume. *: $p<0.01$ by student t-test.
Figure 7:
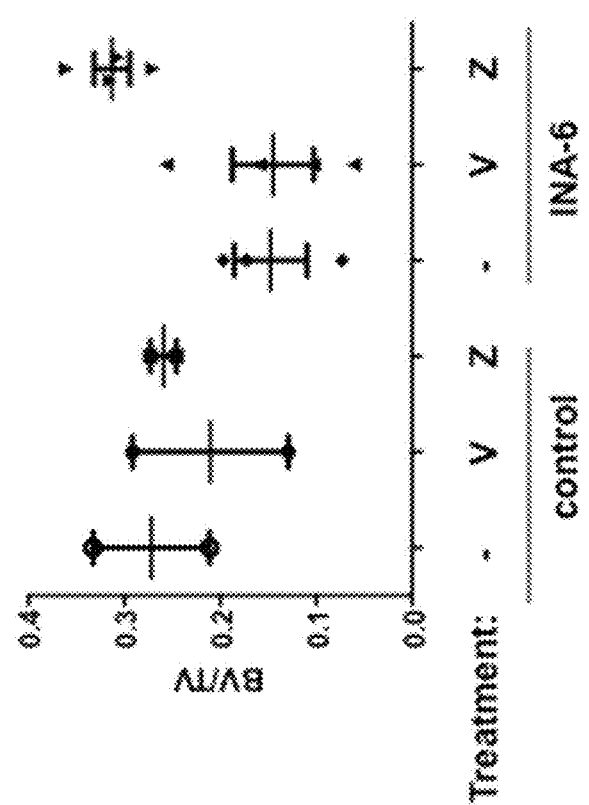
FIG. 7 is a graph depicting the results of µCT analysis of murine femurs after treatment with anti-myeloma drugs. $Rag2^{-/-}Il2re^{null}$ $Il6^{h/h}$hSIRPa+ were engrafted with $5\times10^5$ intrafemorally injected INA-6 cells and treated biweekly with Velcade® or Zometa®, respectively. After four weeks, mice were sacrificed and femurs were fixed in 70% ethanol for µCT analysis. Trabecular bone and tissue volumes were quantified to calculate the ratio between bone to tissue volume.

The data in FIG. 3 suggests that INA-6 cell do not home efficiently to the bone marrow and may grow instead at non-physiological sites. Therefore, it was next examined whether transplantation of the tumor cell line in its natural microenvironment is able to reproduce the pathology typically associated with human MM. To do so, intrabone injection of INA6 cells was tested. This strikingly resulted in bone destruction and resorption, which are aspects of the pathology seen in MM patients (FIG. 4-6). Specifically, the loss of trabecular bone mass was observed by histology, which was quantified by µCT. Moreover, only limited metastases to peripheral sites, such as the lung, was observed, which leads to the conclusion that the model may be further explored to investigate novel drugs interfering with this pathology. To test this conclusion INA-6-engrafted mice were treated with Zometa or Velcade, two drugs commonly used to treat multiple myeloma patients. Strikingly, Zometa treatment of mice injected with INA-6 cells was able to reduce bone resorption compared to untreated mice as quantified by µCT (FIG. 7).

The data disclosed herein demonstrate that humanization of the Il6 gene enables engraftment of multiple myeloma cell lines that typically require a human microenvironment. Engraftment recapitulates several pathological symptoms observed in patients including bone loss. Further, these symptoms can be treated using approved drugs highlighting the utility of this model to test new drugs.

Figure 8:
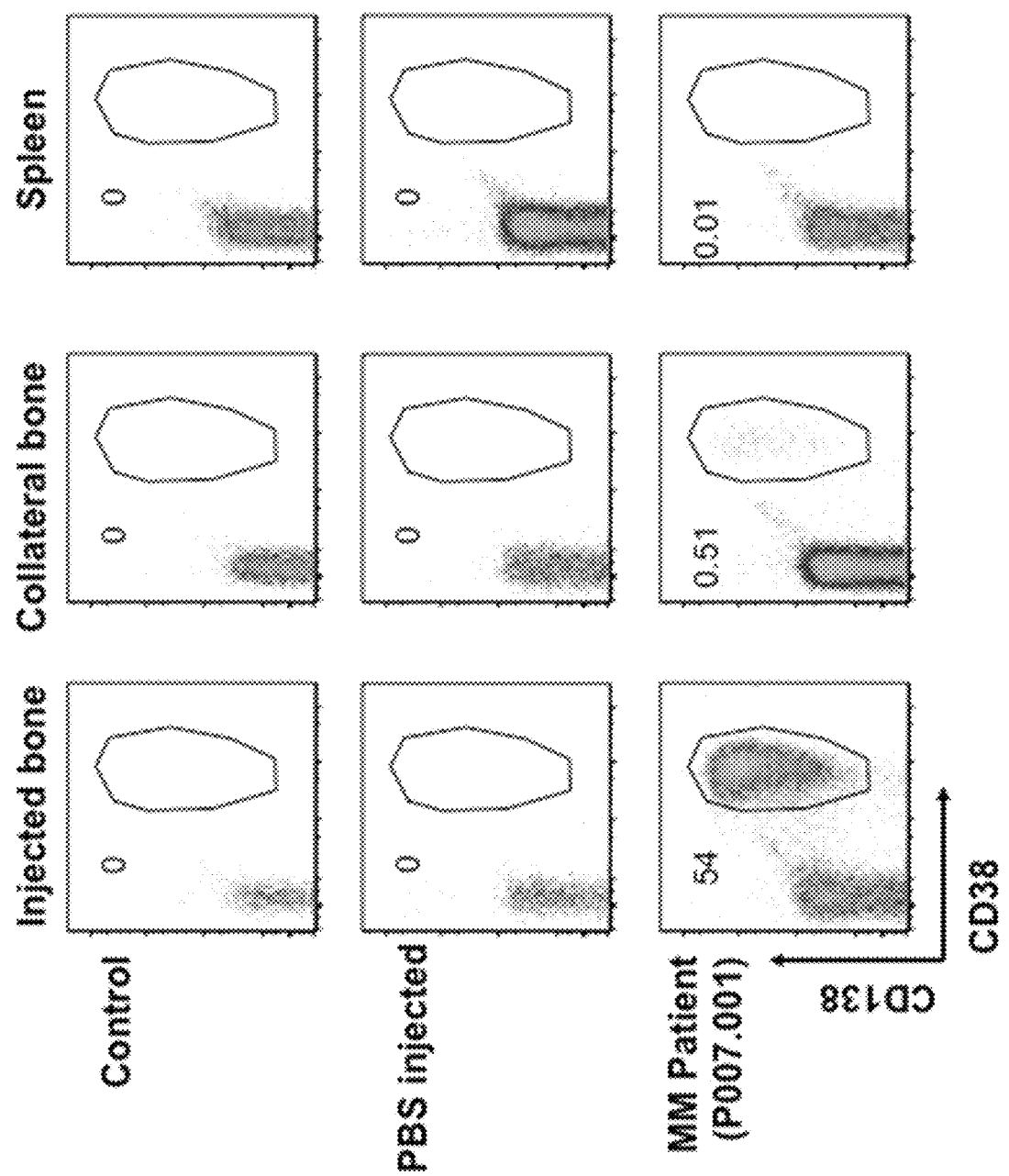
FIG. 8 is a set of graphs depicting the results of FACS analysis of primary cell engraftment in $Rag2^{-/-}$ $Il2rg^{null}$hSIRPa$^-$Tpo$^{h/h}$ Mcsf$^{h/h}$ Il3/Gmcsf$^{h/h}$ Il6$^{h/h}$ mice. Mice were transplanted with $1.5\times10^6$ intrafemorally injected CD3-depleted bone marrow cells and sacrificed twelve weeks later. Single-cell suspensions were generated from the injected femur, the collateral leg, and the spleen. Cells were stained for mCD45, hCD19, hCD38, and hCD138. FACS plots show events after gating on mCD45-negative cells. Numbers indicate frequency of CD38+CD138+ cells

Genetic humanization of cytokine genes enables engraftment of primary patient-derived multiple myeloma cells. Next, experiments were conducted to examine the transplantation of primary MM cells into genetically humanized mice. It has been previously demonstrated that humanization of multiple cytokines including thrombopoietin, IL-3, GM-CSF, and M-CSF as well as the macrophage inhibitory receptor SIRPa results in improved engraftment of human hematopoietic cells in immunodeficient mice (Strowig et al., 2011, Proc Natl Acad Sci USA, 108(32): 13218-13223; Rathinam et al, 2011, Blood, 118(11): 3119-3128; Rongvaux et al., 2011, Proc Natl Acad Sci USA, 108(6): 2378-2383; Willinger et al, 2011, Proc Natl Acad Sci USA, 108(6): 2390-2395). Specifically, humanization of IL-3 and GM- CSF as well as M-CSF improved engraftment of myeloid cells that have been demonstrated to be important for specific aspects of MM pathology. Transgenic expression of hSIRPa improves human cell engraftment, but the SIRPa-CD47 axis has also been recently implicated in tumorgenesis. Previously generated humanized mice were combined with human IL-6 knock-in mice to generate Rag2$^{-/-}$ Il2rg$^{null}$hSIRPa$^+$ Tpo$^{h/h}$ Mcsf$^{h/h}$ Il3/Gmcsf$^{h/h}$ Il6$^{h/h}$ mice. To evaluate the ability of this strain to support human cell engraftment, CD3-depleted bone marrow cells from MM patients was injected into the bone marrow of the mice. A high frequency of myeloma cells, as identified as CD138+ CD38+CD19− cells, was detected in the injected bone, while only few cells were detected in the collateral bone (FIG. 8).

These results suggest that the genetically humanized mice, described herein, support the engraftment of primary human MINI cells in vivo. The present data demonstrates that the humanization of cytokines gene encoding IL-6, TPO, IL-3, GM-CSF, and/or M-CSF enable engraftment of primary multiple myeloma cells from patients that typically require a human microenvironment for successful transplantation.

Example 2

Genetic Humanization of the IL-6 Gene Enables Engraftment of Mice with Human Hematopoietic Cells Materials and Methods Mice. The humanized IL-6 KI mouse was generated as described above. The chimeric mice were first bred with BALB/c mice and then backcrossed in order to obtain offspring with hIL-6 in homozygosity. Mice with the same mixed BALB/c×129 background were used as control.

Newborn pups (within first day of life) were sublethally irradiated by X-ray irradiation in a 4-hour interval with 2×150cGy. Four hours after the irradiation the mice were injected with 1-2×10$^5$ CD34$^+$ fetal liver (FL) cells in 20 µl of PBS into the liver by using a 30-gauge needle (Hamilton Company, NV, USA). Mice were weaned at 3 weeks of age. The mice were maintained under specific pathogen-free conditions and all experiments were performed in compliance with Yale Institutional Animal Care and Use Committee protocols.

Analysis of human and mouse hematological cell populations. The mice were bled from retro-orbital plexus under isofluorane anesthesia at different times after transplantation. Plasma samples were collected and stored at −20° C. for further Ig measurement. Red blood cells were lysed two times by using Ammonium-Chloride (ACK) lysing buffer and the remaining PBMC were resuspended in FACS buffer (PBS supplemented with 5% FBS and 5 mM EDTA).

When the mice were killed, a single-cell suspension of cells was obtained from the bone marrow (BM), thymus and spleen. Samples were then stained with fluorochrome-labeled mAbs against mouse and human cell surface antigens according to the manufactures' instructions. The following anti-human mAbs were used: CD45 (HI30), CD19 (HIB19), CD3 (UCHT1), CD4 (RPA-T4), CD8 (HIT8a), CD20 (2H7), CD5 (UCHT2), CD27 (O323), CD24 (ML5), CD10 (HI10a), all from Biolegend, Calif., USA; CD33 (WM53), CD38 (HIT2), IgM (G20-127), CD138 (MI15) from BD Biosciences and CD34 (AC136) from Miltenyi Biotec. The mouse cells were stained with an anti-murine CD45 Ab (30-F11, Biolegend). Samples were acquired on the LSRII (BD Biosciences) cytometer and analyzed on FlowJo (Treestar, Oreg., USA) software.

Measurement of human immunoglobulins. Total immunoglobulins (Igs) were measured in the plasma collected from the mice by ELISA. 96 well plates (Nunc, N.Y., USA) were coated at 4° C. overnight with 20 µg/ml purified goat anti-human IgM and IgG (Southern Biotechnology, AL, USA). After washing and blocking with PBS 1% bovine serum albumin (BSA, Sigma-Aldrich) appropriate dilutions of the samples were added for 2 hours at room temperature (RT). Plates were washed and incubated for 1 hour at RT with isotype specific secondary biotinylated antibodies (Southern Biotechnology) followed by Streptavidin-HRP (Pierce Protein Research Products, IL, USA). After a final wash the enzyme activity was determined using the TMB substrate solution followed by the stop solution (both from Pierce Protein Research Products). The absorbance was measured at 450 nm. A sample of human serum from Bethyl (TX, USA) was used as reference.

Statistical analysis. All data were expressed as average±standard error of mean (SEM) with the exception of the Ab levels that were plotted as geometric mean. The non-parametric Mann-Whitney U test was used to determine statistical significance between two groups. Differences were considered significant when the p values were lower than 0.05.

Results

Figure 9:
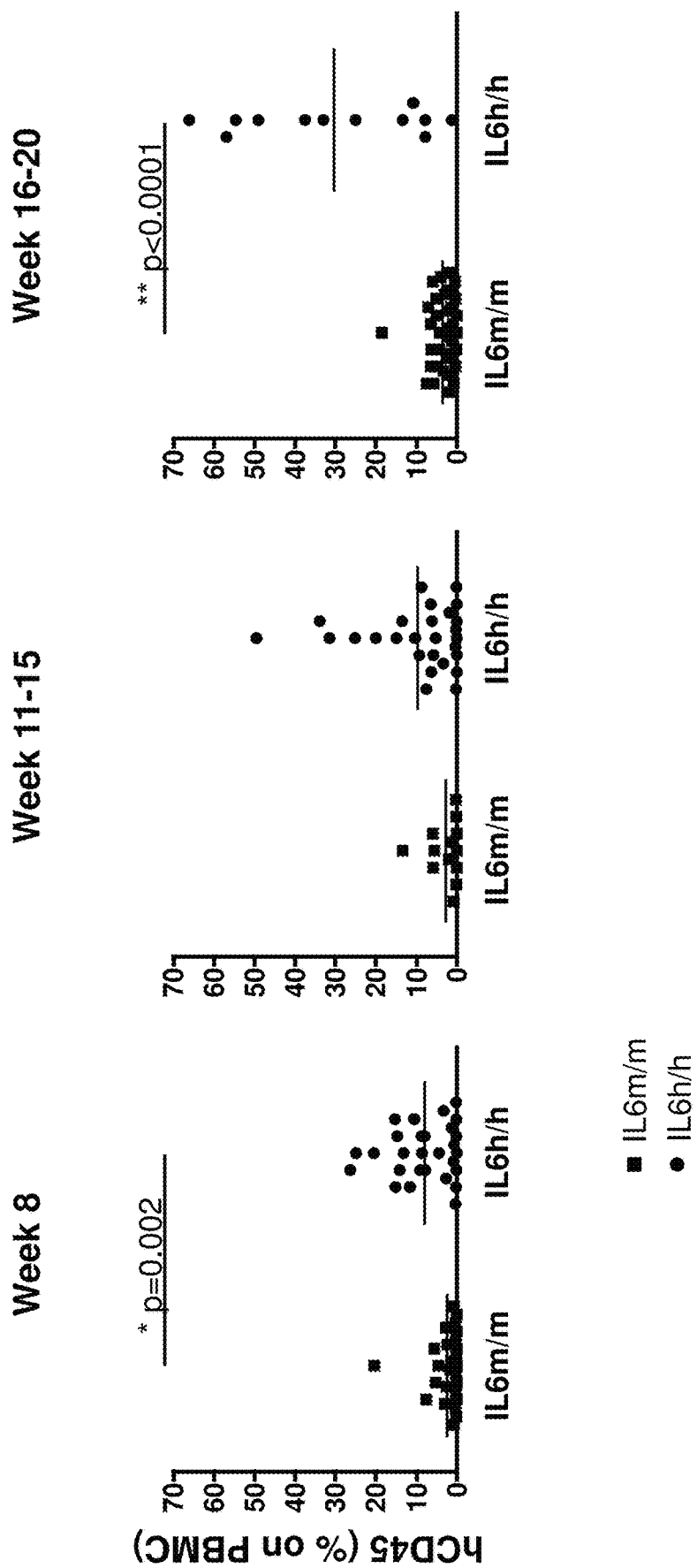
FIG. 9 depicts the results of experiments assessing the percentage of human hematopoietic (hCD45+) cells in blood in engrafted mice determined by flow cytometry. Horizontal bars indicate the respective mean frequencies.
Figure 10:
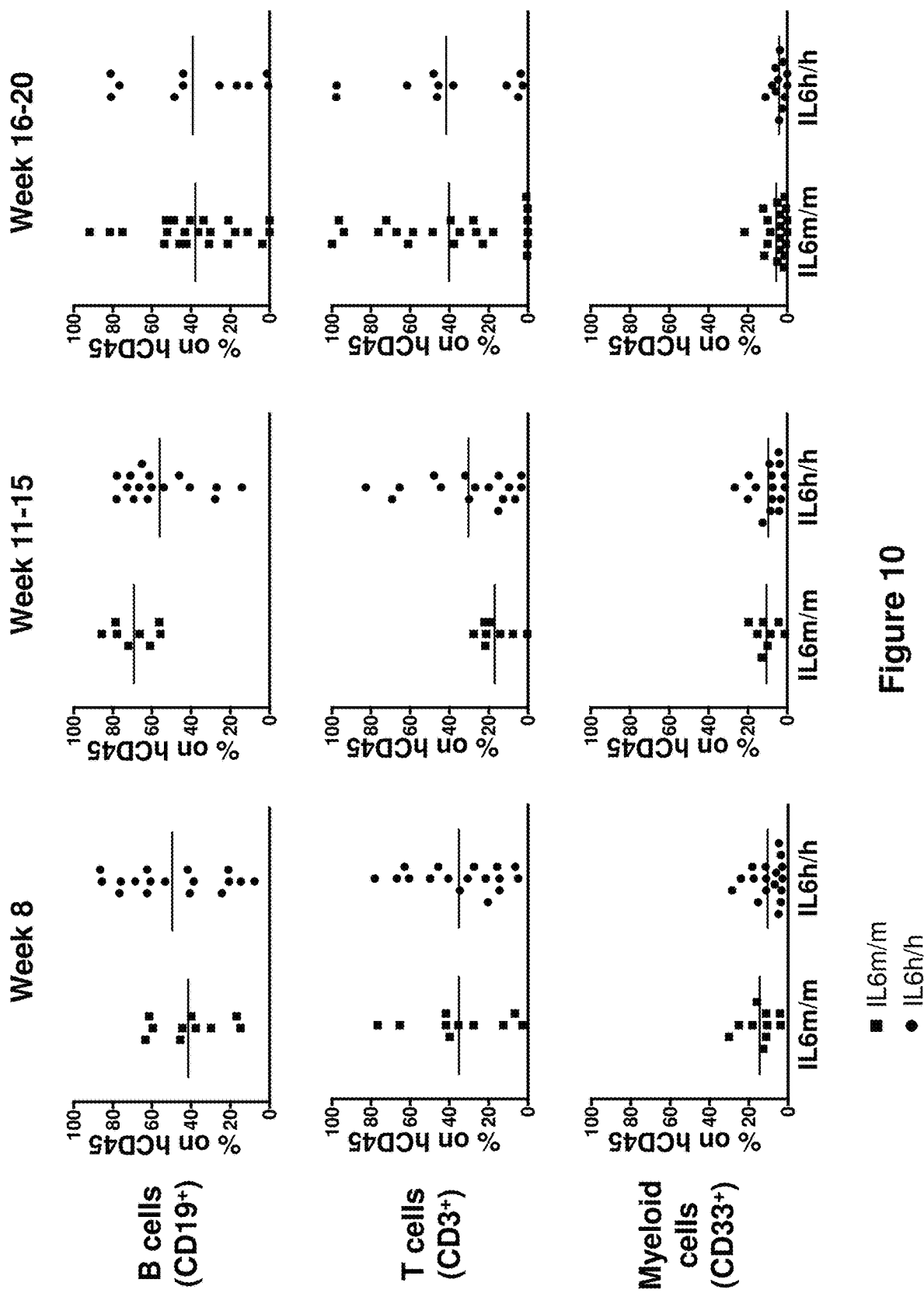
FIG. 10 depicts the results of experiments assessing the percentage of hCD45 of B (CD19+), T (CD3+) and myeloid (CD33+) cells in blood in engrafted mice determined by flow cytometry. Only mice with a hCD45 percentage higher than 2% are shown.

Peripheral blood engraftment in human CD34$^+$ cell transplanted RAG2$^{-/-}$ γ$_c$$^{-/-}$ mice. The IL6 h/h mice showed a higher peripheral blood (PB) engraftment throughout the time of the analysis when compared to the IL6 m/m mice and their engraftment increased over time (FIG. 9). There were no major differences in the composition of the human cells between the 2 groups of mice at any time point tested (FIG. 10). In both groups B and T cell percentages were similar at week 8 and week 16-20 whereas at weeks 11-15 there was a higher percentage of B cells (69.23±3.97 in IL6 m/m and 55.91±4.86 in IL6h/h) than T cells (16.86±3.14 in IL6 m/m and 30.26±6.23 in IL6h/h). Myeloid CD33$^+$ cells represented a minor component of the human cell and their percentage decreased over time.

Figure 11:
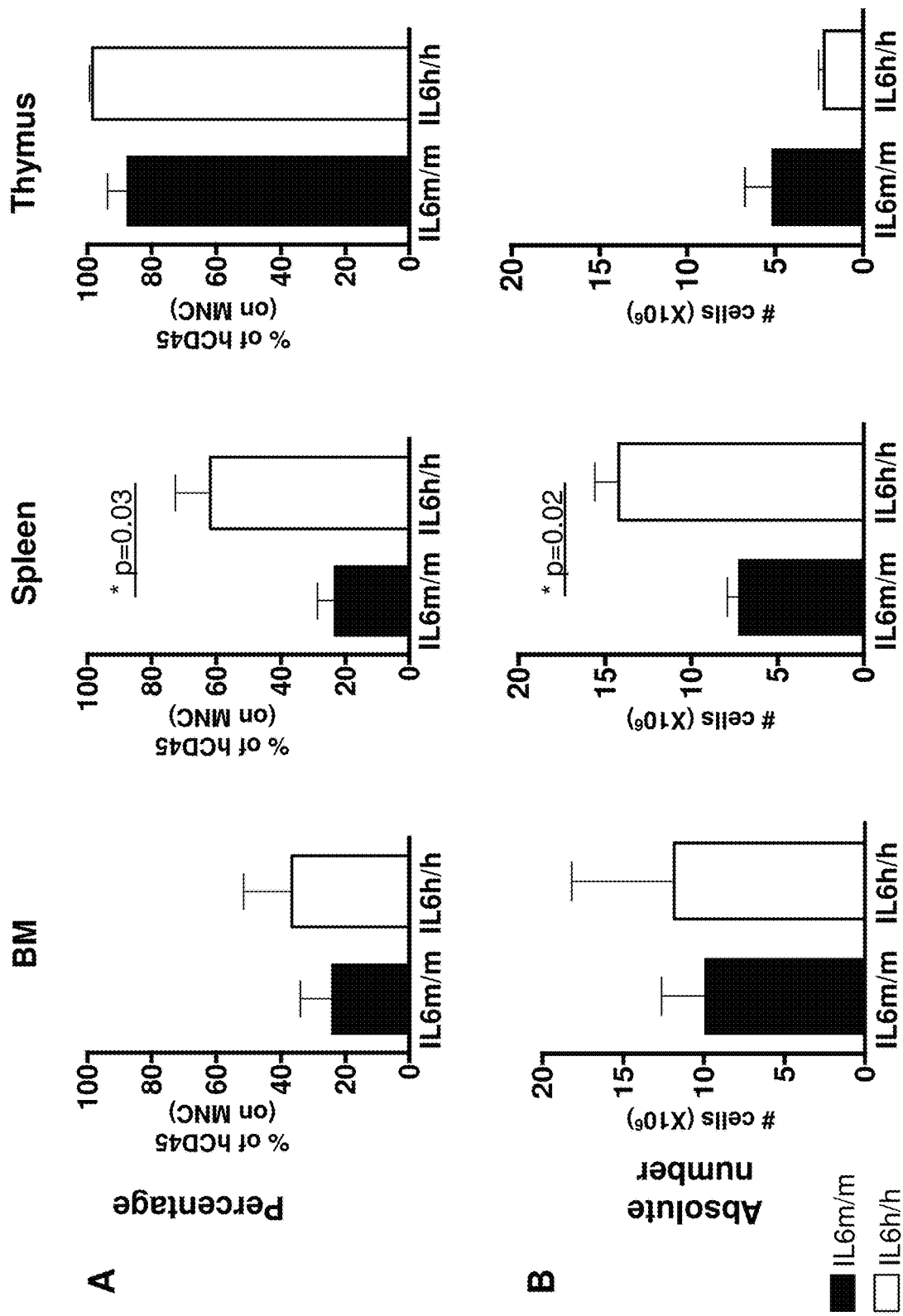
FIG. 11, comprising Panels A and B, depicts the results of experiments assessing percentage (Panel A) and number (Panel B) of human CD45+ cells in BM, spleen and thymus of 20 week engrafted mice. Bars represent average±SEM of 4/5 mice for group.

Organ cell engraftment and composition of human CD34$^+$ cell reconstituted RAG2$^{-/-}$ γ$_c$$^{-/-}$ mice. Cells of human origin were found in the hemato-lymphoid organs, such as BM, spleen and thymus (FIG. 11, Panel A). Interestingly the spleen of the IL6 h/h mice displayed a greater human engraftment than IL6 m/m mice (61.75%±10.87 versus 23.56%±5.2). These data were confirmed by the doubling in the absolute number of human cells (14.21×10$^6$±1.38 versus 7.26×10$^6$±0.66) (FIG. 11, Panel B).

Figure 12:
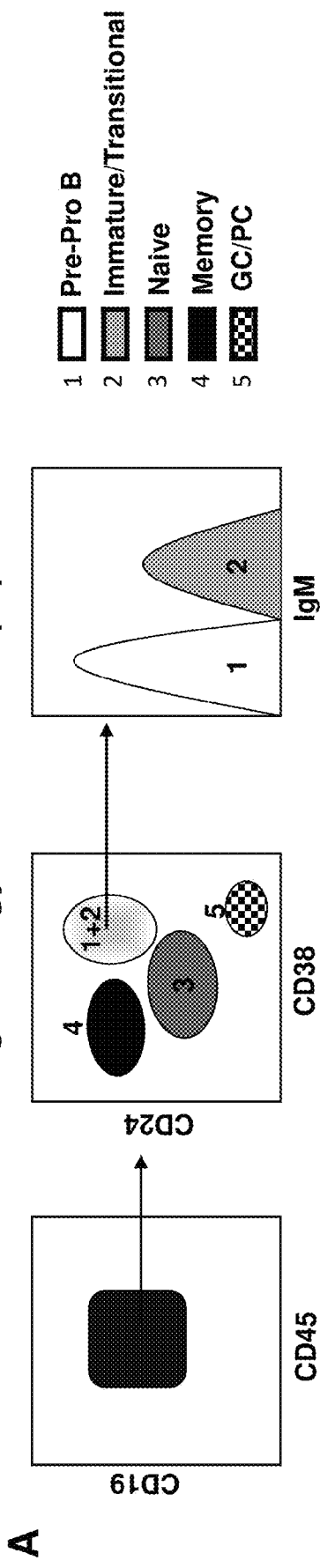
FIG. 12, comprising Panels A and B, depicts the results of FACS experiments assessing human cells. (Panel A) Drawing showing the gating strategy used for separating different B cell populations by flow cytometry. (Panel B) Percentage of different B cell subsets within the human CD45+CD19+ cells in 20 week old mice. Bars represent average±SEM of 4/5 mice for group.
Figure 12:
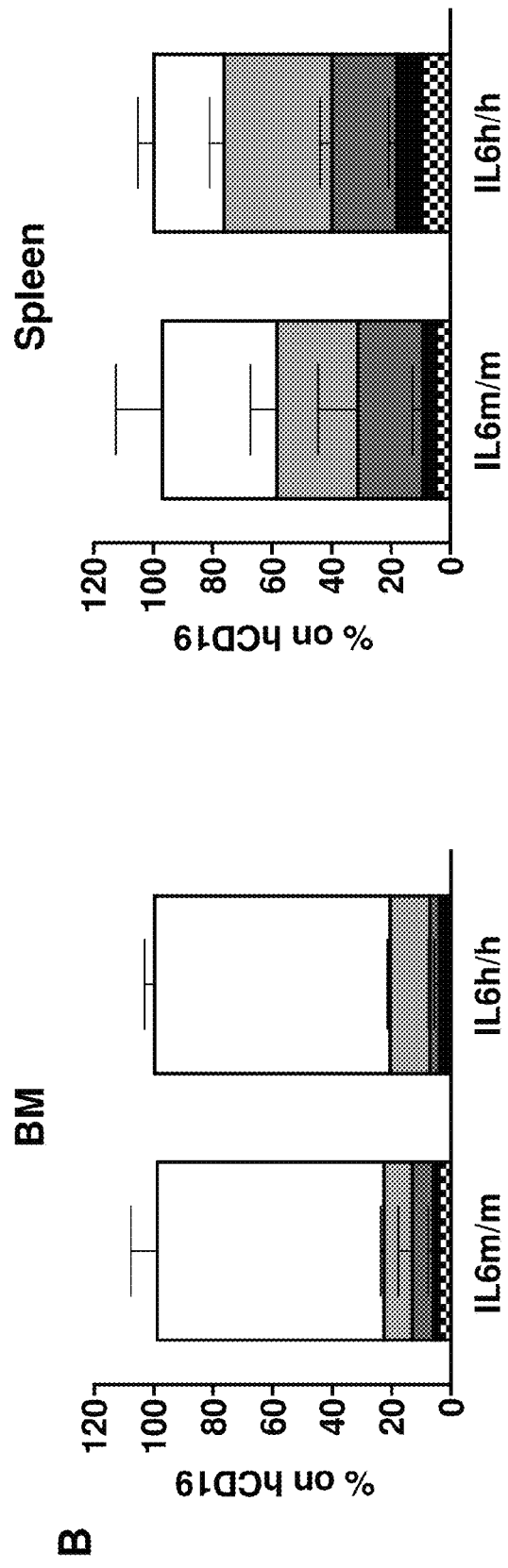

B cell maturation in human CD34$^-$ engrafted RAG2$^{-/-}$ γ$_c$$^{-/-}$ mice. The maturation stages of the human B cells were studied in the BM and spleen of the engrafted mice using the gating strategies illustrated in FIG. 12, Panel A, based on the usage of a combination of CD24, CD38 and surface IgM antibodies. This strategy is particularly helpful in dissecting the presence of the transitional B cell subset. In BM the main compartment was made by the Pro-/Pre-B cells (FIG. 12, Panel B) with no difference between the IL6 m/m and the IL6 h/h mice (76.04%±9.09 and 79.07%±3.43 respectively). The spleen of both groups contained some mature B cells (~20%) but still a high percentage of immature/transitional cells (27.13%±8.99 and 36.45%±5.12).

Figure 13:
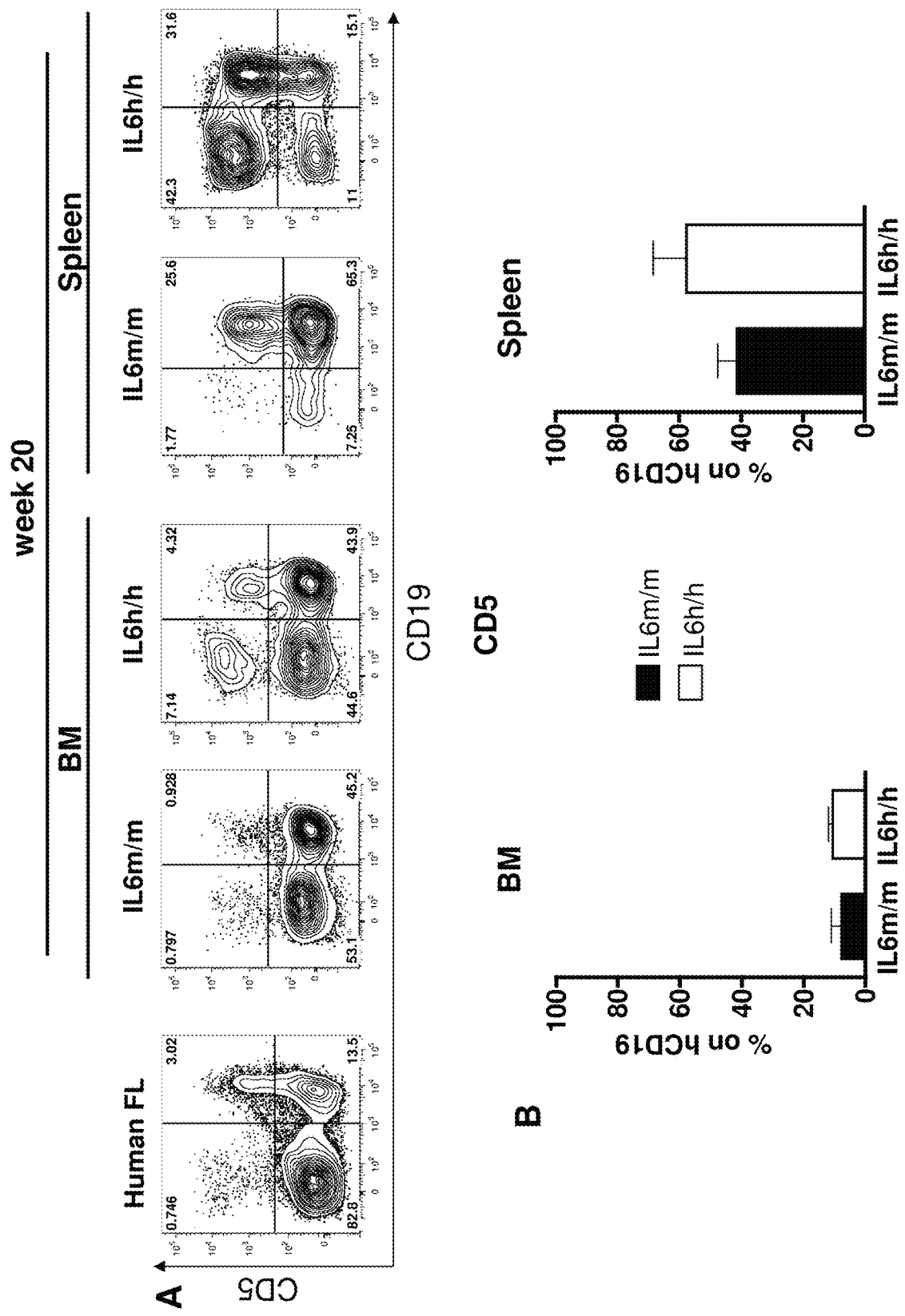
FIG. 13, comprising Panels A and B, depicts the results of FACS experiments assessing human cells. (Panel A) Representative flow cytometric analysis of CD5+ B cells in human fetal liver (FL) and 20 week old mice. Numbers in the quadrants indicate percentages of cells. All plots are gated on human CD45+ cells. (Panel B) Percentage of CD5 on human B cells in BM and spleen of 20 week engrafted mice. Bars represent average±SEM of 4/5 mice per group.

A significant percentage of B cells in the spleen were CD5$^+$(FIG. 13, Panel B), a marker not commonly expressed on human BM and peripheral B cells but found in low percentage on the FL B cells (FIG. 13, Panel A).

Figure 14:
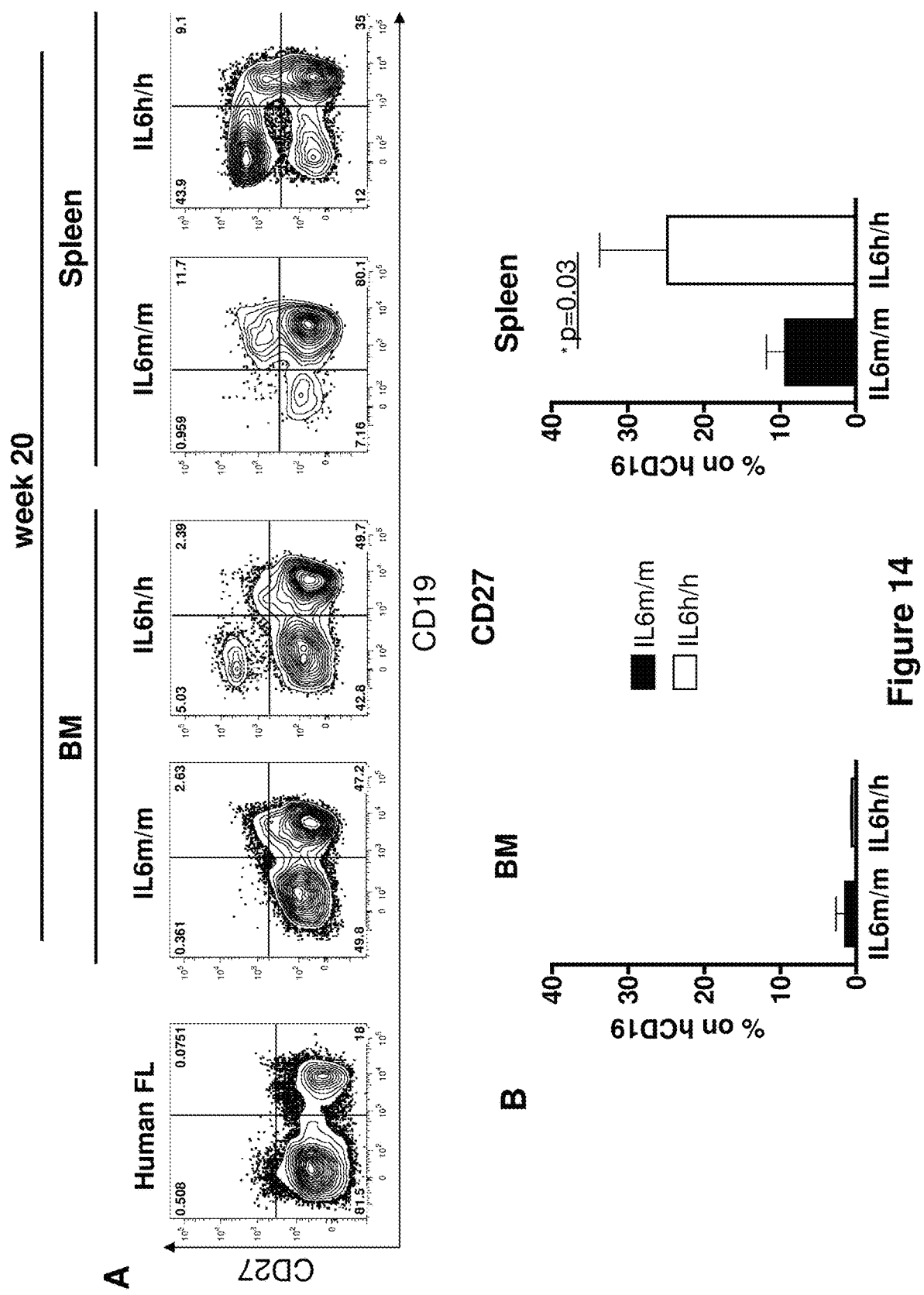
FIG. 14 depicts the results of FACS experiments assessing human cells. (Panel A) Representative flow cytometric analysis of CD27+ B cells in human fetal liver (FL) and 20 week old mice. Numbers in the quadrants indicate percentages of cells. All plots are gated on human CD45+ cells. (Panel B) Percentage of CD27 on human B cells in BM and spleen of 20 week engrafted mice. Bars represent average±SEM of 4/5 mice per group.

The IL6 h/h mice showed a sharp increase in the percentage of the CD27+ B cells in the spleen when compared to the IL6 m/m mice (24.73%±8.94 versus 9.46%±2.32) but very few CD27+ cells were found in the BM (FIG. 14, Panels A and B).

Antibody production in human CD34+ engrafted RAG2$^{-/-}\gamma_c^{-/-}$ mice. As the B cells were found in the engrafted mice, the concentration of the human IgM and IgG in the plasma collected at 12 and 20 weeks after the human cell transplantation was then measured. Both IL6 m/m and IL6 h/h mice secreted human IgM and IgG (FIG. 15).

Figure 15:
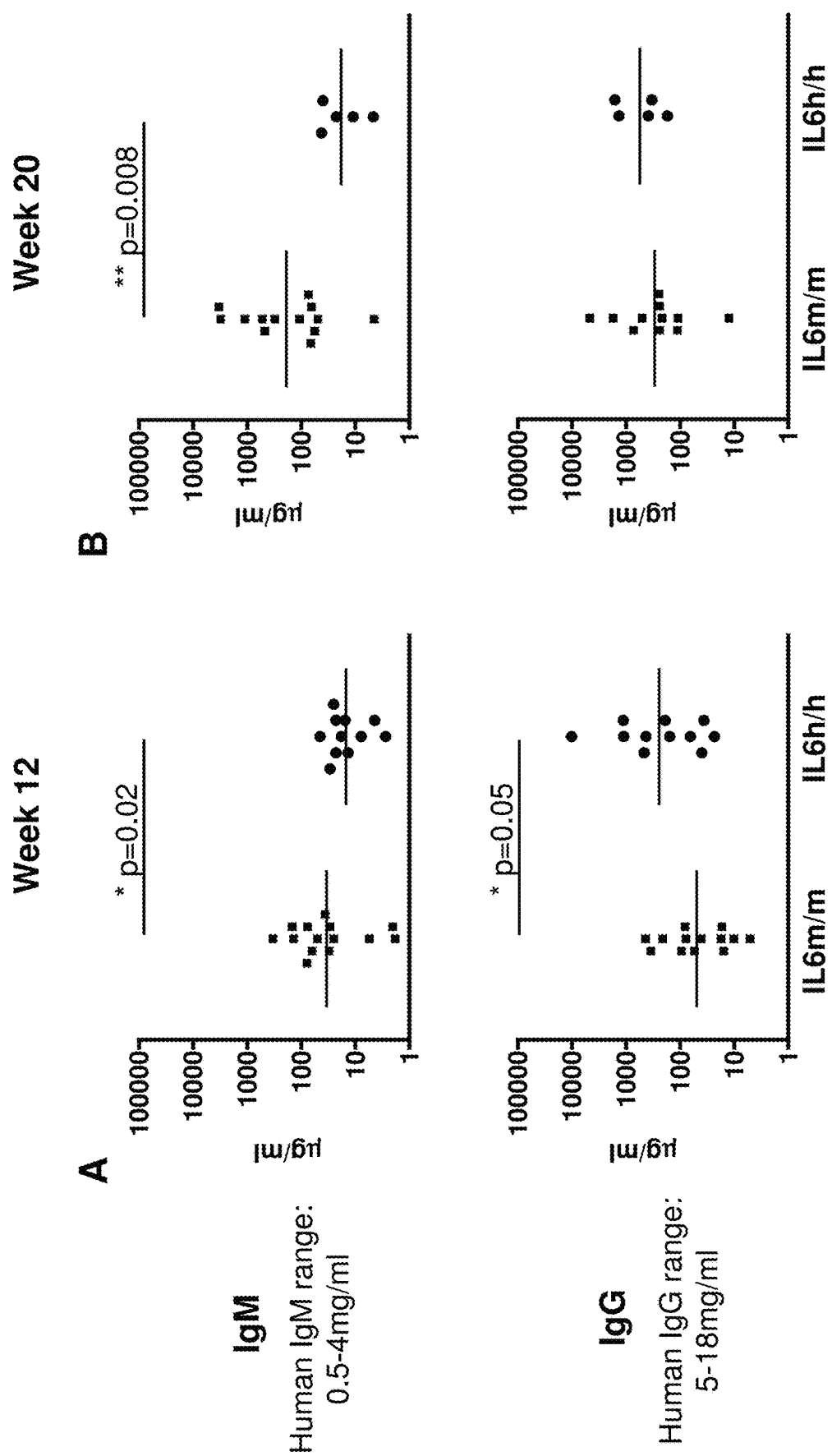
FIG. 15 depicts the results of experiments assessing the total human IgM and IgG levels in plasma samples of 12 (Panel A) and 20 (Panel B) week old mice. Horizontal bars indicate the respective geometric means. Mice with a PB human engraftment lower than 2% were excluded from the analysis.

In general there was a higher percentage of IL6 h/h mice secreting antibodies compared to the IL6 m/m ones with the former mice showing a smaller level of IgM level (14.69 µg/ml versus 33.66 µg/ml at week 12 and 18.25 µg/ml versus 190.2 µg/ml at week 20) but an increased level of IgG (243 µg/ml versus 49.6 µg/ml at week 12 and 553.6 µg/ml versus 297.2 µg/ml at week 20) (FIG. 15, Panel A). Both IgM and IgG average level rose over time in IL6 m/m mice (FIG. 15, Panel B). Conversely the serum Igs remained steady in IL6 h/h mice.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of generating a mouse model of human B cell development and function, the method comprising:
   transplanting a population of human hematopoietic cells into a genetically $Rag2^{-/-}$, $IL2rg^{null}$ modified mouse that is immunodeficient and comprises in its genome a nucleic acid encoding human IL-6 operably linked to the endogenous mouse IL-6 promoter at the mouse IL-6 locus, wherein the mouse expresses human IL-6 and does not express mouse IL-6, and wherein the mouse produces human B cells.

2. The method of claim 1, wherein the transplanted population of hematopoietic cells comprises CD34+ cells.

3. The method of claim 1, wherein the transplanted population of hematopoietic cells comprises multiple myeloma cells.

4. The method of claim 1, wherein the transplanting comprises intrafemoral and/or intratibial injection.

5. The method of claim 1, wherein the mouse further comprises in its genome a nucleic acid encoding human SIRPa, or a nucleic acid encoding a fusion protein comprising a biologically active fragment of a full length human SIRPA polypeptide, operably linked to a SIRPa promoter.

6. The method of claim 5, wherein the SIRPa promoter is the mouse SIRPa promoter, and the nucleic acid encoding human SIRPa, or the nucleic acid encoding a fusion protein comprising a biologically active fragment of a full length human SIRPA polypeptide, is operably linked to the mouse SIRPa promoter at the mouse SIRPa locus.

7. The method of claim 1, wherein the mouse comprises in its genome at least one additional nucleic acid selected from the group consisting of:
   i) a nucleic acid encoding human M-CSF operably linked to a M-CSF promoter;
   ii) a nucleic acid encoding human IL-3 operably linked to an IL-3 promoter;
   iii) a nucleic acid encoding human GM-CSF operably linked to a GM-CSF promoter; and
   iv) a nucleic acid encoding human TPO operably linked to a TPO promoter.

8. The method of claim 7, wherein the M-CSF promoter is the mouse M-CSF promoter, and the nucleic acid encoding human M-CSF is operably linked to the mouse M-CSF promoter at the mouse M-CSF locus, the IL-3 promoter is the mouse IL-3 promoter, and the nucleic acid encoding human IL-3 is operably linked to the mouse IL-3 promoter at the mouse IL-3 locus, the GM-CSF promoter is the mouse GM-CSF promoter, and the nucleic acid encoding human GM-CSF is operably linked to the mouse GM-CSF promoter at the mouse GM-CSF locus, and the TPO promoter is the mouse TPO promoter, and the nucleic acid encoding human TPO is operably linked to the mouse TPO promoter at the mouse TPO locus.

9. The method of claim 1, wherein the transplanting comprises injecting the population of human hematopoietic cells into the liver of the mouse.

10. The method of claim 3, wherein the human multiple myeloma cells are INA6 cells.

* * * * *